(12) United States Patent
Hafeman et al.

(10) Patent No.: US 7,534,338 B2
(45) Date of Patent: May 19, 2009

(54) METHODS AND DEVICES FOR CONCENTRATION AND PURIFICATION OF ANALYTES FOR CHEMICAL ANALYSIS INCLUDING MATRIX-ASSISTED LASER DESORPTION/IONIZATION(MALDI) MASS SPECTROMETRY (MS)

(75) Inventors: Dean Hafeman, Hillsborough, CA (US);
Kilian Dill, Monroe, WA (US); James B. Harkins, Knoxville, TN (US);
Richard M. Caprioli, Brentwood, TN (US); Jeremy Norris, Smyrna, TN (US);
Nathan S. Lewis, La Canada, CA (US);
Daniel Kuban, Knoxville, TN (US);
Charles E. Witkowski, II, Knoxville, TN (US)

(73) Assignee: Protein Discovery, Inc., Knoxville, TN (US)

( * ) Notice: Subject to any disclaimer, the term of this patent is extended or adjusted under 35 U.S.C. 154(b) by 0 days.

(21) Appl. No.: 10/963,336

(22) Filed: Oct. 12, 2004

(65) Prior Publication Data
US 2005/0116161 A1 Jun. 2, 2005

Related U.S. Application Data

(60) Provisional application No. 60/511,615, filed on Oct. 10, 2003, provisional application No. 60/581,843, filed on Jun. 22, 2004, provisional application No. 60/586,099, filed on Jul. 7, 2004.

(51) Int. Cl.
*H01J 49/04* (2006.01)

(52) U.S. Cl. ............... 205/288; 250/282; 204/216; 435/287.2

(58) Field of Classification Search .......... 250/288
See application file for complete search history.

(56) References Cited

U.S. PATENT DOCUMENTS

| | | | |
|---|---|---|---|
| 3,271,198 A * | 9/1966 | Winogradoff et al. | 429/111 |
| 5,810,989 A | 9/1998 | Krihak et al. | |
| 6,494,230 B2 | 12/2002 | Chow | |
| 6,783,672 B2 * | 8/2004 | Tubbs et al. | 210/198.2 |
| 6,919,046 B2 * | 7/2005 | O'Connor et al. | 422/100 |
| 6,952,011 B2 | 10/2005 | Brown et al. | |
| 7,030,373 B2 * | 4/2006 | Vestal et al. | 250/288 |
| 7,037,419 B2 * | 5/2006 | James | 204/615 |
| 2002/0094533 A1 | 7/2002 | Hess et al. | |
| 2002/0122747 A1 * | 9/2002 | Zhao et al. | 422/99 |

FOREIGN PATENT DOCUMENTS

| WO | WO 00/45168 | 8/2000 |
|---|---|---|
| WO | WO 03/025578 | 3/2003 |

* cited by examiner

*Primary Examiner*—David A. Vanore
*Assistant Examiner*—Phillip A. Johnston
(74) *Attorney, Agent, or Firm*—McDonnell Boehnen Hulbert & Berghoff LLP

(57) ABSTRACT

Analytical methods and devices are disclosed for separating low abundance analytes by electrophoretically driving the analytes through a sieving matrix to first remove high molecular weight species. Subsequently the remaining low abundance analytes are electrophoretically focused onto a capture membrane where the analytes become bound within a small capture site. After this step the capture membrane may be allowed to dry and then attached to a conductive MALDI sample plate.

30 Claims, 38 Drawing Sheets

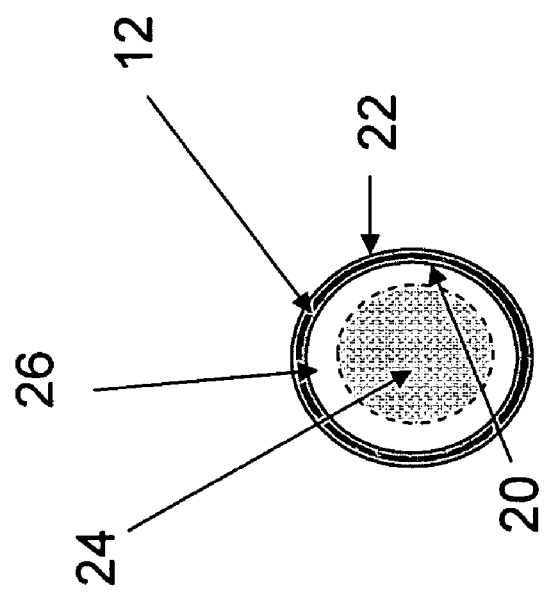
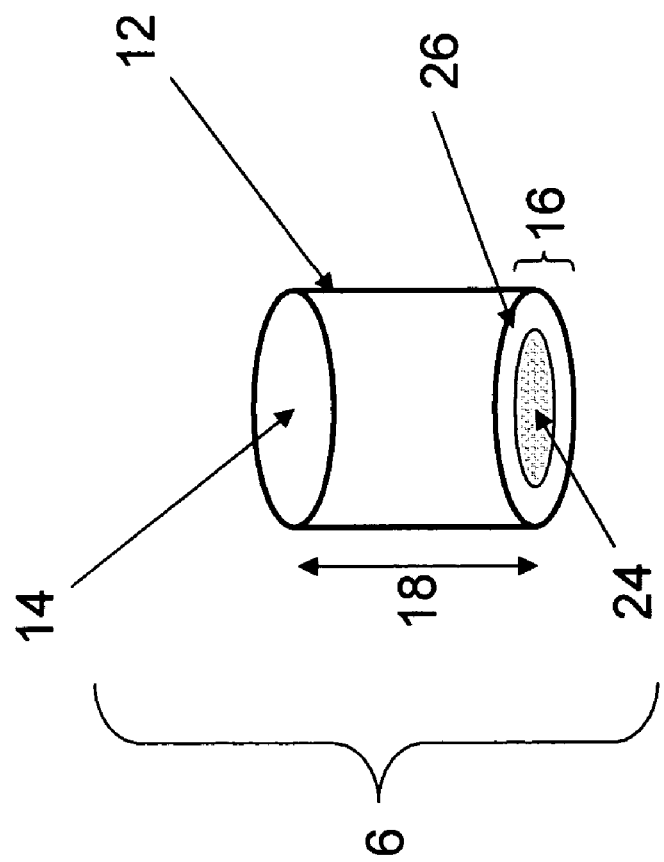
Figure 4b
Figure 4a

METHODS AND DEVICES FOR CONCENTRATION AND PURIFICATION OF ANALYTES FOR CHEMICAL ANALYSIS INCLUDING MATRIX-ASSISTED LASER DESORPTION/IONIZATION(MALDI) MASS SPECTROMETRY (MS)

CROSS-REFERENCE

This application claims the benefit of U.S. Provisional Application Nos. 60/511,615, filed Oct. 10, 2003; 60/581,843, filed Jun. 22, 2004; and 60/586,099 filed Jul. 7, 2004 which are incorporated by reference in its entirety.

BACKGROUND

1. Field of Invention

The present invention relates to Mass Spectrometry and, more specifically, to pre-concentration and purification of analytes from biological samples, such as human serum, to be analyzed by Matrix-Assisted Laser Desorption Ionization Mass Spectrometry (MALDI MS).

2. Background of the Related Art

Matrix-assisted laser desorption/ionization mass spectrometry (MS) analysis of samples deposited onto MALDI target plates is rapidly becoming a method of choice for analysis of proteins, peptides and other biological molecules. The MALDI-MS procedure is a very sensitive analytical method and is probably the MS procedure most compatible with biological buffers. Further, its ability to generate high-mass ions at high efficiency from sub-picomole quantities of biological macromolecules makes this technique extremely useful for macromolecule analysis. Analysis of peptide analytes in crude biological samples, such as blood, plasma, or serum, however offers special problems for mass spectrometry analysis as described below.

The first problem to be overcome is that the biological samples contain high concentrations of salts (e.g. sodium, potassium, chloride, phosphate and carbonate). The anions are especially effective in suppressing the ionization of peptide samples by the usual MALDI analysis procedures. The cations also are problematic in that they generate adduct spectra that split the primary mass peaks into a multitude of smaller peaks having the additional mass of the cation adducts. Also, the success of MALDI-MS analysis depends to a great extent on the ability to effectively crystallize a MALDI matrix substance mixed together with the analyte prior to injection into the mass spectrometer. The MALDI matrix substance is needed to absorb the laser light that provides for atomization and ionization of the matrix together with adsorbed analyte substances within samples to be analyzed. The ionized analyte molecules then are accelerated into a mass spectrometer ion detector by a high electrical field provided by high voltages on an anode and cathode within the mass spectrometer. When even relatively small amounts of contaminants, such as salts or glycerol, are present the ability of MALDI matrices to efficiently desorb and ionize analytes, such as proteins and peptides, is dramatically reduced. Furthermore, high salt concentrations increase both the threshold laser intensity required for MALDI-MS and the intensity of salt-adducted peptides (at the expense of free peptide signal).

Secondly, in samples, such as human serum, analyte peptides are frequently present at very low copy number compared to interfering proteins (e.g. albumin, immunoglobulins and transferrin). The peptides of interest often are present at just 1 micromole per liter to 1 picomole per liter (e.g. 1 microgram to 1 picogram per ml). In contrast total albumins and gamma globulins such as IgG, IgM, are present at levels ranging from 0.01 to 0.1 grams per ml, i.e. up to $1 \times 10^{11}$-fold greater in mass. Thus, the major abundance proteins heavily dominate MALDI spectra of the mixture. Minor components are rarely observed because the low intensity peaks are obscured by the major peaks. This problem is made much more difficult in biological samples, such as human serum where such low copy number molecules are to be detected in the presence of many orders of magnitude higher molar concentrations of interfering proteins (e.g. albumin, immunoglobulins and transferrin) and salts (e.g. sodium, potassium, chloride, phosphate and carbonate).

Thirdly, many of the analyte peptides are hydrophobic and are bound to the major proteins found in blood, plasma, or serum, especially albumin which tends to bind hydrophobic molecules nonspecifically. Thus, removal of the unwanted proteins also results in the loss of analyte peptides. Chemically disruptive agents, such as salts and detergents are known to assist in the dissociation of analyte peptides from albumin; however, these agents actively suppress the MALDI process. For example polyethylene glycol (PEG) and Trition desorb by MALDI more efficiently and have a greater MALDI signal than do peptides and proteins. As a result these species often suppress the MS signal from proteins and peptides. Thus, after the addition of chemically disruptive agents to dissociate analyte peptides from albumin, one must separate the analyte peptides from both the disruptive agent's albumin and other contaminating proteins. Additionally, the separation must be performed in such a way that the minor component peptide analytes are not lost during the separation process. This separation is made especially difficult when the analytes are hydrophobic and tend to adhere to hydrophobic surfaces. Unfortunately, purification of biopolymers by LC methods frequently results in 30% sample losses and can add further contaminants to samples. For most MALDI-MS users, this amount of sample loss is unacceptable.

Lastly, because the analyte peptides are present at such low levels, they must be concentrated prior to MALDI-MS analysis. Carrying out first the dissociation of peptides, the separation of components, and then the concentration, by prior art methods is tedious and requires multiples steps that are both time-consuming and labor-intensive. One object of the present invention is to provide methods and devices that are able to perform these steps in a convenient and efficient manner, thereby increasing the sample throughput, as well as decreasing the cost of analysis.

Many, often cumbersome and labor-intensive, techniques have been reported in the literature for separation of contaminants prior to MALDI-MS analysis. Traditionally, liquid chromatography (LC) or affinity based methods have been used to the greatest extent. Purification via LC methods involves chemically attaching linker molecules to a stationary phase (producing a functionalized stationary phase) in a LC column. Once the sample is loaded into the column, a mobile phase is flowed through the stationary phase. The fraction of the time each analyte spends bound to the stationary phase, rather than in the mobile phase, determines the relative migration rate of different analytes (as well as contaminants and interfering species) through the LC column, providing for purification of the analytes. For example, analyte molecules of interest, such as peptides and proteins, can be adsorbed onto a functionalized stationary phase while the contaminants are eluted from the column. Next, the mobile phase is adjusted so as to release the molecules of interest from the functionalized stationary phase. Often, a volatile buffer that is compatible with MALDI-MS, such as an acetonitrile/water mixture, is used as the mobile phase in this step. In this fashion, the purified molecules of interest are eluted from the LC column and collected for MALDI-MS analysis. The sample is now relatively free of salts and other contaminants that would otherwise interfere or otherwise limit the sensitivity of the analysis.

There is a need therefore, for new devices, methods and procedures for concentrating samples prior to MALDI-MS analysis.

OBJECTS OF THE INVENTION

One objective of the invention is to provide methods for pretreatment of crude biological samples, such as serum, plasma, whole blood, cerebrospinal fluid, urine, etc. for sensitive analysis by MALDI-mass spectrometry. Another object of the invention is to provide such methods that are convenient to carry out in an efficient manner, thereby increasing the sample throughput, as well as decreasing the cost of analysis. Still another object of the invention is to provide for devices to carry out these methods wherein the devices are similarly convenient to use, offer high quality data, and are relatively inexpensive to produce. Optimally, the devices will be provided pre-cleaned and preconditioned to require a minimal number of preparation steps and require a minimum or preparation time by the user. An additional object of the invention is to design such devices to have a cost of production low enough to allow economic single use, thereby allowing such devices to be used freely without regard to excessive cost in clinical research as well as in human and veterinary clinical diagnostic applications. Such pre-cleaned devices would offer the users improved uniformity and reliability because the results would not be dependent upon previous usage conditions, cleaning procedures, or worn status of the analytical device, etc. Also the user would be provided the convenience of no longer having to carry out tedious manual cleaning operations on the device prior to usage.

Additionally we present electrophoretic devices and methods for improved sample preparation prior to MALDI-mass spectrographic (MALDI-MS) analysis. The devices and methods for their use provide for analyte dissociation, electrophoretic separation, concentration, and trapping on a MALDI-compatible capture layer. Advantageously the capture layer is in the form of a slide having an attached slide frame that incorporates an attachment means for removabley attaching the capture directly to a MALDI matrix sample plate adaptable to a mass spectrometer. The slide provides for rapid introduction of samples into a mass spectrometer and allows such analyses to performed in an automated fashion. Thereby the slide device provides for higher throughput and reduced cost per sample analysis. These devices and methods provide an improved system for the rapid and efficient preparation, separation, concentration and formatting of samples for chemical analysis. This aspect of the invention is particularly suitable for preparation of biological samples prior to mass spectrographic analysis. Taken together, the devices and methods are general and provide for embodiments that can be used to concentrate either singly-charged anions or cations or multiply-charged polyanions or polycations such a peptides, polypeptides, oligopeptides or proteins. Further the methods may also be used for charged carbohydrates, glycoproteins, DNA, RNA, or any other charged metabolic intermediate.

Electrically neutral molecules (i.e. molecules bearing no intrinsic charge) also may be analyzed by using the electrophoretic devices and methods disclosed herein by providing for either a.) electrophoretically-induced electro-osmotic flow (EOF) which occurs when the porous solid phase through which the current is passed carries a net electrical charge and mobile counterions induce the flow of surrounding solvent, or b) by providing charged micelles (or charged particles) into (or onto) which the neutral analytes partition. The general mechanism for the latter type of separation (usually performed in capillaries) is generally known as micellar electrokinetic capillary chromatography (MECC). These methods may be used in combination with the presently disclosed devices and methods for the analysis of various types of molecules without a net electrical charge. Such neutral molecules may include those without ionizable groups, molecules such as polypeptides or proteins maintained at a pH near their isoelectric point, zitterionic species, or other types of electrically neutral molecules.

The instant invention may be used to concentrate either hydrophobic or hydrophilic molecules. The concentration results in a porous membrane having an analyte captured to one or more predetermined, discrete, locations by a focused electrical field and wherein the porous capture membrane is adapted to fit on a MALDI mass spectrometer sample plate for analysis of the analytes. In order to aid in ionization of captured samples, a MALDI matrix material is applied to the discrete locations prior to introduction of the porous membrane in a MALDI mass spectrometer. The concentration and capture device with the incorporated porous capture membrane is used according to the methods described below so as to be broadly applicable to a vast range of biological molecules for improved sample preparation prior to MALDI-mass spectrographic (MALDI-MS) analysis.

BRIEF DESCRIPTION OF THE DRAWINGS

FIG. 4a. Expanded Side View of a Cylindrical Sample Well.
FIG. 4b. Expanded Top View of a Cylindrical Sample Well.

DETAILED DESCRIPTION OF THE INVENTION

One aspect of this invention is a device and methods for separation concentration and capture of multiple samples of charged analytes by focusing in an electrical field. The devices and methods include one or more of the elements and/or steps described below.

Figure 1:
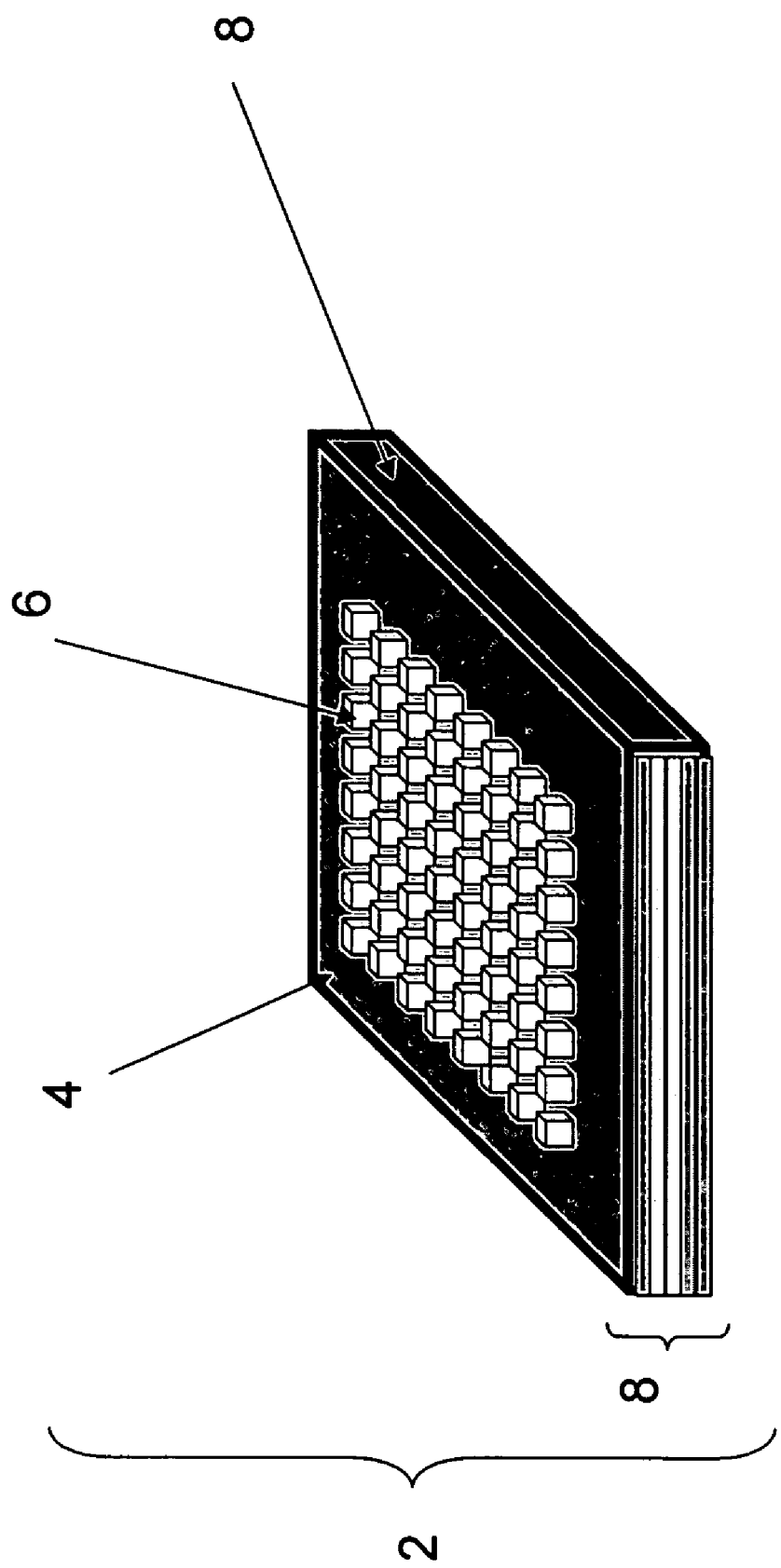
FIG. 1. Perspective View of Concentrator Device.
Figure 3:
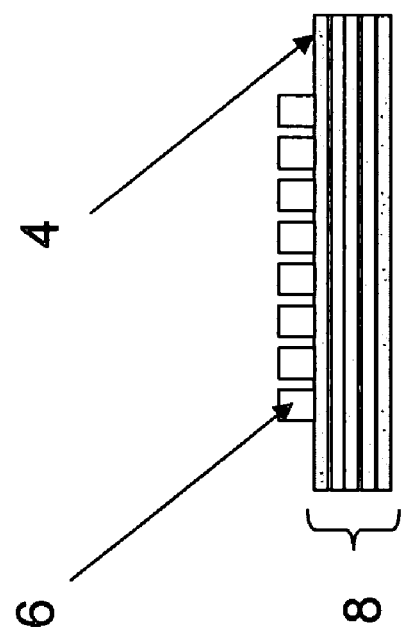
FIG. 3. Side View of Concentrator Device.
Figure 2:
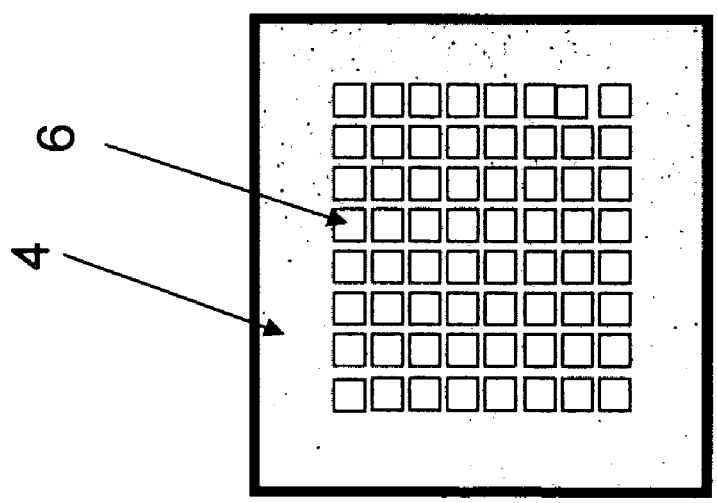
FIG. 2. Top View of Concentrator Device.

A. Wells for Retaining Multiple Samples:

FIGS. 1, 2 and 3 show perspective, top and side views, respectively of a concentrator device. The device is a multi-well sample-retaining system that is useful for simultaneously preparing one or more samples for mass spectrographic analysis. The figures show the basic functional components of the device. The device 2 has sample wells 6 disposed in the top surface 4 of the device. Although the device can have various shapes generally it will be rectangular as viewed from the top surface 4 and have dimensions between 0.5 cm and 50 cm on a side. More usually the device will have dimensions of between 2 cm and 15 cm on a side. The device can have between 1 and 1000 sample wells, or more, but more usually will have from 10-100 wells depending on the sample throughput and availability of equipment for automated dispensing of the samples into the sample wells. The wells also can be of various shapes such as cylindrical, cubic, rhomboid, having any cross-sectional shape, e.g. square, hexagonal, pentagonal, etc. The diameter, or width, of the wells will generally be between 1 mm and 1 cm. Similarly the depth of the wells will be between 1 mm and 2 cm. More usually the wells will be between 2 mm and 10 mm in depth.

FIGS. 4a and 4b show expanded side and top views of a sample well. Each well has sidewalls 12, a top opening 14, and a bottom surface 16. The sidewalls are made of a nonporous material that retain aqueous liquid samples and have inner surfaces 20 and outer surfaces 22. When retained by the wells the aqueous samples contact at least a portion of the inner surfaces 20 of the sidewalls 12. The aqueous samples typically are from biological sources, for example, blood, plasma, serum, urine, cerebrospinal fluid, cell-extracts, or the like. The wells serve to contain the liquid samples and allow them to be placed into the wells during the analysis procedure. Each well serves to retain analytes from the liquid sample for subsequent purification and separation (and concentration) from nonanalyte materials that may be present in the sample. Generally the side-walls 12 will be between 1 mm and 1 cm in height. Thus the wells will generally retain between 1 μl (microliter) and 3 ml (milliliter) volume of liquid sample. The device can be proportionately scaled either larger, or smaller, having side and bottom dimensions between 0.1 mm and 10 cm, if required, for handling larger or smaller samples, respectively. The side-walls 12 and top surface 4 of the device usually will be formed from nonporous material. The nonporous material may be a ceramic or a metal, such as stainless steel, anodized aluminum, brass, or the like. Usually the nonporous material will be a polymeric material, such as polycarbonate, polyethylene, polypropylene, polystyrene, polyimide, nylon, rayon, fluorocarbon, perfluorocarbon, polydimethylsioloxane, polyester, acrylics, acrylonitrile-butadiene-styrene; polyoxy-methylene; polyarylate, polyvinylchloride, PBT-Polyester, polybenzimidazone, acetal copolymers, polyimides, ethylene-chlorotrifluorethylene, PET polyesters, ethylene-tetrafluorethylene, fluorinated ethylene propylene, polyethylene, polyurathanes, polyketones, polychloro-trifluoro-ethylene, polyethylene terephthalate polyesters, polypropylene oxides, polypropylene styrenes, polyether-ether ketones, polyarylether sulfones, polyamide-imides, polyarylates, polymethylpentene, polyketones, polysulfones, PBT polyesters, and/or alloys of polymers. Additional materials that may be used to fabricate the concentrator device include acrylics, e.g., LUCITE® or Plexiglas; acrylonitrile-butadiene-styrene (ABS); polyoxymethylene (Acetal); polyarylate (ARDEL®); polyvinylchloride (PVC); PBT-Polyester (CELANEX®); polybenzimidazone (Celazole®); the acetal copolymers Celcon, or Delrin®; polyimides, e.g., Duratron® or Kapton®; ethylene-chlorotrifluoroethylene, e.g. Halar®; PET polyesters, e.g. Ertalyte®; ethylene-tetrafluorethylene, e.g. Tefzel®; fluorinated ethylene propylene (FEP); polyethylene; polyurathanes, e.g., Isoplast®; polyketones, e.g. Kadel®; polychloro-trifluoro-ethylene (Kel-F®); polyvinylidene fluoride (PVDF); polyethylene terephthalate polyesters, e.g, Mylar®; polypropylene oxides and styrenes, e.g. Noryl®; polyether-ether ketones, e.g. PEEK™; polytetrafluorethylene (Teflon®); polyarylether sulfones, e.g. Radel®; polyamide-imides, e.g. Torlon®; polyphenylene sulfides, e.g. Techtron® or Ryton®; polyarylates, e.g. Ardel®; polymethylpentene (TPX®); polyketones, e.g. Kadel®; polysulfones, e.g. Udel®; PBT polyesters, e.g. Valox®.

B. Layers for Separation of Analytes from Interfering Species

Figure 5:
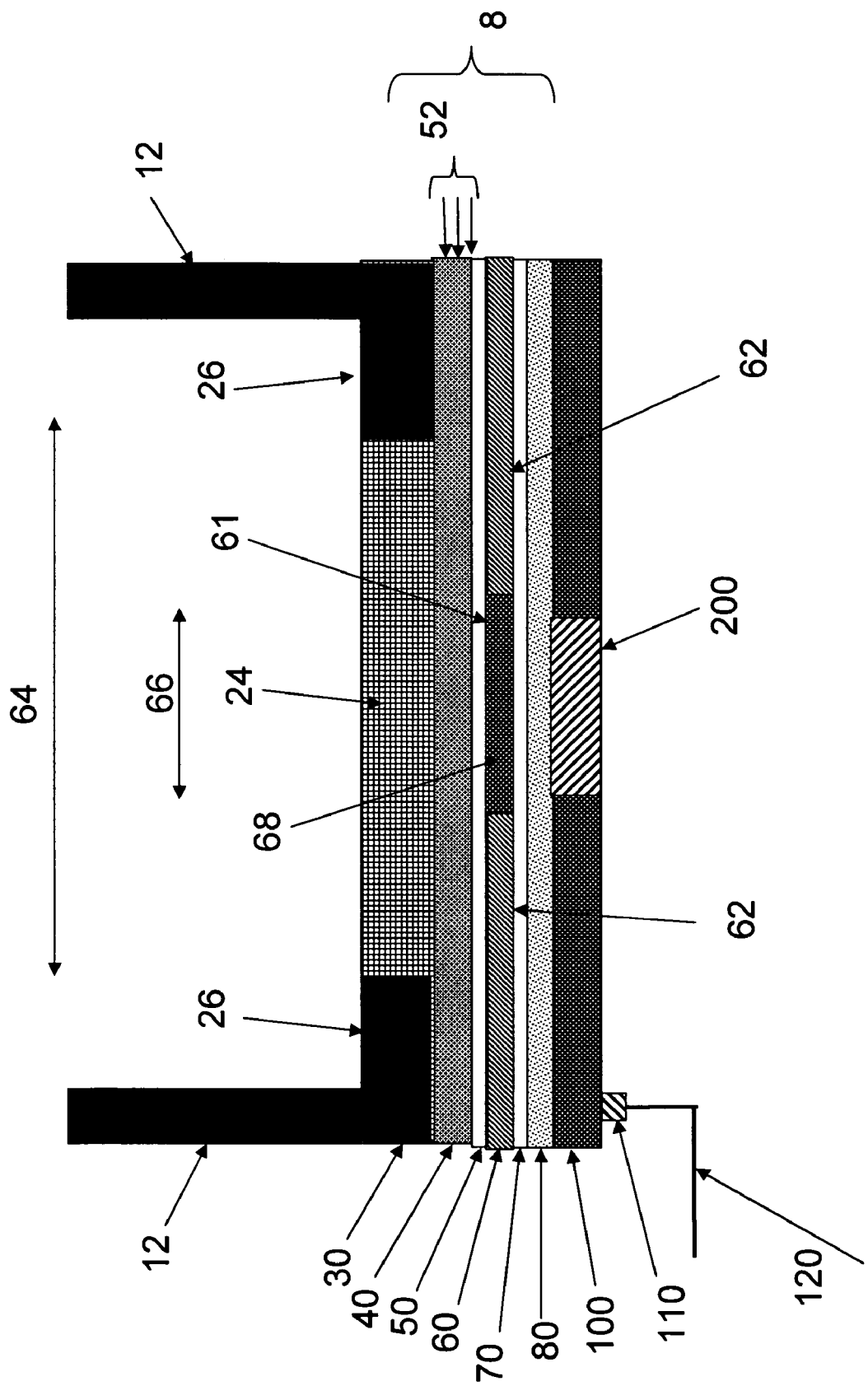
FIG. 5. Expanded View of a Single Well and Porous Layers in Contact with Photoresponsive Electrode.

Disposed within or under the sample wells are two or more porous layers 8 for the separation, concentration, retention and binding of analytes for sensitive analysis, for example by mass spectroscopy. FIG. 5 shows an expanded view, in cross section, of an example construction of the two, or more, porous layers 8. The well bottom surface may be entirely or partially porous by partial or compete exposure to the porous layers 8. Where only a portion of the well bottom is porous, generally the well bottoms will have porous regions 24 and nonporous regions 26. The nonporous regions may be used advantageously to facilitate construction, such as to increase the strength of the materials used in layers 8, or alternatively to aid in forming a seal between side-walls 12 and the porous layers 8.

A first porous absorptive layer 30 customarily will be a liquid absorptive layer to absorb liquid samples added to the wells 6. For example, liquid samples may be placed into the wells by pipet or other sample dispensing means and absorbed into layer 30. Thereafter conductive liquid electrolyte, buffered in it pH, may be placed over the absorbed sample without substantially diluting the sample. Thereby the sample is retained substantially undiluted in close proximity to the porous layers 8. The absorptive layer 30 usually will be a bibulous polymeric fibrous or particulate material insoluble in aqueous solvents, such as cotton or glass fiber, paper or synthetic fabric or particles. The fabric or particles can be made of numerous varieties of cellulose, nitrocellulose, cellulose ester, glass fiber, nylon, rayon, fluorocarbon, perfluorocarbon, polydimethylsioloxane, polyester, acrylic, acrylonitrile-butadiene-styrene; polyoxy-methylene; polyarylate, polyvinylchloride, PBT-Polyester, polybenzimidazone acetal copolymers, polyimides, ethylene-chlorotrifluorethylenes, PET polyesters, ethylene-tetrafluorethylenes, fluorinated ethylene propylenes, polyethylenes, polyurathanes, polyketones, polychloro-trifluoro-ethylene, polyethylene terephthalate etc. The major requirements for layer 30 are a) it must be absorptive to aqueous samples and porous to analytes of interest. A preferred absorptive layer 30 is made of Sephadex particles (Pharmacia-Amersham). For example, such Sephadex particles may be G-50-Course retained at the top surface of the layer 40 by a fine Nylon mesh having mesh openings between 20 and 100 microns in diameter (i.e. smaller than the 100-300 micron diameter of the Sephadex particles). The volume of Sephadex used may be adjusted for any desired sample volume. Usually, however the volume will be between 5 and 100 microliters.

A chromatographic separation layer 40 comprises a second porous layer. Layer 40 is differentially porous to analytes of interest that are placed into wells 6 during operation of the device. Such analytes may be proteins, polypeptides or peptides that migrate at different rates through layer 40 by virtue of having different molecular size, different electrical charge, different hydrophobicity, or different affinity for the separation layer 40. Thus such analytes pass from the sample wells 6, through separation layer 40, and into an underlying capture layer 60 at different rates. Customarily layer 40 is comprised of one, or more, separation media that facilitate the separation of high mass (i.e. molecular weight) sample constituents from those of lower in molecular weight. In this case, the velocity of high mass sample constituents moving through layer 40 is retarded relative to lower molecular weight sample constituents. For example, layer 40 may be comprised of a molecular sieve, such as dialysis membrane. Such dialysis membranes are well known to those skilled in the art clinical dialysis or in handling and purification of proteins. Customarily such dialysis membranes are comprised of materials such as cellulose, cellulose acetate, polyester, etc. One problem with the use of such membranes is that they become fouled when overloaded with large molecular weight (retained molecules). Severe fouling due to overloading can be prevented by providing a means for convection (flow) to remove retained molecules from the membrane surface. Such flow may be driven by gravity, hydrostatic pressure, magnetic stir bars, etc. Preferably, however, a first separation medium of layer 40 will be formed from a porous gelatinous substance, such as agarose, or more optimally, polyacrylamide. Such gels are well known to those skilled in the art of macromolecule separations to retard the velocity of large size molecules relative to lower size molecules, without fouling, when charged macromolecules (such as DNA, RNA, or proteins) are placed in an electrical field. Thus such gels are well known to provide for electrophoretic separation of a very large range of sizes of biological macromolecules. Another advantage of such gels is that they can handle much larger quantities of sample analytes during electrophoretic separation without overloading. That is, such gelatinous substances are well known to have the capacity to sieve by electrophoresis high molecular proteins, DNA, RNA, or other biological polymers driven by an electrical field without becoming fouled or clogged. Examples of such gels, well know to those skilled in the art of protein or polynucleotide separations, is polyacrylamide or agarose. The sieving properties of such media can be changed by adjusting the pore size. The pore size of polyacrylamide, for example, can be altered by changing either the concentration of acrylamide monomer (or the concentration of bis-acrylamide crosslinker).

Separation layer 40 may be comprised of multiple sublayers 52 to aid in the separation of biological macromolecules. A second, third, fourth, or more separation media may be employed in combination, either serially or mixed together within the first separation medium. For example, multiple sublayers of separation media may be comprised of different pore sizes or a gradient of pore sizes (in each case increasing in pore size from top to bottom) to further prevent clogging of the porous separation layer 40. The very top surface might be comprised of 2.5% acrylamide, an intermediate layer comprised of 5% acrylamide and a lower layer comprised of 7.5% acrylamide, for example. Alternatively the sublayers 52 may be formed of materials that bind and remove specific substances, such as albumin or IgG in blood, blood plasma or serum. Specific removal of such substances may be selective adsorption by the principles of affinity chromatography. For example, proteins, carbohydrates or polynucleotides may be removed selectively by antibodies, lectins, or oligonucleotides bound to matrices such as cellulose, dextrins, acrylamide, polymeric resins, or the like. Other means of selectively removing analytes include chelation of proteins to metals (such as zinc or nickel) biotin-avidin interaction, hydrophobic dye-albumin binding, etc. as is well known in the art of constructing affinity matrices.

C. Layers for Concentration and Capture of Analytes for Chemical Analysis

A third porous focusing layer 50 optionally may be disposed under layer 40 as a focusing layer. Layer 50 is comprised of materials that offer high mobility to analytes that are being focused into underlying capture region 68 of capture layer 60. Example materials for focusing layer 50 are highly permeable agarose, cellulose (e.g. Whatman #1 or Whatman #2 filter paper, or the like). The solid portions of such materials have large pores but still advantageously prevent convection within focusing layer 50. When used, focusing layer 50 will be sufficiently thick to prevent both diffusive and convective transport of analytes from the separation layer 40 to underlying capture layer 60. Usually the thickness will be from 200 and 3000 microns. Focusing layer 50 assists in focusing (i.e. concentrating) analytes in a plane parallel to porous layers 8. The concentration occurs once the analytes of interest have passed through the highly resistive separation layer 40 but prior to their entry into capture layer 60. Focusing layer 40 is optional but when present assists in achieving the desired focusing of analytes into the capture region 68 of capture layer 60.

Disposed under separation layer 40 and the optional focusing layer 50 is analyte capture layer 60. Capture layer 60 also is porous in order to allow ionic electrical current to pass through. The pore size of a membrane, for example, employed as the porous capture layer 60 will ordinarily be small enough to optimize the efficiency of capture and thus depend upon the mechanism of capture. The mechanism of capture may simply be filtration sieving in which case the pores size will be smaller that the analyte of interest. For capture of small proteins and oligopeptides by sieving, the pore size must be quite small, on the order of 10-100 angstroms. The pore diameters may be either smaller or larger than the analytes of interest. Where the pores in capture layer 60 are larger than the analytes of interest, capture layer 60 must have an affinity for the analytes of interest as described below.

The capture layer 60 usually may be a membrane between 1 micron and 1000 microns in thickness. Usually the thickness will be between 10 microns and 200 microns. Capture of the analytes of interest in a thin layer facilitates subsequent extraction of the analytes for MALDI-MS analysis. Also, a thin capture layer 60, relative to the well depth 18, results in concentration of analytes in proportion to the ratio thereof. The thickness of capture layer 60, however, must be sufficient to give the membrane adequate mechanical strength and adequate binding capacity.

For a typical separation and capture procedure the electrical field applied will range from 5-100 volts/cm. Typically the voltage will be about 5 volts (generally ranging from about 3 volts to about 10 volts) and the separation distance between anode and cathode is about 0.4 cm (generally ranging from 0.005 cm to about 5 cm). The electrophoretic velocity v is given as $$v = \mu E \qquad \text{(Eq. 1)}$$

where $\mu$ is the electrophoretic mobility of an analyte molecule and E is the electrical field strength. The value of $\mu$ is calculated directly from its diffusion coefficient D from the Einstein relation $$D = (kT/q)\mu \qquad \text{(Eq. 2)}$$

The diffusion coefficient for amino acids and similarly-sized molecules is about $10^{-5}$ cm$^2$/sec at about room temperature. From the value of $(kT/q) \approx 0.0259$ volts at room temperature for singly-charged molecules, we find that the value of $\mu$ for these molecules is about $4 \times 10^{-4}$ cm$^2$/(V·sec). Therefore, from Eq. 1 the velocity of such molecules traversing the membrane in an electrical field of about 20 volts/cm will be: (20 volts/cm) $4 \times 10^{-4}$ cm$^2$/(V·sec)=$8 \times 10^{-3}$ cm/sec (i.e. about 80 microns/sec).

We immediately see that if the membrane is about 80 microns thick the transit time will be about 1 second. For higher electrical fields, higher electrophoretic mobilities, or thinner membranes, the transit times will be proportionately shorter (and conversely for lower electrical fields, lower electrophoretic mobilities, or thicker membranes proportionately longer). For the instant invention the transit time across the membrane (in the absence of binding affinity between the analyte and membrane) will usually be between 0.1 and 100 seconds.

Preferably the mechanism of capture by layer 60 will be based upon binding of the analytes to layer 60 rather than by sieving alone. When sufficient binding occurs, capture by sieving is no longer required. Upon binding to the capture membrane 60 the transit time of analytes across layer 60 increases dramatically (i.e., inversely in proportion to the fraction of time the traversing molecule spends in the free state). For example if, on average, the molecules spend 99.99% of the time bound (i.e. 0.01% of the time free) the transit time will increase by a factor of $10^4$. That is, where the transit time in the absence of binding was 1 second, where the analyte is bound 99.99% of the time, the transit time becomes about 10,000 seconds. In general, the transit time across the membrane (in the presence of binding of binding to capture layer 60) will be between 10 and $10^6$ seconds.

Capture by binding offers at least two advantages over capture by sieving, namely, a) the pore sizes can be much larger than for sieving and b) the capture layer 60 can be a membrane that may be washed free of contaminants after capture of analyte molecules. By using affinity capture, the membrane pores can be much larger than the diameter of hydrated ions present in biological samples (e.g. sodium, potassium, calcium and chloride). For efficient capture by binding, the pores must only be smaller than a diffusion distance x of analyte molecules passing through the membrane in transit time t. As discussed above, typically t will be from 0.1 to 1000 milliseconds and d between $10^{-5}$ and $10^{-7}$ cm$^2$/sec. Using the expression for diffusion in 3 dimensions $$x^2 = 6Dt \quad \text{(Eq. 3)}$$

for efficient capture of small protein molecules (that have diffusion coefficients of about $10^{-6}$ cm$^2$/sec) even with the fastest transit times specified above (i.e., 0.1 millisecond) we find that the pore diameter x may be up to 8000 angstroms (or almost 1 micron). In contrast, for capture by the sieving process, the pore size would have to be many times smaller (i.e., about 15-40 angstroms) in order to remove small analytes with a molecular weight of 1000-60,000. Therefore affinity capture allows a wide variety of pore sizes to be utilized roughly ranging from 10 angstroms to about 1 micron for very high electrophoretic velocities (or with thin membranes). Correspondingly slower electrophoretic velocities or thicker membranes would allow the pore sizes to be correspondingly larger still (e.g. ranging from 10 angstroms to 10 microns, or larger).

Such capture may be by any binding mechanism. For example peptides oligopeptides and proteins have amino acids with hydrophobic side chains. Thus hydrophobic surfaces and porous hydrophobic membranes tend to bind such molecules with moderately high affinity. Thus porous membrane materials such as ethylene-tetrafluorethylene, e.g. Tefzel®; fluorinated ethylene propylene (FEP); polyethylene; polychloro-trifluoro-ethylene (Kel-F®); polyvinylidene fluoride (PVDF); styrenes, e.g. Noryl®; polytetrafluoroethylene (Teflon®) porous Teflon, or the like work well to bind peptide and protein analytes. Preferably thin PVDF dialysis membranes with about 250,000 molecular weight cutoff (obtained from Spectrum Laboratories; Rancho Dominguez, Calif.) are used to capture such peptides. Alternatively, porous capture membranes made of nitrocellulose, nylon, rayon, polyester, or the like, each having an inherent affinity for proteins and peptides may be used as a capture membrane in such molecules. Alternatively, capture layer 60 may be made of thin membranous materials such as of nitrocellulose, cellulose, nylon, rayon, polyester, porous PVDF, or the like.

Capture layer 60 may be a polypeptide binding layer, either made of such materials that bind polypeptides or derivatized to become polypeptide binding. Conveniently, the entire layer 60 can be made of the same material. Alternatively layer 60 may have isolated polypeptide binding regions or islands. In such a way the analytes may be concentrated and bound to layer 60 and then washed, either with distilled, or purified water, or an aqueous buffer of predetermined pH and ionic strength, such as ammonium carbonate buffer. By washing the surfaces that have bound analyte, impurities, such as salts, or detergents, that may be in the samples are removed. Thereby interference or suppression of MALDI signals from the analyte will be substantially reduced so as to substantially increase the sensitivity of detection of analyte molecules.

For capture of polypeptides, capture layer 60 generally will be comprised of a thin, finely porous material such as dialysis membrane made of a protein-binding material such as polyvinolydine difluoride (PVDF). The porous material of layer 60 must withstand aqueous or organic solvents such as aqueous buffers and electrolytes, methanol, ethanol, and acetonitrile, all of which frequently are used with MALDI-MS samples and MALDI matrices. In order to bind polypeptides and proteins layer 60 generally will be hydrophobic. The hydrophobicity may be contributed either by alkyl or aryl organic groups, either naturally present on the polymer or alternatively chemically-attached to the surface, as is well know in the prior art. Alternatively the hydrophobic character may be contributed by chloro- or fluorocarbons such as ethylene-chlorotrifluorethylene, perfluorocarbons such as polychloro-trifluoro-ethylene, ethylene-tetrafluorethylene, fluorinated ethylene propylene, polychloro-trifluoro-ethylene (Kel-F®); polyvinylidene fluoride (PVDF); polytetrafluorethylene (Teflon®) ethylene-tetrafluorethylene, e.g. Tefzel®; fluorinated ethylene propylene (FEP); etc. The porosity of the dialysis membrane may be selected to also allow selective trapping by molecular size rather than by hydrophobicity alone. For example a 5,000 molecular wt. hydrophobic dialysis membrane could be used to selectively retain all molecular species larger than 5,000 molecular weight. Washing the membrane with an elution solution containing either a detergent such as octylglucoside, Triton X-100, NP-40, or the like, or alternatively an organic solvent such as ethanol, methanol, acetonitrile, ethylacetate, or the like could then be used to elute smaller molecular weight analytes from the membrane. The elution solution is then removed and the proteins are allowed to bind to the capture membrane via hydrophobic interaction.

The material comprising capture layer 60 may be another polymeric protein binding material, such as polydimethylsiloxane, polyester, acrylics, acrylonitrile-butadiene-styrene; polyoxy-methylene; polyarylate, polyvinylchloride, PBT-Polyester, polybenzimidazone, PET polyesters, polyethylene, polyurethanes, polyethylene terephthalate polyesters, polypropylene oxides, polypropylene styrenes, polyetherether ketones, polyarylether polyarylates, polymethylpentene, PBT polyesters, and/or alloys of polymers. Additional materials that may be used to fabricate the concentrator device include acrylics, e.g., LUCITE® or Plexiglas; acrylonitrile-butadiene-styrene (ABS); polyoxy-methylene (Acetal); polyarylate (ARDEL®); polyvinylchloride (PVC); PBT-Polyester (CELANEX®); polybenzimidazone (Celazole®); the acetal copolymers Celcon, or Delrin®; polyimides, e.g., Duratron® or Kapton®; e.g. Halar®; PET polyesters, e.g. Ertalyte®; polyethylene; polyurathanes, e.g., Isoplast®; polyketones, e.g. Kadel®; polyethylene terephthalate polyesters, e.g, Mylar®; polypropylene oxides and styrenes, e.g. Noryl®; polyether-ether ketones, e.g. PEEK™; polyarylether sulfones, e.g. Radel®; polyamide-imides, e.g. Torlon®; polyphenylene sulfides, e.g. Techtron®; polyarylates, e.g. Ardel®; polymethylpentene (TPX®); polyketones, e.g. Kadel®; polysulfones, e.g. Udel®; polyphenylene sulfides, e.g. Ryton®; PBT polyesters, e.g. Valox®; membranes formed from alloys of polymers, e.g. Xenoy®; or laminates of two or more polymer membranes.

The porous capture layer 60 has a marker location that is readable by a mass spectrometer and where at least one predetermined locations are a known distance from the marker location. The predetermine locations correspond to the capture region, the region of the capture layer at which the desired molecules have been concentrate. The marker location may be a black opaque area. The device 2 serves to focus electrophoretic current through capture region 68 of capture membrane 60 in preference to noncapture regions 62. This results in concentration of selected analytes within region 68 upon capture. The amount of concentration achieved is inversely proportional to the area of region 68, (the cross-section of which is shown by line 66) in relation to the cross-sectional area of an entire sample well, 6, above the capture membrane 60. The cross-section of a well is shown by line 64. Thus the concentration achieved is proportional to the square of the length of line 64 divided by the square of the length of line 66. Capture of the concentrated analytes by capture layer 60 facilitates their subsequent placement, in concentrated form, onto a MALDI target plate permitting extraction there-from in the concentrated form. The size of the sample concentration regions generally will be between 1 to 1000 microns in diameter. More usually the diameter of the concentration regions will be between 50 and 200 microns in diameter.

Disposed under layer capture layer 60 optionally is a barrier layer 70 that functions to prevent analytes of interest from escaping should the analytes pass though capture layer 60. Similar to layer 30, 40, 50, and 60, layer 70 is porous. The pore size of layer 70, however, is sufficiently small to prevent all selected analytes of interest from passing through layer 70. Barrier layer 70 may be any suitable dialysis membrane with a suitably low cut off molecular wt. For example, CEA dialysis membrane available from Spectrum Laboratories, Inc. having a cutoff molecular weight of about 500 functions well with a PVDF capture membrane 40 to retain peptides of interest that may be present in human plasma or serum. Any suitable dialysis membrane, or other membrane with suitably small pores may be used for the purpose of the barrier layer. Barrier layer 70, however, is not required when analytes are captured at the topside 61 of layer 60, for example by sieving.

Likewise, disposed under capture layer 60 and barrier layer 70 optionally is buffering layer 80. The buffering layer either may be solid, liquid, or a combination thereof. For example the buffering layer may be a liquid solution of concentrated buffering medium, such as 250 mM aqueous histidine. Optimally this buffer will be at a pH near the isoelectric point of the buffering species, approximately 7.5-8.0 for histidine. Thereby the buffer capacity can be very high with minimal ionic conductivity. Also, saturated solutions of aspartic acid or glutamic acid, or other zwitterionic buffers can be used to similarly buffer isoelectrically in the pH region of 2.5-3.0. Alternatively such buffers may be incorporated into an aqueous gel or sol-gel comprised of materials such as agarose or polyacrylamide.

The porous layers 8 may include all or only several of the layers, 30, 40, 50, 60, 70 and 80. Separation layer 40 and capture layer 60 are required for operation of the device whereas layers 30, 50, 70 and 80 are optional. These optional porous layers, however, provide for improved performance in the device including either more robust operation, faster separation, more complete capture, or improved pH stability or a combination thereof.

D. Electrodes for Application of a Focused Electric Field:

At the bottom surface of the porous layers 8 is bottom electrode 100 to supply an electronic current that produces an ionic current within the porous layers 8. All of the layers, 8, including layers 30, 40, 50, 60, 70 and 80 will be porous to ions in electrolyte samples thereby allowing ionic currents to be substantially focused through region 68 of capture membrane 60 while electrophoretically attracting analytes of interest toward electrode 100.

Figure 6:
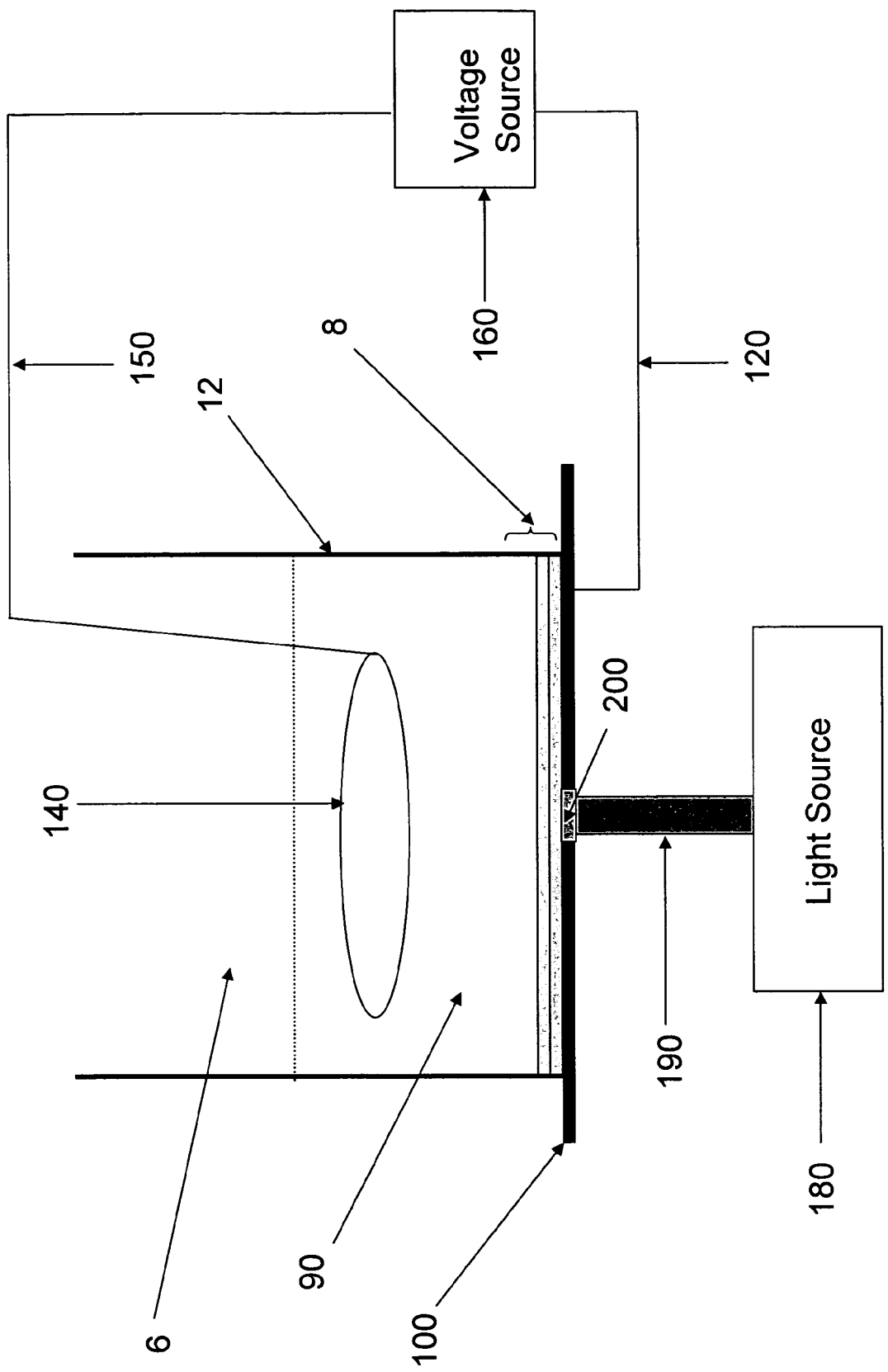
FIG. 6. View of a single well with analyte sample and porous membranes Top and bottom electrodes are connected to a voltage source.

FIG. 6 shows a schematic diagram of a single sample well 6 containing a sample analyte in conductive ionic liquid electrolyte 90. Immersed in the sample electrolyte 90 is a top electrode 140 serving as a counter electrode that is connected to lead 150. Lead 150 in turn is connected to voltage source 160 that is also connected to lead 120 that is connected to a bottom electrode 100 (via conductive contact 110, as shown in FIG. 5). The voltage source biases the top electrode 140 with an electrical potential versus the bottom electrode 100. Thereby components 6, 8, 12, 90, 100, 120, 140, 150 and 160 cooperatively interact to form an electrolytic cell capable of carrying out electrophoretic separations. The voltage bias may be predetermined, as with a potentiostat, either fixed in value or programmed to vary with time. Alternatively the voltage source may be a galvanostat where the current through the electrolytic cell is predetermined, or fixed. In a preferred mode of operation the voltage source is a galvanostat and the cell is operated in the galvanostat mode with the current selected to be in the range of 100 microamps to 10 milliamps. More usually the current will be about 400 microamps to 1 milliamp. With the value of current predetermined, the voltage will range from about 1 volt to 100 volts. More usually the voltage will be between 2.0 volts and 20 volts.

Preferably the bottom electrode will be a photoconductive electrode that allows the current path within the electrode to be confined to within photoconductive region 200 of electrode 100. The photoconductive material may be a semiconductor such as doped silicon or germanium, gallium arsenide, titanium dioxide, tungsten oxide, or the like. These photoresponsive materials may be in the single crystal form, or may be polycrystalline, i.e. present as multiple, small crystallites. Alternatively, a photoresponsive bottom 100 electrode may be present as a film of amorphous material. Such a film may be deposited as a thin film either by evaporation or sputtering, for example. Preferably the semi-conductive material will be a thick film, made of $TiO_2$ or similar semi-conductive material, deposited by an inexpensive screen-printing technique. Methods of manufacturing both thin and thick film photoresponsive materials are well known in the prior art.

Illumination of a photoresponsive electrode from light source 180 with focused or collimated light beam 190 results in the creation of a photoconductive region 200. Region 200 includes the illuminated regions of electrode 100 plus a minority carrier diffusion distance d surrounding each illuminated region. Distance d can be substantial such on the order of 1 mm, or more for materials such as pure, single crystal germanium. Distance d can be on the order of 100-500 microns in pure single crystal silicon or made to be less than 100 microns, even less than 1 micron, by suitably doping the single crystal semiconductors with materials that reduce minority-carrier lifetime. Such materials, or "lifetime killers" may be metals such as gold, iron, copper, or the like, as is well known in the prior art. Thus substantial control can be exercised over the dimensions of photoconductive region 200. The light beam usually will be between 0.001 and 1 mm in diameter. By the use of a small focused light source, such as a laser, or other light source directed through an aperture or a focusing lens. The width of the light beam can be 1-100 microns, or less, resulting in a very small conductive region 200 of from 1-500 microns in diameter, or less.

A single continuous semi-conductive electrode may be used as a phoresponsive electrode to create an array of a multiplicity of electrolytic cells having two, or more, photoconductive regions, 200 (see for example FIGS. 1, 2 and 3). The photoresponsive electrode 100 may have one, or more leads 120 connected to voltage source 160 in order to apply a voltage bias to photoresponsive electrode 100 with respect to top electrode 140. Where two, or more, electrolytic cells are in contact with a single photoresponsive electrode, photocurrent through each one of the two or more electrolytic cells is controlled separately by controlling the intensity of light directed to each photoconductive region 200 on photoresponsive electrode 100. Thereby current through each of the two, or more electrolytic cells can be controlled independently by controlling the intensity of light within light beam 190. For example, the electrolytic cells may individually operated in the galvanostatic mode by applying a single predetermined bias voltage between electrodes 140 and 100, but separately monitoring the current through each electrolytic cells and separately supplying a feedback signal to the light source providing a light beam to each electrolytic cell in order to maintain the current through each electrolytic cell at a predetermined value. Controlling of the illumination light intensity therefore can be used to provide for operation of each electrolytic cell in the a galvanostatic mode. In a preferred mode of operation the voltage source is a galvanostat and with the current selected to be in the range of 100 microamps to 10 milliamps. More usually the current will be about 400 microamps to 1 milliamp. With the value of current predetermined, the voltage will range from about 1 volt to 100 volts. More usually the voltage will be between 2.0 volts and 20 volts.

The top electrode 140 serves as a counter electrode and need not be photoresponsive. Top electrode 140 preferably will be made of insert material such as platinum, gold, palladium, or the like. The top electrode also can be made of less expensive materials, such as stainless steel, titanium, chromium, or the like. Virtually any electronically conductive material may be used for the top electrode provided that the electrode material does not undergo corrosion or dissolve in the aqueous sample. In order to minimize cost while maximizing corrosion resistance, top electrode 140 may have the inert material plated onto less expensive materials, such as iron, copper titanium, tungsten, brass, or the like. Also the counter electrode can be made of conductive carbonaceous materials such as carbon, graphite, or the like. The carbonaceous material advantageously can be screen-printed onto a nonconductive polymer so that the top electrode can be fabricated inexpensively into a conductive pattern.

The present invention serves as a rapid system to prepare and separate desired analytes such as proteins, polypeptides and peptide molecules from interfering salts, lipids, sugars, etc, that are present in complex biological samples, such as blood plasma, serum, cerebrospinal fluid, etc. The separated analytes are then concentrated in the "Z" dimension by capture onto capture layer 60, e.g. a thin membrane. The analytes also are concentrated in the "X" and "Y" dimensions, i.e. within the plane of capture layer 60 into small capture regions 68 by means of focusing an electrical field within individual sample electrolyte cells through capture regions 68.

Figure 7:
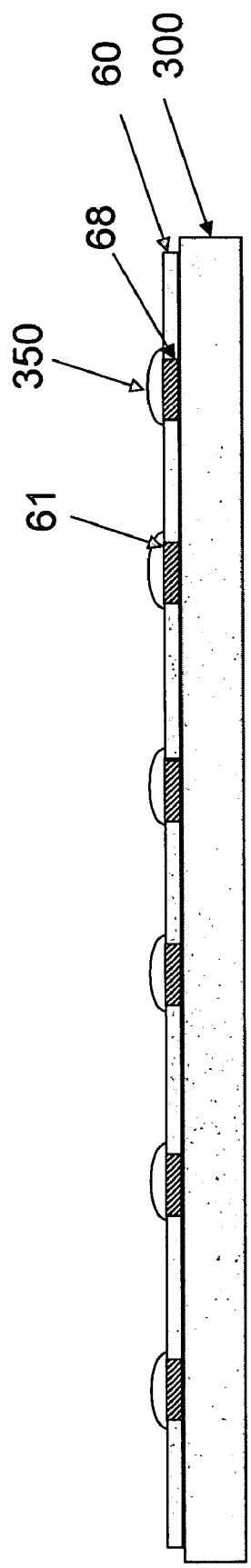
FIG. 7. Side view of a capture membrane (with an array of analyte capture sites) affixed to a MALDI sample plate with MALDI matrix applied in a solvent to each of the analyte capture sites.

E. Capture Slide Having an Array of Capture Sites Providing for Removable Attachment to a MALDI Target Plate for Analysis by MALDI Mass Spectrometry:

In order to provide for matrix-assisted laser desorption ionization (MALDI) after separation and concentration of sample analytes into region 68 of capture layer 60, capture layer 60 is separated from the other porous layers and the capture layer 60 is affixed to a suitable MALDI mass spectrometry sample plate 300 for introduction into a mass spectrometer as shown in FIG. 7. A suitable MALDI matrix dissolved in a suitable matrix solvent then is added as a small droplet 350 to analyte capture regions 68 of the capture layer. The solvent is allowed to dissolve the analytes present and as the solvent evaporates the analytes become incorporated within MALDI matrix crystals which form on the top surface 61 of capture layer 60. As is well known to those skilled in the art of MALDI mass spectrometry, the matrix material is generally an organic acid that absorbs energy strongly in the region of the electromagnetic spectrum (e.g. 337 nanometers) that is provided by a UV laser (e.g. a pulsed nitrogen laser). Generally MALDI matrix will be added in liquid form, so as to redissolve the analyte, but in small volume, such as 0.5 to 5.0 microliters, so as not to substantially dilute the sample analyte or spread it over a larger area than the top surface 61 of capture region 68 in the analyte capture layer 60. With the use of automated dispensing equipment the volume of matrix that is applied may be substantially less, for example 1 picoliter to 1 nanoliter. More usually the volume of matrix will be between 1 microliter and 1 nanoliter. After allowing time for evaporation of the solvent liquid and formation of MALDI matrix crystals, the sample plate is ready for introduction into a MALDI mass spectrometer. Upon insertion of the MALDI sample plate 300 into a mass spectrometer the MALDI matrix crystals are illuminated with an intense UV laser light pulse resulting in ionization of a fraction of the analyte molecules, as is well known in the prior art. The presence, or absence, of discrete molecular weight ions then can be determined, as also is well known in the prior art.

The device 2 will be utilized for analysis of samples by MALDI-MS on standard MALDI-MS sample plates. The MALDI-MS sample plates generally are made of electrically conductive materials so as to prevent electrostatic charging of the sample surface during the laser-assisted ionization process. Capture layers 60 within the device 2 usually will be thin in cross-section, e.g. between 10 microns and 200 microns in thickness, so that electrostatic charge is capacitively coupled to the conductive MALDI sample plate. The capacitive coupling prevents substantial charging of the sample surface to a high voltage, thereby preventing any adverse affect on the electrical field used to accelerate ionized analyte species in the MALDI mass spectrometer. Alternative to a thin nonconductive device, the device may be made of electrically conductive material so that the device may have any reasonable thickness. In this case the thickness of the capture layer 60 can be 1 mm, or more. The conductive material can be any of the aforementioned polymeric materials by adding a conductive material to the polymer. For example addition of conductive, carbon, either as amorphous carbon or graphite, can dramatically increase the conductivity of the capture layer, as is well known in the prior art. Alternatively, the device can be made of a conductive metal, such as stainless steel, aluminum, gold, silver, palladium, copper, chromium, or the like. As still another alternative, doped, or intrinsic, semiconductor materials may be used to provide conductivity to the device. If the semiconductor is intrinsic, electromagnetic radiation above the band-gap of the semiconductor may be provided to provide sufficient conductivity to the semiconductor device in order to dissipate any charge build-up on the capture membrane.

As is well known to operators of such MALDI mass spectrometers, the capture regions 68 can be located and the excitation laser used to excite the top surface 61. As shown in the examples below, excitation of the capture regions 68 having concentrated analyte, including top surface 61, provides for enhanced sensitivity of detection of analytes. The matrix customarily is added in an acidic solution mixed together with an organic solvent in order to enhance the solubility of the matrix, but to allow matrix crystallization as the organic solvent evaporates. Examples of typical MALDI matrices that may be used with the present invention include, but are not limited to sinapinic acid ($C_{11}H_{12}O_5$), alpha-cyano-4-hydroxycinnamic acid ($C_{10}H_7NO_3$) commonly known as CHCA, 3,4,5-trimethoxycinnamic acid, gentisic acid ($C_7H_6O_4$), trihydroxyacetophenone ($C_8H_8O_4$), dithranol ($C_{14}H_{10}O_3$), 2,-(4-hydroxyphenolyazo)-benzoic acid ($C_{13}H_{10}N_2O_3$), 2-aminobenzoic acid, trans-3-indoleacrylic acid ($C_{11}H_9NO_2$), ferulic acid ($C_{10}H_{10}O_4$), nicotinic acid-N-oxide ($C_6H_5NO_3$), 2'-6'dihydroxyacetophenone ($C_8H_8O_3$), picolinic acid ($C_6H_5NO_2$), 3-hydroxypicolinic acid, and 6-aza-2-thiothymine ($C_4H_5N_3OS$). Customarily these MALDI matrix molecules are dissolved in organic solvents miscible with water, such as acetonitrile, acetone, or methanol. Usually the solvent and matrix are mixed together with an aqueous acid solution of such molecules as formic acid, acetic acid or tri-fluoro-acetic acid. The acid keeps the pH of the MALDI matrix solution sufficiently acid to insure that acidic crystals, rather than crystals of salt are formed upon drying.

The acidic solution also ensures that peptide and protein analytes are present in their protonated states where MALDI excitation is more efficient, as is well known in the prior art. A typical MALDI matrix solution would comprise 50% (by volume) of an acetonitrile solution (containing 20 mg/ml of either CHCA or sinapinic acid) and 50% of an aqueous 0.1% TFA solution.

Figure 8:
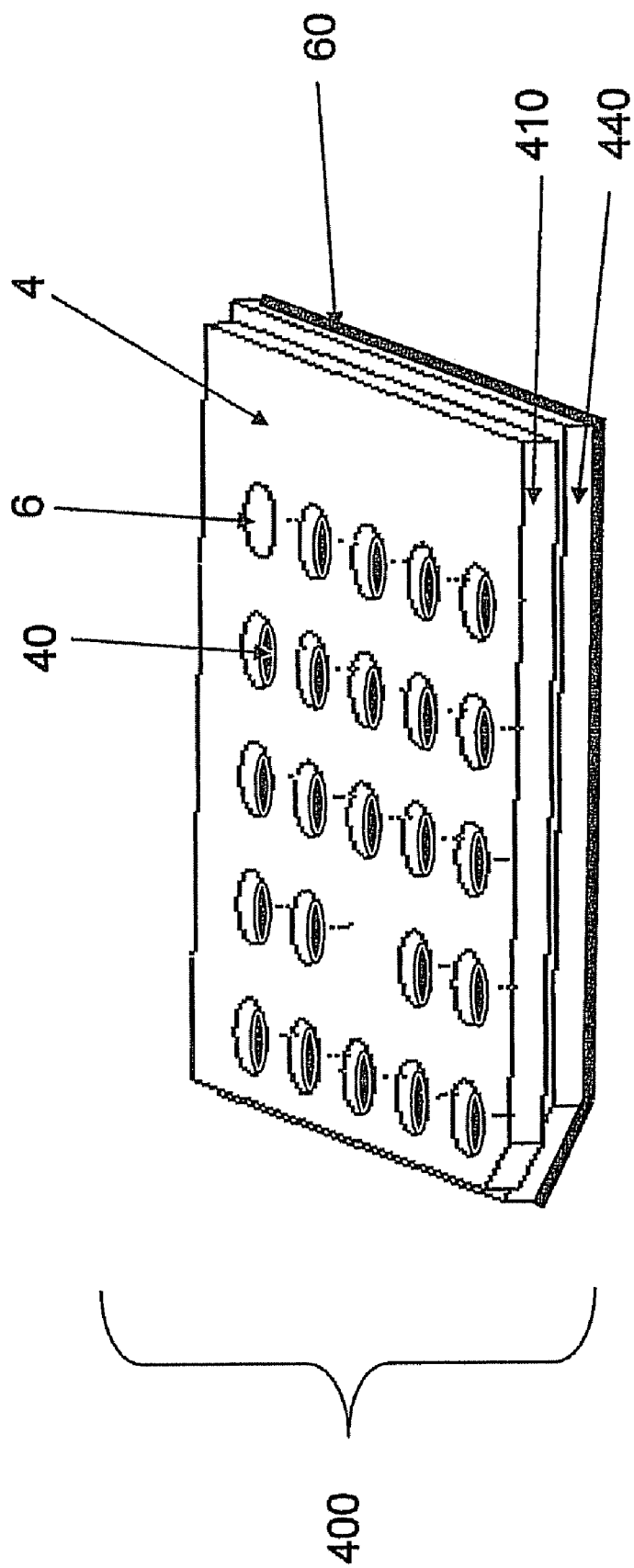
FIG. 8. Slide Assembly showing a Top Component Frame member with Sample Wells having the Separation Layer enclosed within a Center Component Frame Member having the Capture Layer its bottom surface (as seen from top view).

In order to facilitate operation of the device subassemblies are constructed to provide for an array of two or more sample wells and to provide both for sealing retention of porous layers 8 and for rapid disassembly of the device so that capture layer 60 with retained samples and MALDI matrix can be inserted directly an conveniently in a mass spectrometer. FIG. 8 shows the top view of a slide assembly 400 having upper component frame member 410 and lower component frame member 440. The upper and lower component frame members can be disassembled one from the other following completion of sample separation and capture of analytes to capture layer 60. The upper and lower component frame members (410 and 440) facilitate disassembly and mounting of the capture layer. The upper frame member 410 forms the top surface 4 of the separation and concentration device 2. Indentations either molded or drilled into the top surface 4 form the sample wells 6. Separation layer 40 is inserted into the wells 6 conveniently by pouring a polymerizable liquid, such as acrylamide monomer and crosslinker into the wells to the desired thickness. The liquid is then allowed to polymerize, for example either by incorporation of a free-radical chain-initiator such a ammounium persulfate, or by the addition of a photosensitizer, such as riboflavin, and illumination with light of a wavelength absorbed by the photosensitizer, e.g. either UV light or 400-450 nanometer light for riboflavin. Such methods of forming gels by polymerization are well known in the prior art.

Figure 9:
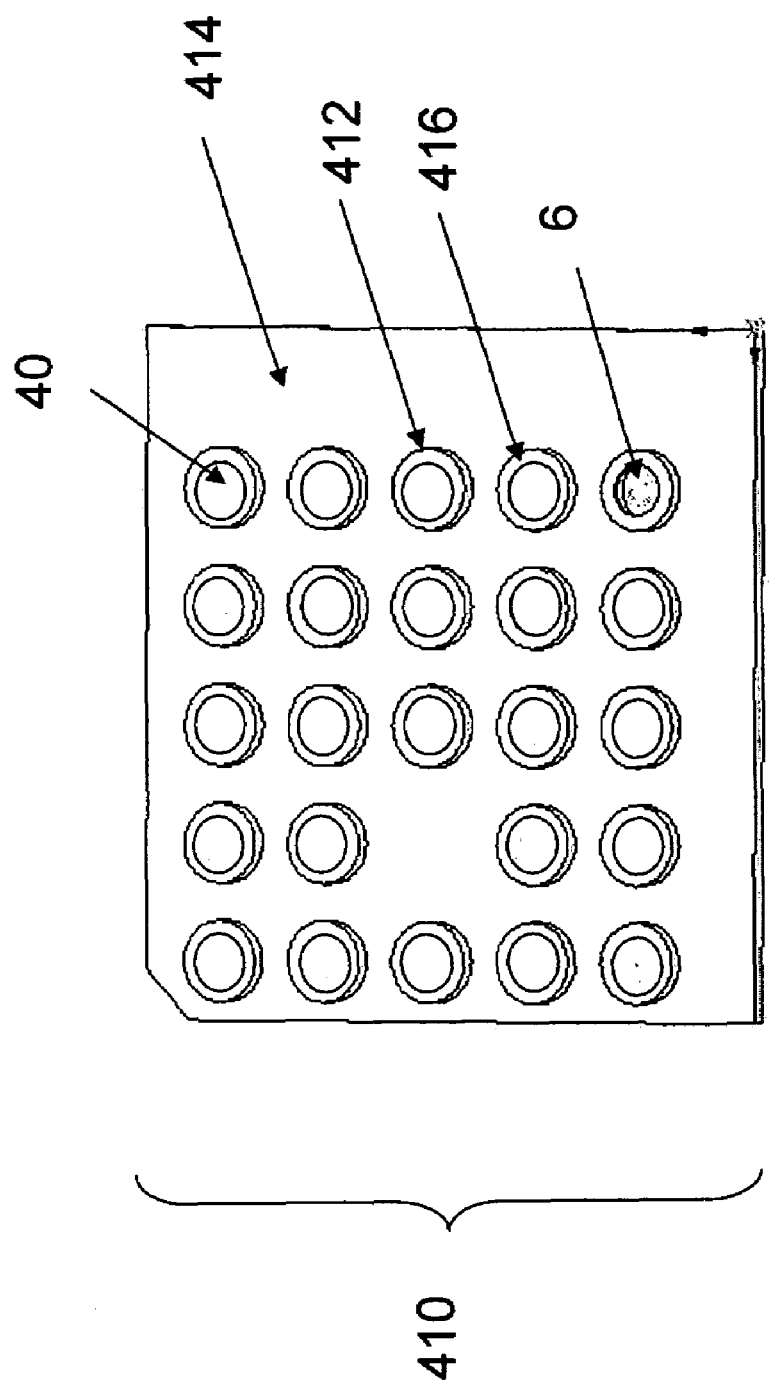
FIG. 9. Bottom View of Top Component Frame Member of Assembly shown in FIG. 8.

FIG. 9 shows a bottom view of the upper component frame member 410 showing its bottom surface 414, which has projections 412 protruding downward from the top surface 4. Separation layer 40 fills the bottom portion of each projection 412 flush to its bottom surface 416. In such a way the separation layer can be placed directly in contact with subsequent porous layers such as capture layer 60, or optionally focusing layer 50. Frame member 410 usually will have a thickness of from 0.5 to 10 mm, more usually from 0.7 to 2 mm. The projections similarly will have a length of from 0.5 to 10 mm, more usually from 0.7 to 2 mm. The total depth of the wells 6 is determined by the combined thickness of frame member 410 plus the length of projections 412 minus the thickness of separation layer 40 placed in the projection (and minus the depth of optional porous absorptive layers 30).

Figure 10:
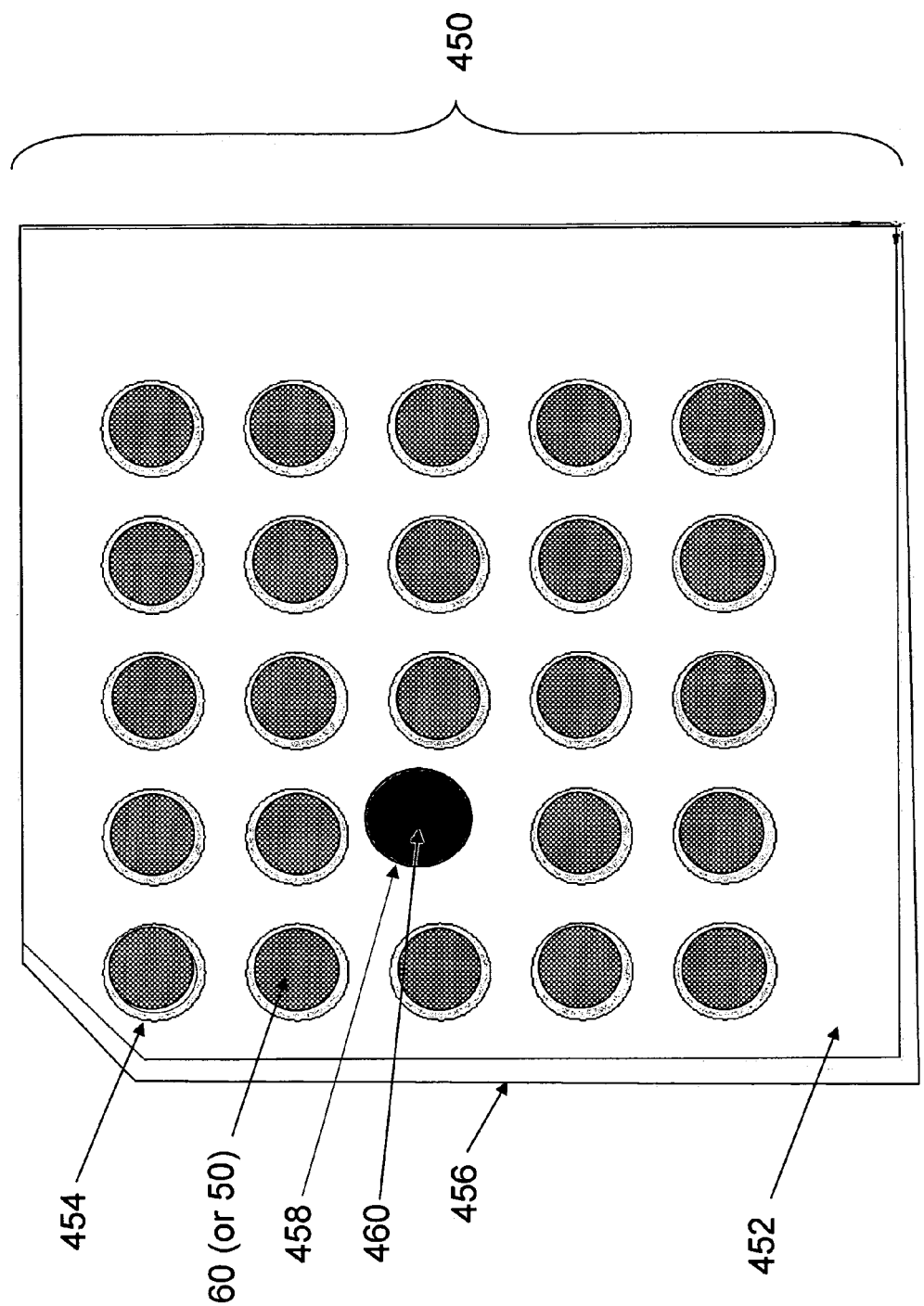
FIG. 10. Top View of the Lower Component Frame member of Slide Assembly shown in FIG. 8.

FIG. 10 shows a top view of the lower component frame member 440 of slide assembly 400. Disposed the top surface 452 of frame member 440 are holes 454 that extend all the way through the lower frame member 440. Disposed on the bottom surface 456 of frame member 440 is capture layer 60 (or optionally focusing layer 50 and then capture layer 60). So that separation layer 40 (disposed within the projections 412 of top component frame member 410) may contact either capture layer 60 or focusing layer 50 directly, the length of the projections 412 in upper component frame member 410 will be approximately equal to the thickness of lower component frame member 440.

Pressed into a recess 458 in the top surface 452 of lower frame member 440 is a ferromagnetic material 460, such as a steel disc approximately 1 mm in thickness. The ferromagnetic material functions to firmly hold the lower component frame member (and the attached capture layer 60) to a MALDI sample plate 300) during mass spectrographic analysis of sample analytes disposed on membrane 60. For this purpose the MALDI sample plates will have a fixed magnet built into the corresponding location on the sample plate.

Figure 11:
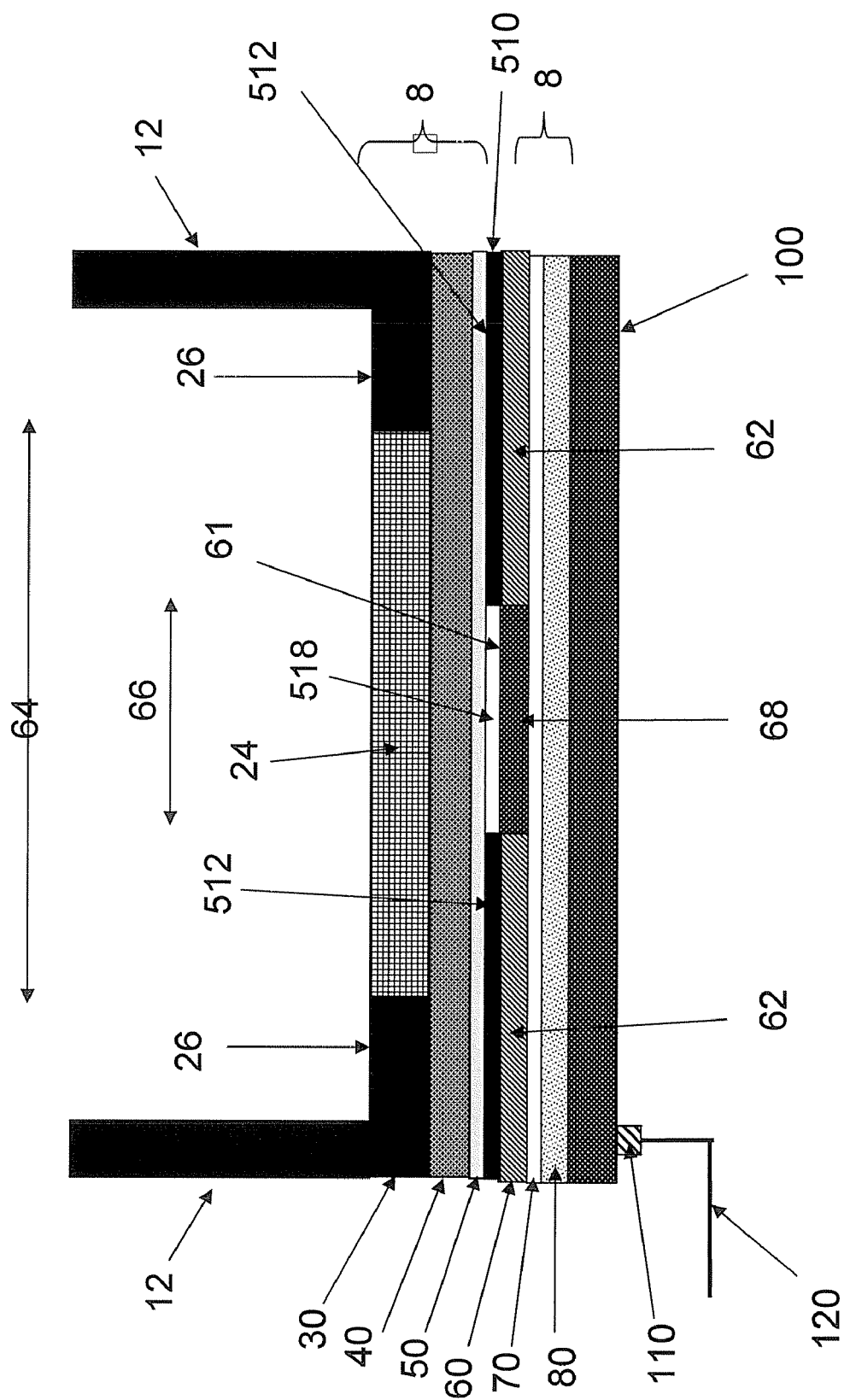
FIG. 11. Alternative Embodiment of Porous Layers (8) in Contact with an Electrode (500) having a Constriction Layer (510) for Capture and Concentration of Analytes onto a Selection Portion (68) of Capture membrane (60).
Figure 12:
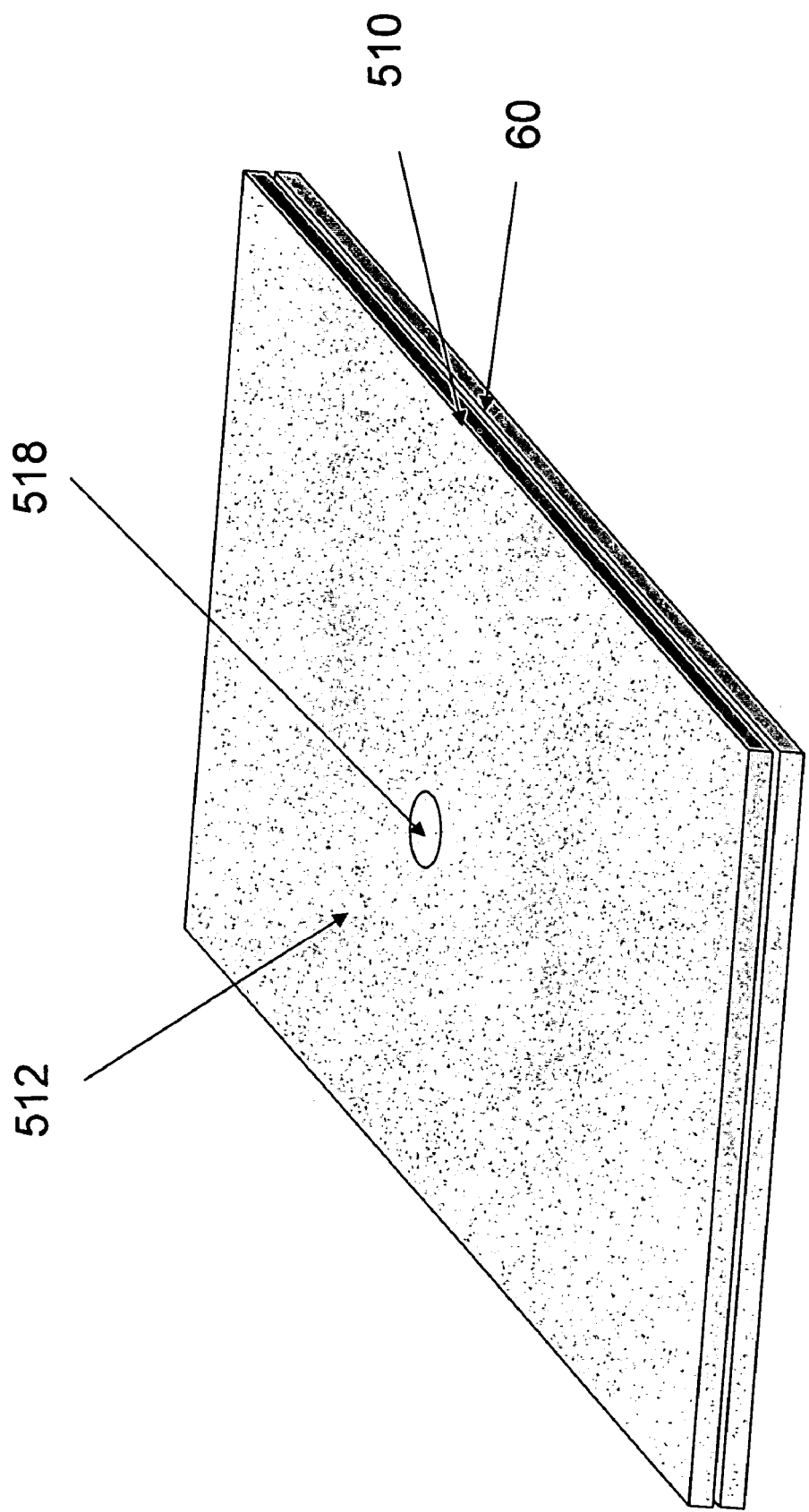
FIG. 12. Top View of a Constriction Layer (510) used to Electrophoretically Focus Charged Analytes through a Concentrating Aperture (518) onto a Selected Portion of Capture Membrane.

F. Devices for Enhanced Electrical Field Focusing and for Chemical Extraction of Analytes from the Capture Slide:

An alternative embodiment of the invention is shown in FIG. 11. This embodiment is similar to that shown in FIG. 10 except that a constriction layer 510 is added between separation layer 40 and capture layer 60. As shown in FIG. 12, constriction layer 510 has an impermeable region 512 and small aperture 518 that allows ionic conduction from separating layer 40, through impermeable region 512, to capture layer 60. The aperture 518 functions to constrain ionic current to pass only through the smaller cross-section capture region 68 of the capture layer 60, where the center of aperture 518 is physically aligned with the center of capture region 68 within capture layer 60. The aperture will usually be between 10 microns and 2 mm in diameter. More usually the diameter will be between 50 and 500 microns in diameter. Constriction layer 510 may be of any thickness but usually will be between 50 microns and 1000 microns thick for the sake of durability and compactness. Especially where constriction membranes are thicker than 200 microns, it is useful to deposit a porous, bibulous, hydrophilic material in the aperture so as to retain aqueous buffer with out the propensity to form gas bubbles in the aperture. The bibulous hydrophilic material may be chosen from a wide variety of materials, for example, agarose, Sephadex, latex, silica particles, glass particles, or the like. The hydrophilic particles need only be smaller in diameter than the thickness of constriction layer 510. Careful attention should, however be paid to the surface charge on the particles. For example when positively-charged macromolecule analytes are being electrophoretically focused through aperture 518, the bibulous hydrophilic material should be chosen to have either a neutral or net positive surface charge. Net negative surface charge may be employed only if the distance between surface charges is substantially greater than the distance between positively charged moieties on the macromolecules. Likewise when negatively-charged macromolecule analytes are being electrophoretically focused through aperture 518, the obverse is true, i.e. the bibulous hydrophilic material should be chosen to have either a neutral or net negative surface charge. Net positive surface charge may be employed only if the distance between the surface charges is substantially greater than the distance between negatively charged moieties on the macromolecules.

Materials that may be used to make constriction layer 510 include metals, such as aluminum, titanium, chromium, zinc, tantalum, tungsten, or alloys thereof together with other elements. Preferably a polymeric material will be used, such as polycarbonate, polyethylene, polypropylene, polystyrene, polyimide, cellulose, nitrocellulose, cellulose esters, nylon, rayon, fluorocarbon, perfluorocarbon, polydimethylsiolxane, polyester, acrylics, acrylonitrile-butadiene-styrene; polyoxy-methylene; polyarylate, polyvinylchloride, PBT-Polyester, polybenzimidazone, acetal copolymers, polyimides, ethylene-chlorotrifluorethylene, PET polyesters, ethylene-tetrafluorethylene, fluorinated ethylene propylene, polyethylene, polyurathanes, polyketones, polychloro-trifluoro-ethylene, polyethylene terephthalate polyesters, polypropylene oxides, polypropylene styrenes, polyetherether ketones, polyarylether sulfones, polyamide-imides, polyarylates, polymethylpentene, polyketones, polysulfones, PBT polyesters, and/or alloys of polymers. Additional materials that may be used to fabricate the concentrator device include acrylics, e.g., LUCITE® or Plexiglas; acrylonitrile-butadiene-styrene (ABS); polyoxy-methylene (Acetal); polyarylate (ARDEL®); polyvinylchloride (PVC); PBT-Polyester (CELANEX®); polybenzimidazone (Celazole®); the acetal copolymers Celcon, or Delrin®; polyimides, e.g., Duratron® or Kapton®; ethylene-chlorotrifluorethylene, e.g. Halar®; PET polyesters, e.g. Ertalyte®; ethylene-tetrafluorethylene, e.g. Tefzel®; fluorinated ethylene propylene (FEP); polyethylene; polyurathanes, e.g., Isoplast®; polyketones, e.g. Kadel®; polychloro-trifluoro-ethylene (Kel-F®); polyethylene terephthalate polyesters, e.g, Mylar®; polypropylene oxides and styrenes, e.g. Noryl®; polyether-ether ketones, e.g. PEEK™; polytetrafluorethylene (Teflon®); polyarylether sulfones, e.g. Radel®; polyamide-imides, e.g. Torlon®; polyphenylene sulfides, e.g. Techtron® or Ryton®; polyarylates, e.g. Ardel®; polymethylpentene (TPX®); polyketones, e.g. Kadel®; polysulfones, e.g. Udel®; PBT polyesters, e.g. Valox®. Other nonporous materials also may be used, however, a particularly preferred material is polyimide (Kapton®).

Figure 13:
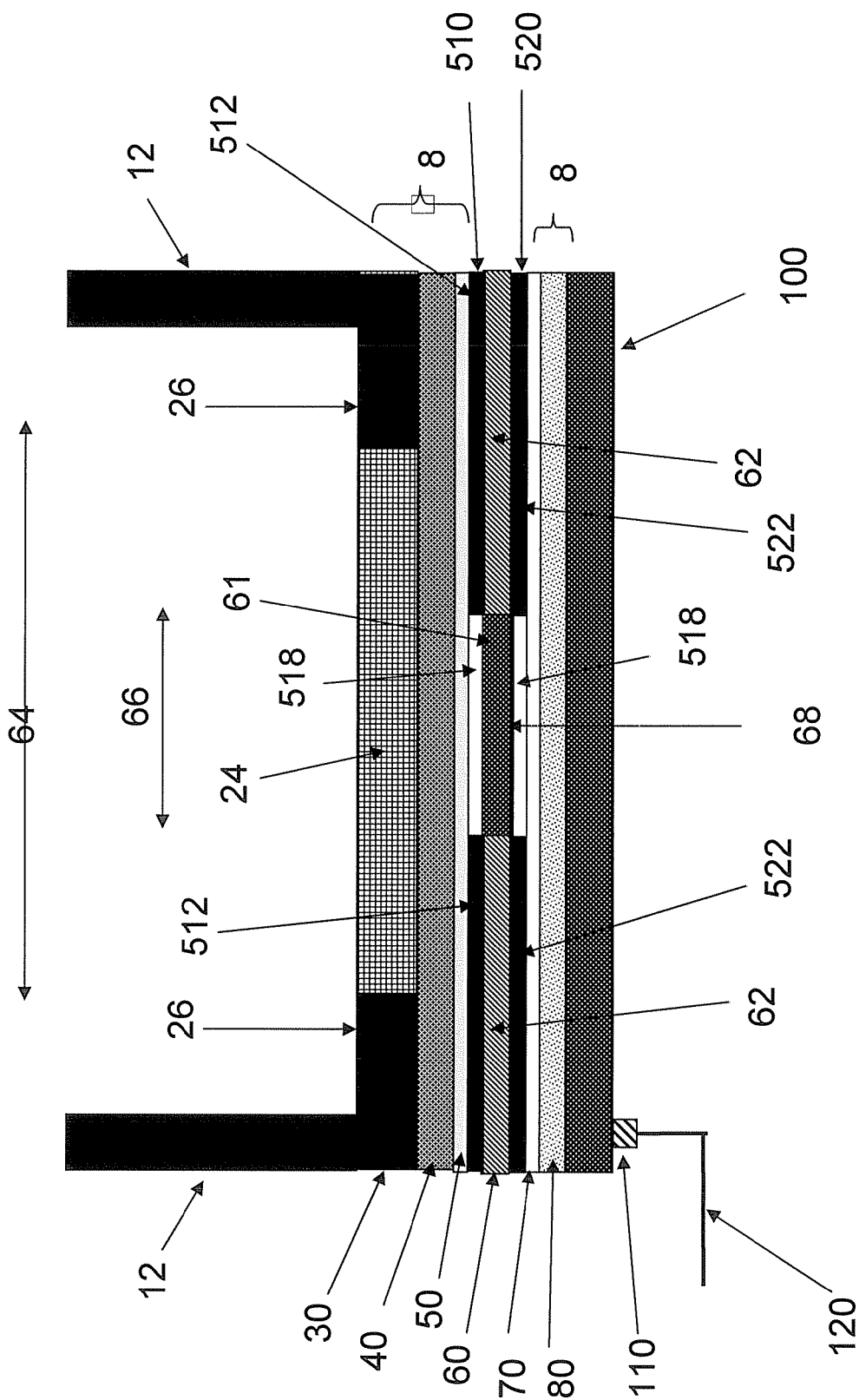
FIG. 13. Variation of Embodiment shown in FIG. 11 with an additional Constriction Layer (510) on the Bottom of Capture Layer (60).
Figure 14:
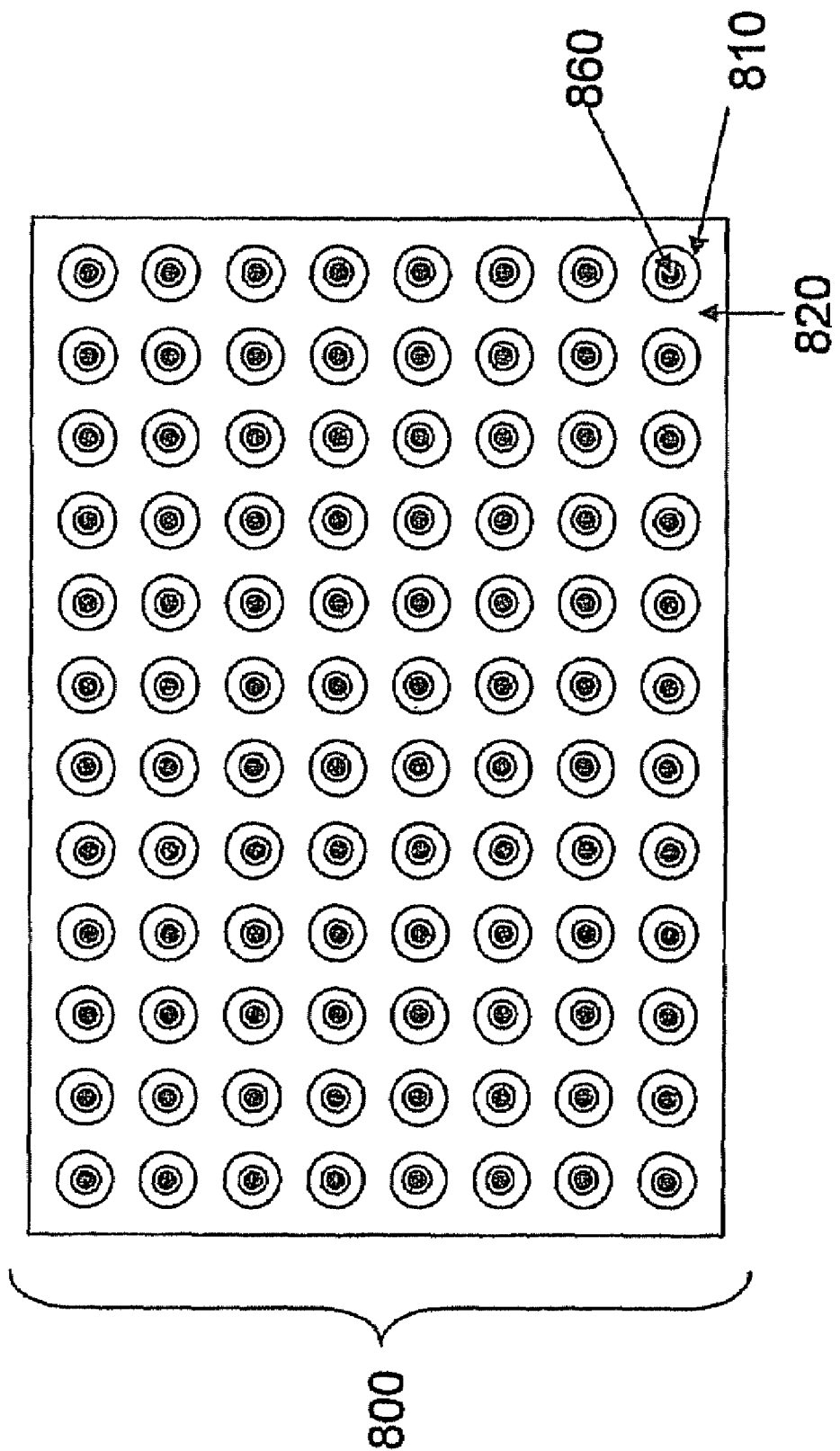
FIG. 14. Device having a two-dimensional array of wells for separation and concentration of analytes.
Figure 15:
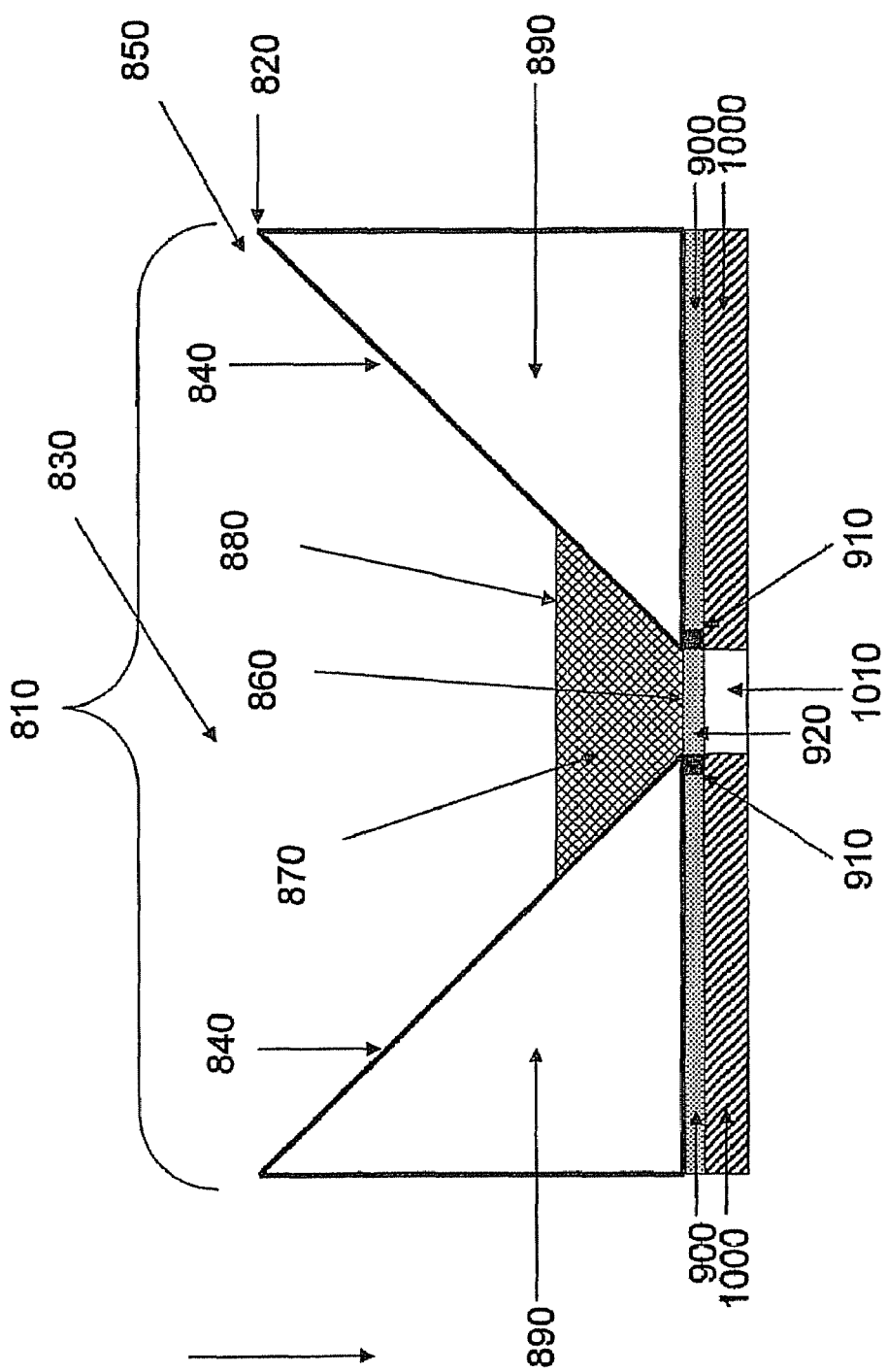
FIG. 15. Side view of a well shown in FIG. 14.
Figure 16:
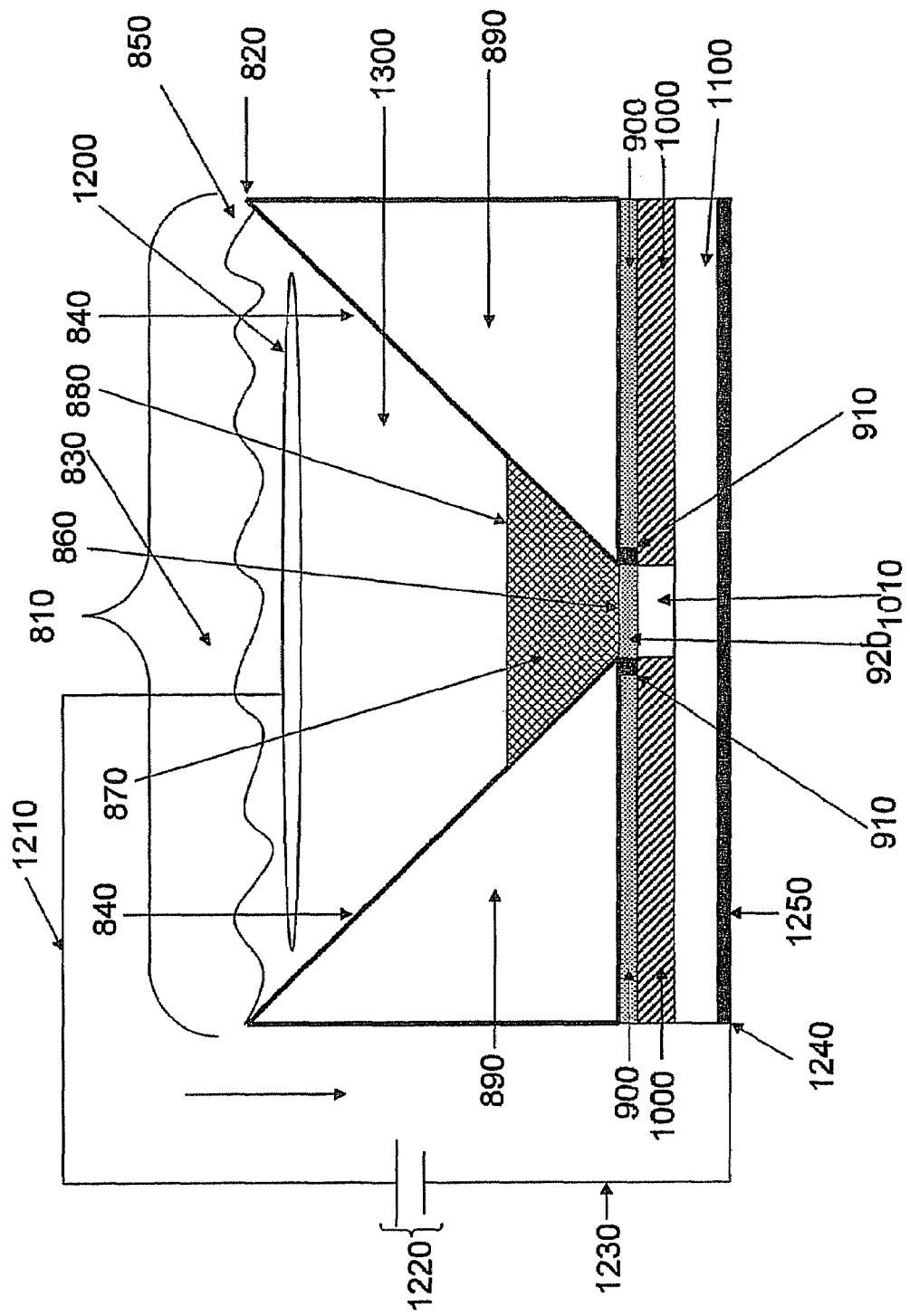
FIG. 16. View of device shown in FIG. 15 with electrodes and bottom electrolyte chamber.
Figure 17:
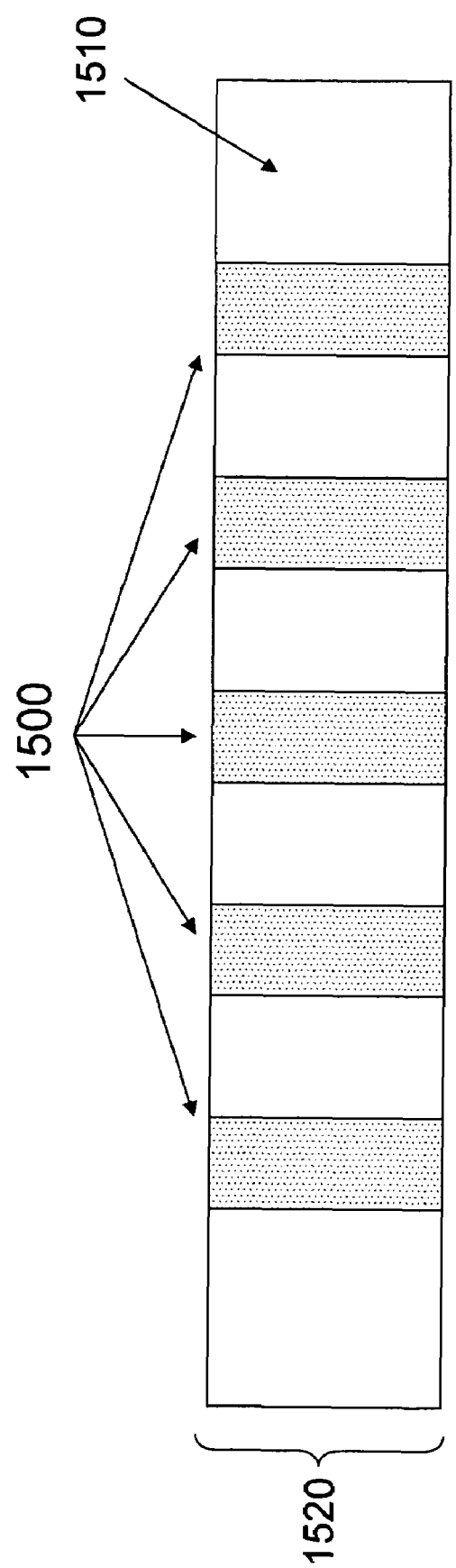
FIG. 17. Side view of the porous capture membrane 900 shown in FIG. 16 comprised of a porous polymer monolith material cast into an array apertures in an otherwise solid polymer layer.
Figure 17A:
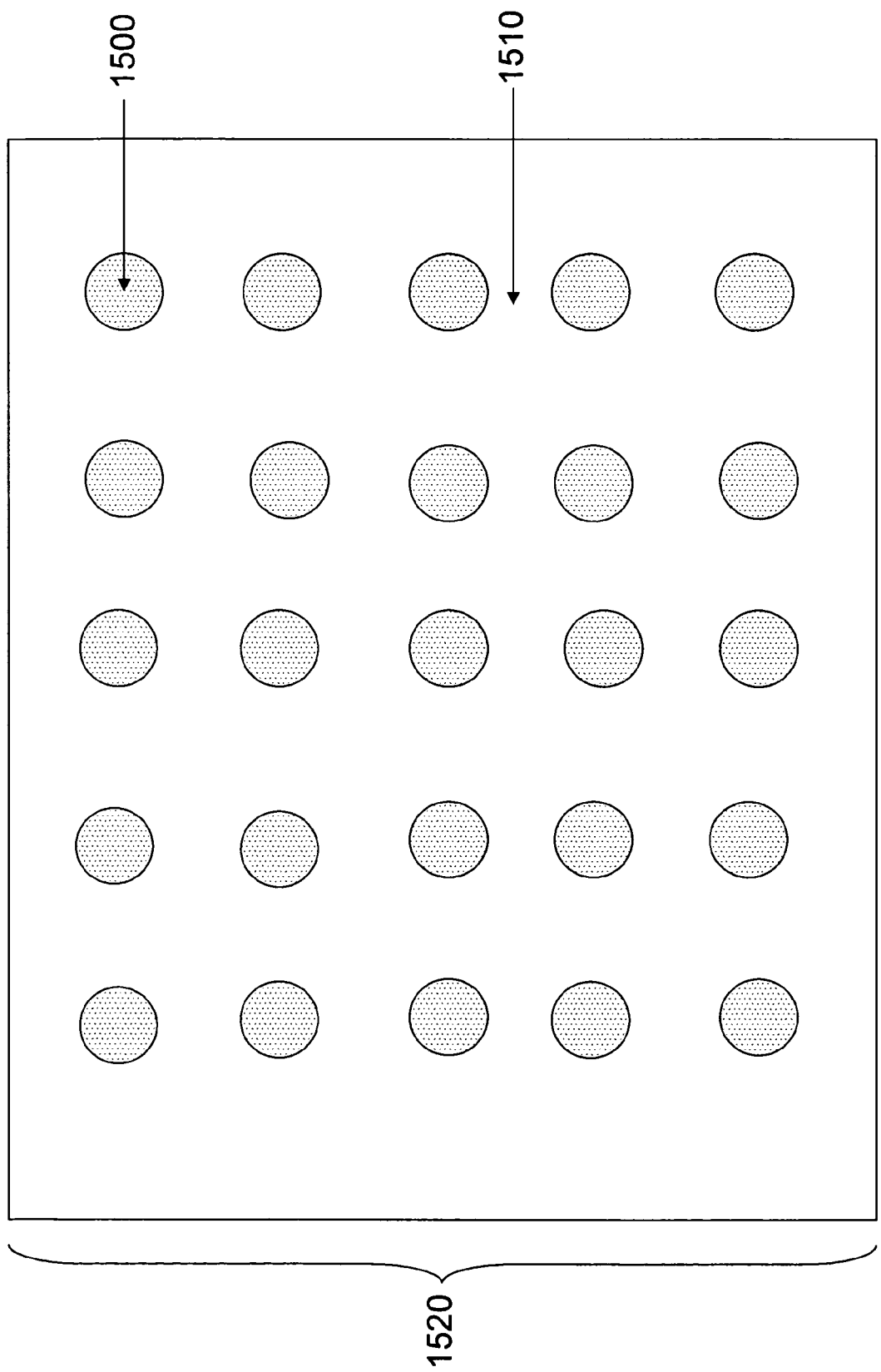
FIG. 17A. Top view of the porous capture membrane 900 shown in FIG. 16 comprised of a porous polymer monolith material cast into an array apertures in an otherwise solid polymer layer.
Figure 18:
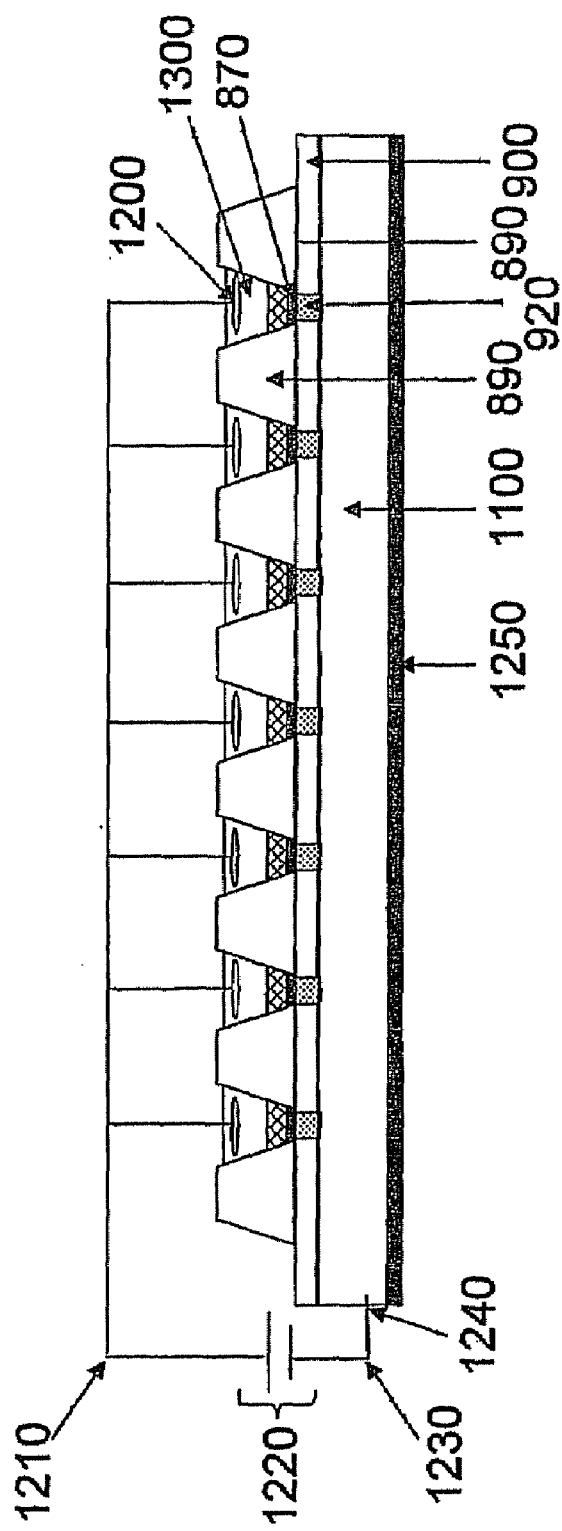
FIG. 18. A side view of an array of wells.
Figure 18A:
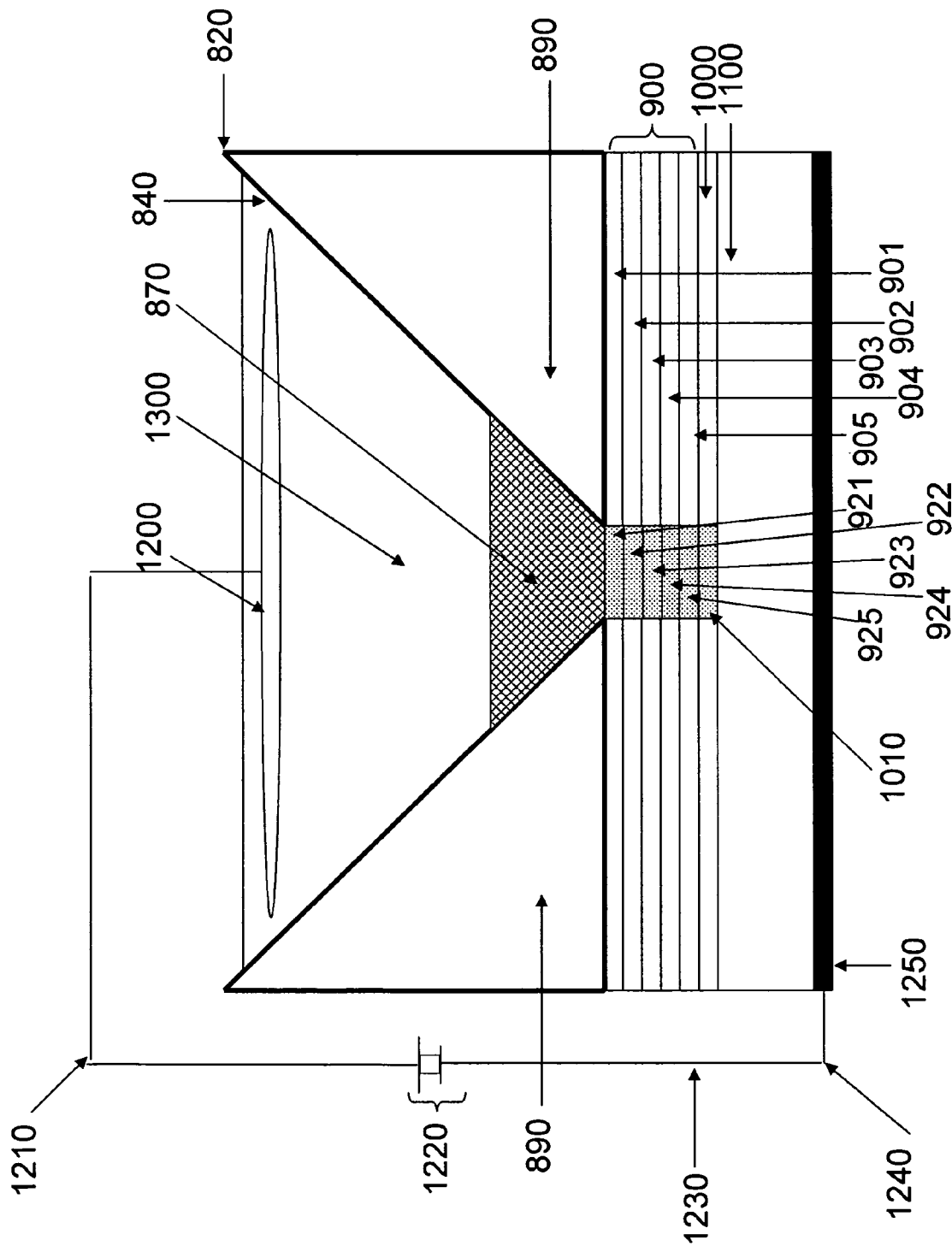
FIG. 18A. View of one well of the device shown in FIG. 15 wherein multiple porous layers are used.

Optionally a second constriction layer 520 may be placed below capture membrane 60 so that capture membrane 60 is "sandwiched" between a first and a second constriction layers as shown in FIG. 13. Advantageously the impermeable regions 512 of the first constriction layer 510 will be welded together with the retained portions of capture layer 60 and the impermeable regions 522 of the second constriction layer so that analytes captured within capture region 68 of capture layer 60 are prevented from moving (either by diffusion, convection, or drift within an electrical field) into region 62 of capture layer 60. In such a way the captured analytes will be retained within region 68 and thus remain more concentrated during subsequent sample preparation steps, e.g. when MALDI matrix is added. Welding of the membranes may be performed by means of application of solvent or heat, for example, as is well known in the art of fabrication and welding of polymeric and metallic materials.

G. Separation Steps to Provide Further Enhanced Sensitivity of Detection

Figure 19:
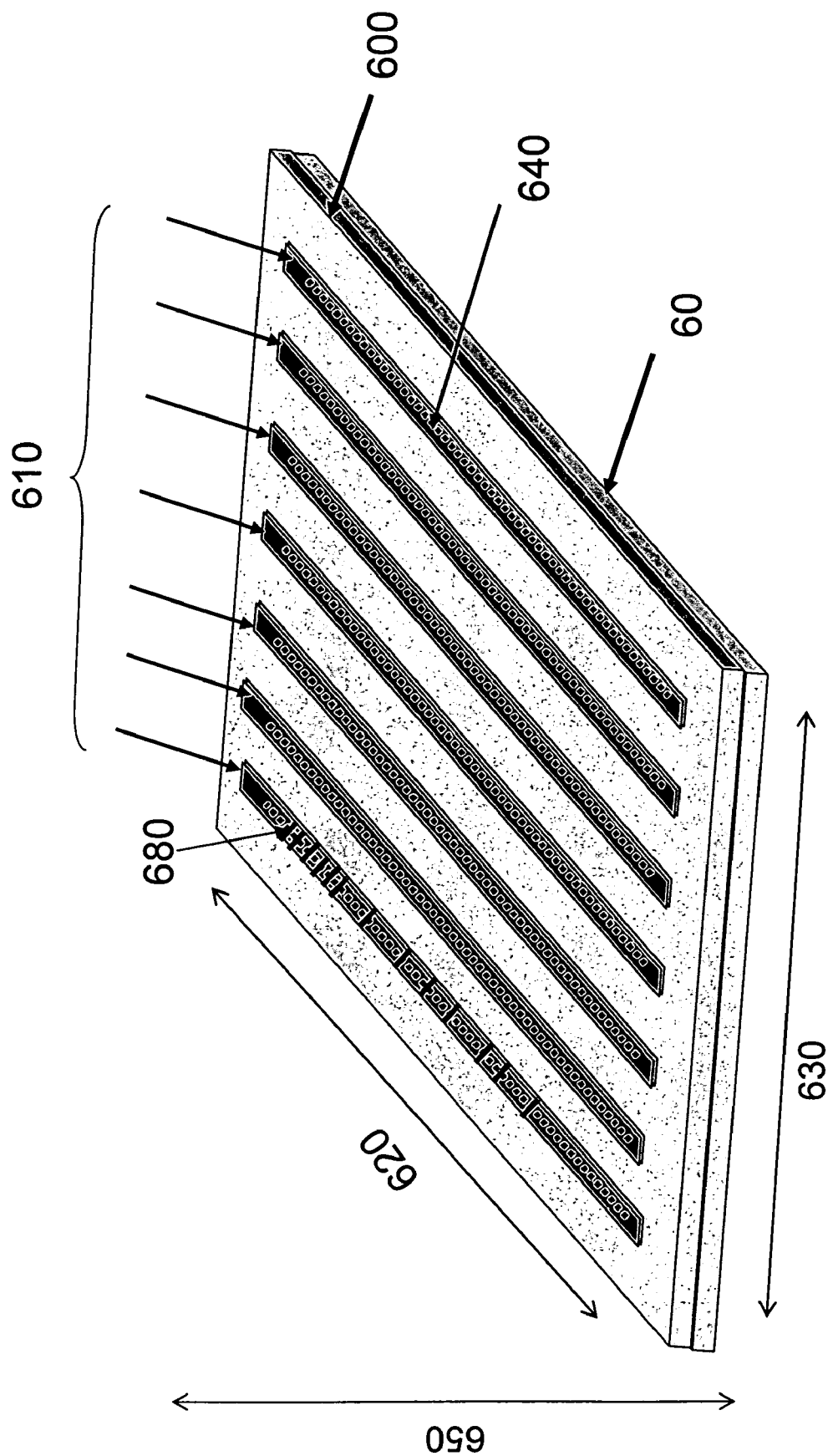
FIG. 19. Top View of a Special Constriction Layer (600) with Overlying Isoelectric Focusing IPG Strips (610) that are used to Provide Improved Separation Prior to Capture for Analysis by Mass Spectrometry.
Figure 20:
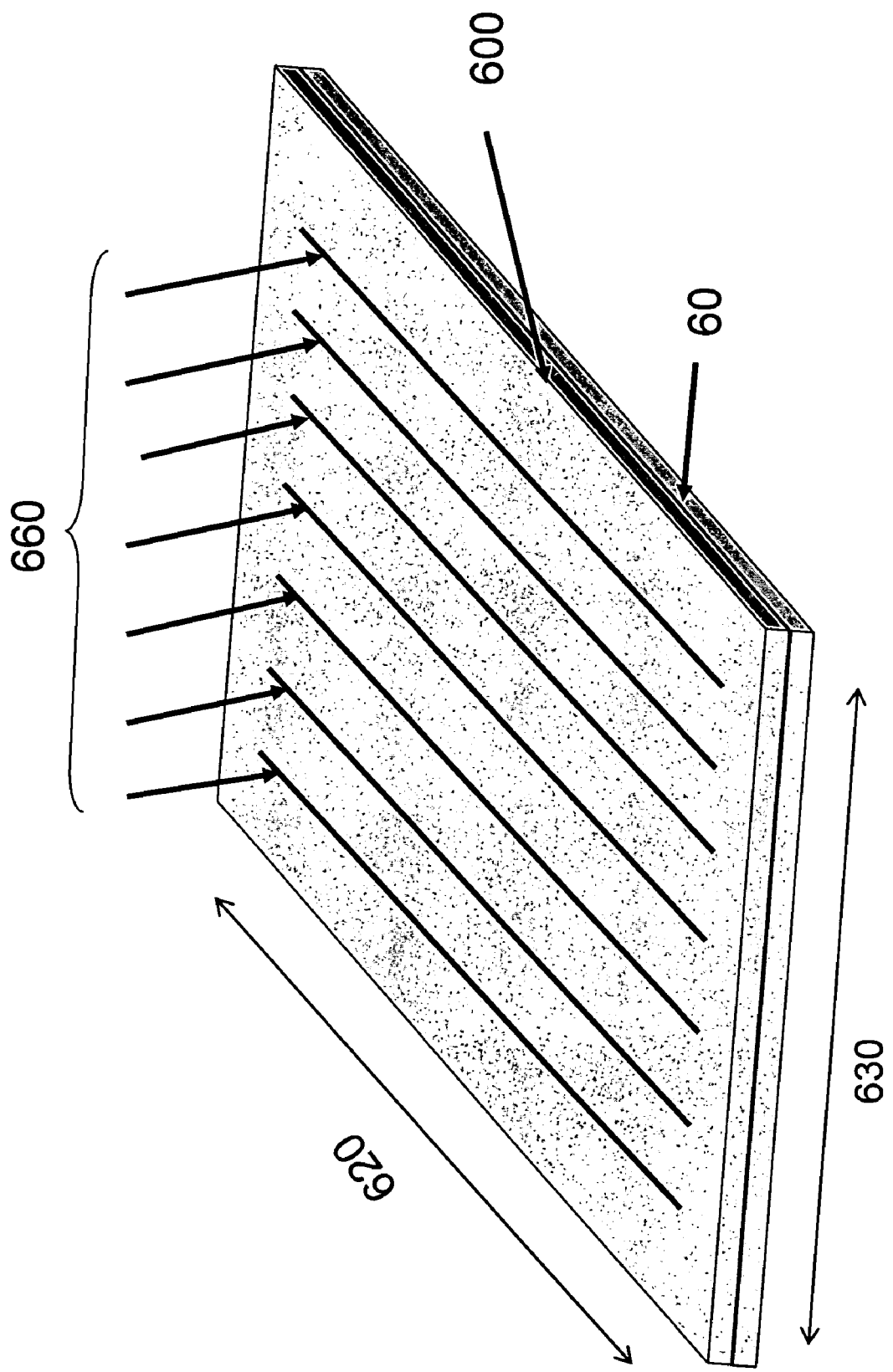
FIG. 20. Top View of Impermeable Layer (600) having Focusing Slits (660) under of IPG Strips (610) used to Provide Improved Separation Prior to Capture for Analysis by Mass Spectrometry.

The device and methods of the present invention may be combined with traditional separation and concentration steps in order to achieve further enhanced separation and concentration thereby resulting in further enhanced sensitivity. The additional steps will take additional time, but the additional steps can be combined with the invention in a way so that the steps can be performed in a substantially automated fashion. Thereby the steps are easy and convenient to perform, requiring few, or no, additional operator intervention or operator-attended run-time.

i) Isoelectric Focusing:

For example, an isoelectric focusing step may be combined together with the purification and concentration steps described previously. Isoelectric focusing of samples may be performed in the device by its modification as shown in FIGS. 19 and 20. The modification includes employing one or more isoelectric focusing strips 610 as the focusing layer. The isoelectric focusing strips are continuous along a first dimension 620 of the device. Two, or more, discrete isoelectric focusing strips can be placed along a second dimension 630 orthogonal to the first dimension. Where there are two, or more, strips, the strips will be substantially parallel. Each isoelectric focusing strip 610 is disposed on constriction layer 600 having a slit 660 centered under each focusing slit. Dashed lines 640 in FIG. 19 show the central axis of each focusing strip 610. Each slit 660 may be viewed simply as an elongation of aperture 518 (see FIG. 13) along the first dimension 620. The central axis of each focusing strip 640 lies directly over an underlying slit 660 in the otherwise impermeable constriction layer 600. Where there are two, or more, isoelectric focusing strips 610, there will be two, or more, slits 660 where each slit is aligned along the central axis 640 of each focusing strip 610 and is substantially parallel to each other slit.

Isoelectric focusing (IEF) may be performed in any suitable stationary matrix, such as cellulose (or glass) or other carbohydrate fiber membranes, beds of Sephadex® particles, agarose, or polyacrylaimide gels. The stationary phase prevents fluid convection so as to provide for a stable pH gradient, as is well known in the prior art of isoelectric focusing. See, for example, P. Glukhovskiy and G. Vigh, Analytical and Preparative Scale Isoelectric Focusing Separation of Enantiomers, *Analytical Chemistry* 71, (17), 1999, 3814-3820, which is herein incorporated by reference.

Briefly, IEF is performed in a pH gradient formed in an aqueous electrolyte between two electrodes placed some distance apart, one as an anode and the other a cathode. The pH gradient may be established initially by placing an acidic medium (i.e. low pH) at the anode and a more basic medium (i.e. high pH) at the cathode. Alternatively the pH gradient may be established as a natural consequence passing a current through an initially uniform pH electrolyte from one electrode to the other. This is because where water is oxidized at the anode the pH will naturally fall according to Equation (4):

$$H_2O - 2e^- \rightarrow 2H^+ + \tfrac{1}{2}O_2 \tag{4}$$

Conversely where water is reduced at the cathode the pH will naturally rise according to Equation (5):

$$2H_2O + 2e^- \rightarrow 2OH^- + H_2 \tag{5}$$

The pH gradient formed in either case can be linearized and stabilized by the addition of carrier ampholytes to the electrolyte. Amphlytes are amphoteric molecules, i.e. they have substituent acidic and basic groups. In order create a stable pH gradient during IEF, a mixture of different carrier ampholytes is used. Each ampholyte has a different isoelectric point (pi), i.e. the pH where the net charge on the ampholyte is zero. The ampholytes migrate in an externally applied electrical field until they reach their pI values in the pH gradient. Their velocity then becomes zero and they buffer against any external perturbation of pH, e.g. by sample analytes when they enter the gradient. When a positive potential is applied to the anode with respect to the cathode the different ampholytes arrange themselves in the electrical field between the anode and cathode in linear sequential fashion such that the ones with lowest pIs are nearest the anode and the ones with the highest pIs are nearest the cathode. Convenient pH 3.0-10.0 ampholyte mixtures are available from Sigma Chemical Company, as product number P1647 for example.

Alternatively, the ampholytes can be bound covalently to the stationary matrix forming an immobilized pH gradient (IPG) on strips or plates. For example, such IPG strips or plates may be purchased commercially from Amersham Biosciences. Amersham product number 17-6003-73 is conveniently employed to form a pH 3-11 gradient over a 7 cm distance, for example. The IPG technology is similar to the pH gradients that are formed when mobile ampholytes are used except that IPG technology establishes the pH gradients with less current, with higher stability, and the ampholytes do not co-elute with the analytes and therefore are less likely to interfere with their subsequent analysis.

In order to perform isoelectric focusing of charged analytes, the analytes next are applied to the pH gradients on the isoelectric focusing strips 610 in the same manner as the ampholytes were added. Also similar to the ampholytes, the analytes migrate to their points of isoelectric pH points and are concentrated. At steady state, the charged analytes thus are found in concentrated bands 680 in the isoelectric focusing strips. At this point the isoelectric focusing is discontinued.

Next the porous layers 60, 70 and 80 (e.g., see FIG. 11 or 13) are assembled below constriction layer 600, the top electrode (140) and bottom electrode 100 are attached, and aqueous buffer is added in sufficient quantity to make ionic contact with the electrodes through the porous layers. Application of a suitable bias potential, as described previously, further focuses the analytes from the isoelectric focusing bands, through the slits 660 in the constriction layer and into a narrow strip on the capture layer 60. After capture of the analytes on the capture layer the device 2 is disassembled and the capture layer 60, as a slide assembly, is attached to a MALDI sample plate after application of a suitable MALDI matrix solution and drying to form MALDI crystals together with analytes, as described previously. In such a way analytes are concentrated in an electric field by isoelectric focusing in a first dimension 620, followed by focusing in an electric field in a substantially orthogonal direction 650 to a predetermined discrete line of analyte molecules on a capture membrane wherein the line of molecules is defined by a corresponding slit 660 in constriction layer 600. Thereby the analytes can be monitored for their mass properties conveniently, but with much improved sensitivity of detection.

EXAMPLE 1

Separation of Ubiquitin Polypeptide from Serum Albumin for MALDI-TOF Analysis on a PVDF Thin Film Membrane by Using Sodium Dodecyl Sulfate (SDS) to Enhance Polypeptide Mobility Labeled Protein Standards:

Texas Red labeled ubiquitin (TR-ubiquitin) and Marina Blue BSA (MB-BSA) were prepared by utilizing the NHS-ester of Texas Red (Cat. No. T-6134, Molecular Probes, Eugene Oreg.) and Marina Blue (product #M-10165; Molecular Probes; Eugene, Oreg.), respectively. The labeling procedure recommended by Molecular Probes was used. Briefly, the NHS-fluorescent labeling species were placed into dimethyl formamide (DMF) at a concentration of about 1 mg/mL and added to a sample of protein at 1 mg/mL, or greater, in standard phosphate-buffered saline (PBS) buffer at neutral pH with vortexing so that the molar coupling ratio of labeling reagent to protein was about 10/1. The labeling reaction with the protein sample was allowed to proceed for one hour. The reaction mixture then was passed through a P6 spin column (Bio-Rad) previously equilibrated with 250 mM L-histidine (Sigma) buffer. Labeled protein samples were dispensed into 25 microliter aliquots and stored frozen.

Electrolytic Cell, Polyacrylamide, Agarose and Porous Membranes:

The basic system for separation and concentration of analytes by photo-electroblotting is shown schematically in FIG. 6. An open-ended sample well was formed from a short cylinder of polystyrene tubing about 2 cm long and about 2 cm in diameter. A separation layer was affixed to one end of the tube to form the bottom of the sample well. The separation layer was formed from a 2-3 mm thick slab of gel made from a precast 10% polacrylamide (obtained from BioRad, CA). The polyacrylamide serves as a molecular weight sieve that retards the electrophoretic velocity of large proteins more than smaller proteins and peptides. The polyacrylamide may be less highly crosslinked to allow faster mobility of larger proteins, or may be more highly crosslinked to better retard the mobility of proteins and peptides as is well known to those skilled in the art of electrophoretic separation of proteins in gel matrices.

Optionally, the edges of the polyacrylamide gel are sealed to the sidewalls of the sample well with a 1% agarose prior to sample addition (in order to prevent fluidic leaks). Both the agarose and polyacrylamide are equilibrated with 250 mM histidine buffer, pH 7.8 prior to use. Alternatively the acrylamide gel may be polymerized in place and no sealing material is needed. Agarose (Type 1-B: low EEO) was purchased from Sigma Chemical Company. Typically, 100 mg of agarose is weighed out and placed into screw-cap glass vials. When used, sodium dodecyl sulfate (SDS) is added to the sample in order to accelerate the electrical mobility of proteins and peptides and to make their mobility less dependent upon the surrounding pH. When SDS is used, 10 microL of 10% aqueous sodium dodecyl sulfate (SDS) (Sigma Chemical Company) in 10 mL of 250 mM L-histidine is added to the 100 mg of agarose. (The SDS is simply omitted for cases where it is not used.) Just prior to use, the agarose is heated sufficiently to form a liquid state in a microwave oven. A film of the agarose is then pored onto the top surface of the precast polyacrylamide along the polystyrene cylinder side-walls 12 in order to seal any fluidic leaks. The agarose is then left to cool until solidified. Next the sample is applied in a 1-10 µl volume of 250 mM L-histidine containing 10% glycerol. The running buffer (identical to the agarose solution above, but without the agarose) is then carefully layered over the top of the sample.

In order to perform the separation and capture of analyte molecules, the precast polyacrylamide is placed onto a series of porous layers 8 as membranes. The membranes are purchased and stored either dry or prehydrated, as indicated below. In either case the membranes are cut into squares (approximately 1.5 cm×1.5 cm) and rinsed with methanol, both in order to wet and to clean the hydrophobic polymer. After transferring to a buffered aqueous solution (e.g. 250 mM histidine) they are stored refrigerated until used. A PVDF-dialysis membrane (250,000 cutoff molecular weight), regenerated cellulose dialysis membrane (1000 cutoff molecular weight) and a CEA dialysis membrane (cellulose ester asymmetric); 500 cutoff molecular weight) were obtained from Spectrum Laboratories, Rancho Domingez, Calif. The PDVF-P (0.45 micron pore size) and PDVF-PSQ (0.2 micron pore size) were obtained from Millipore, Billerica, Mass. Zeta membrane (0.45 micron pore size) was obtained from BioRad, Hercules, Calif.

Semiconductor and Optical Equipment:

An n-type germanium wafer (14 mil thickness and 5 cm in diameter) was purchased from Polishing Corporation of America. The bulk resistivity of the wafer was less than 0.4 ohm-cm. Ohmic contact was made on the upper surface of the wafer by using a gallium/indium eutectic and a copper wire. The ohmic contact was mechanically reinforced with an overlayer of the 5-minute epoxy. The reinforced germanium wafer, was used as the photoanode by mounting onto an optical table together with a laser and focusing optics. The mounted germanium wafer was attached by clamp to a laboratory support stand. The 633 nm line of a helium/neon at 1 milliwatt output was used for photo-electroblotting. The laser impinged on the bottom surface of the glass in a focused beam of between 100 microns and 1 mm in diameter.

In this example, the reinforced germanium wafer was used as the photoresponsive electrode 100 shown in FIG. 6. The buffering layer 80 was comprised of a PVDF-P membrane saturated with 250 mM histidine buffering solution. Upon the PVDF-P membrane was placed under a barrier layer 70 formed from the CEA dialysis membrane. The capture layer 60 was comprised of the PVDF-dialysis membrane mentioned above. The polyacrylamide separation layer, 40, together with additional materials to form the sample well mentioned above, were assembled directly onto the capture layer, buffering layer and photoresponsive electrode.

Electrophoretic Separations and Blotting:

Either 0.2 µL of TR-ubiquitin, MB-BSA (1-2 µg/µL), or both, were incorporated into a 2 µL sample containing 250 mM aqueous histidine buffer with 25% (v/v) glycerol. The sample was mixed and spun down at about 1000×g for 2 minutes. About 0.5 µL of the supernatant was used for each separation and electroblotting run. The mass spectrographic results from mixtures of proteins were compared to the use of purified standard protein or peptide samples (e.g., containing only ubiquitin and 1% TFA). The pure (standard) samples of ubiquitin were diluted directly into 0.1% TFA (to either 800 fmol/µL or 10 fmol/µL) so that no interfering species would be present after evaporation of the solvent prior to analysis by MALDI mass spectrometry.

To begin the electrophoretic process, the lead 120 from an ohmic contact on the photo-responsive electrode is connected to a potentiostat (Princeton Applied Research). Between the sample and (on top of) the photo-responsive stainless steel MALDI sample plate, allowed to dry. Next the sample plate was placed into the mass spectrometer for analysis.

MALDI-MS Analysis Protocol:

Analysis was performed with an ABI/Perceptive Biosystems Voyager DE (MALDI-TOF) instrument by using the provided QGEN_PR2 method. For use with CHCA matrix solutions settings were: 25 kV accelerating voltage, 89% grid voltage, 0.25% guide wire voltage, 200 ns delay, 2800 laser setting, 64 scans averaged, 3.45 e-7 torr, 100 low mass gate, negative ions off.

Results:

Photo-electroconcentration of TR-ubiquitin directly onto a CEA dialysis membrane (without a PVDF membrane) was performed as described above. The MALDI mass spectrum shown in FIG. 21 was obtained after extracting the oligopeptide from the membrane into a MALDI matrix solution containing CHCA, and spotting the solution directly onto a stainless steel target plate and allowing the solution to evaporate to dryness. The multiple peaks represent 0, 1, 2, 3 or 4 molecules of Texas Red covalently attached to each ubiquitin polypeptide.

Figure 21:
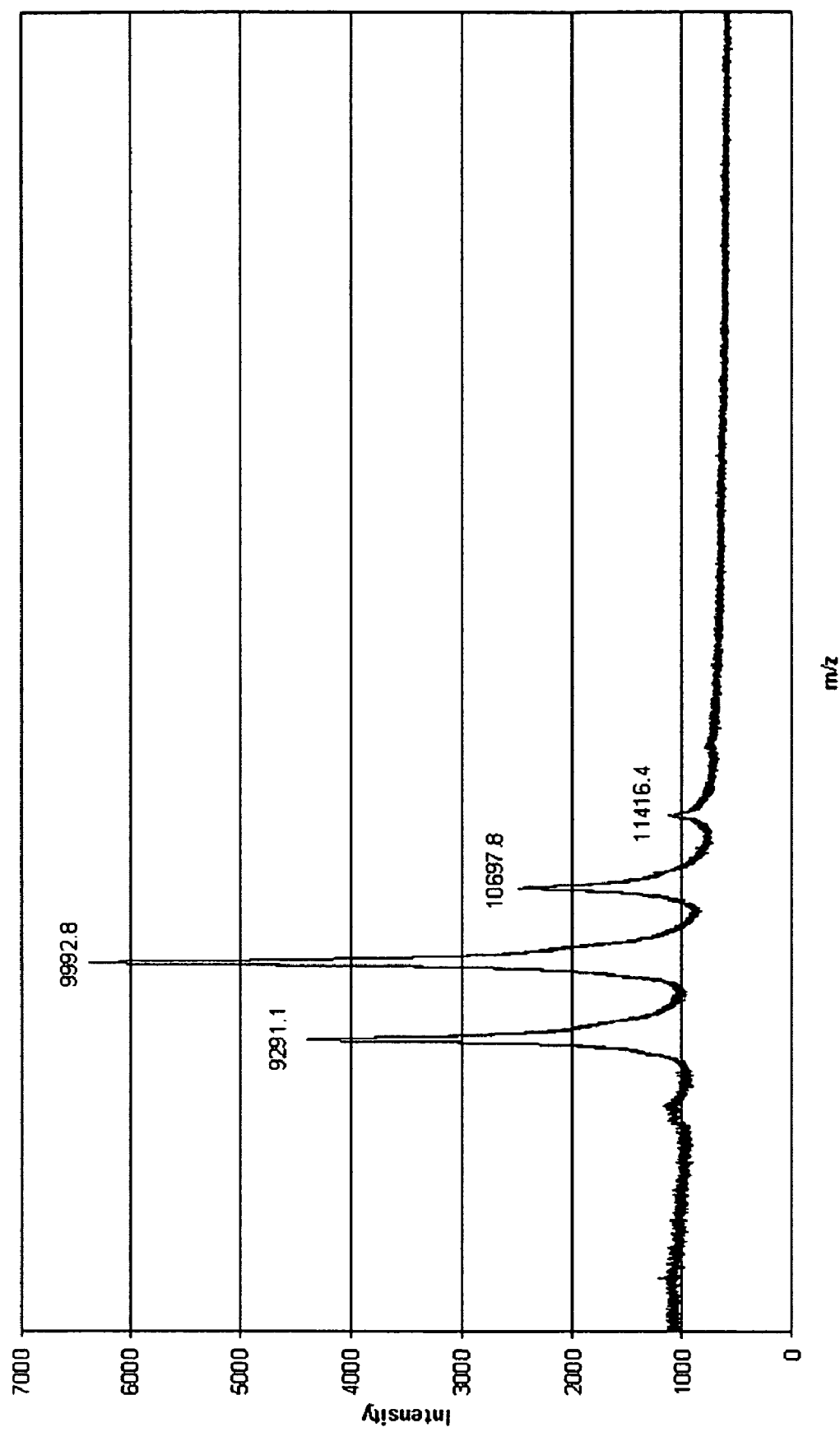
FIG. 21. Mass Spectrum from a Mixture of Ubiquitin Oligopeptide Sample Labeled with (0, 1, 2, 3 or 4 molecules) Texas-Red and Photo-concentrated onto a 500 MW Cut-Off CEA Dialysis membrane. This spectrum was obtained after extracting the oligopeptide from the membrane into a MALDI matrix solution containing CHCA, and spotting the solution directly onto a stainless steel target plate and allowing the solution to evaporate to dryness.
Figure 22:
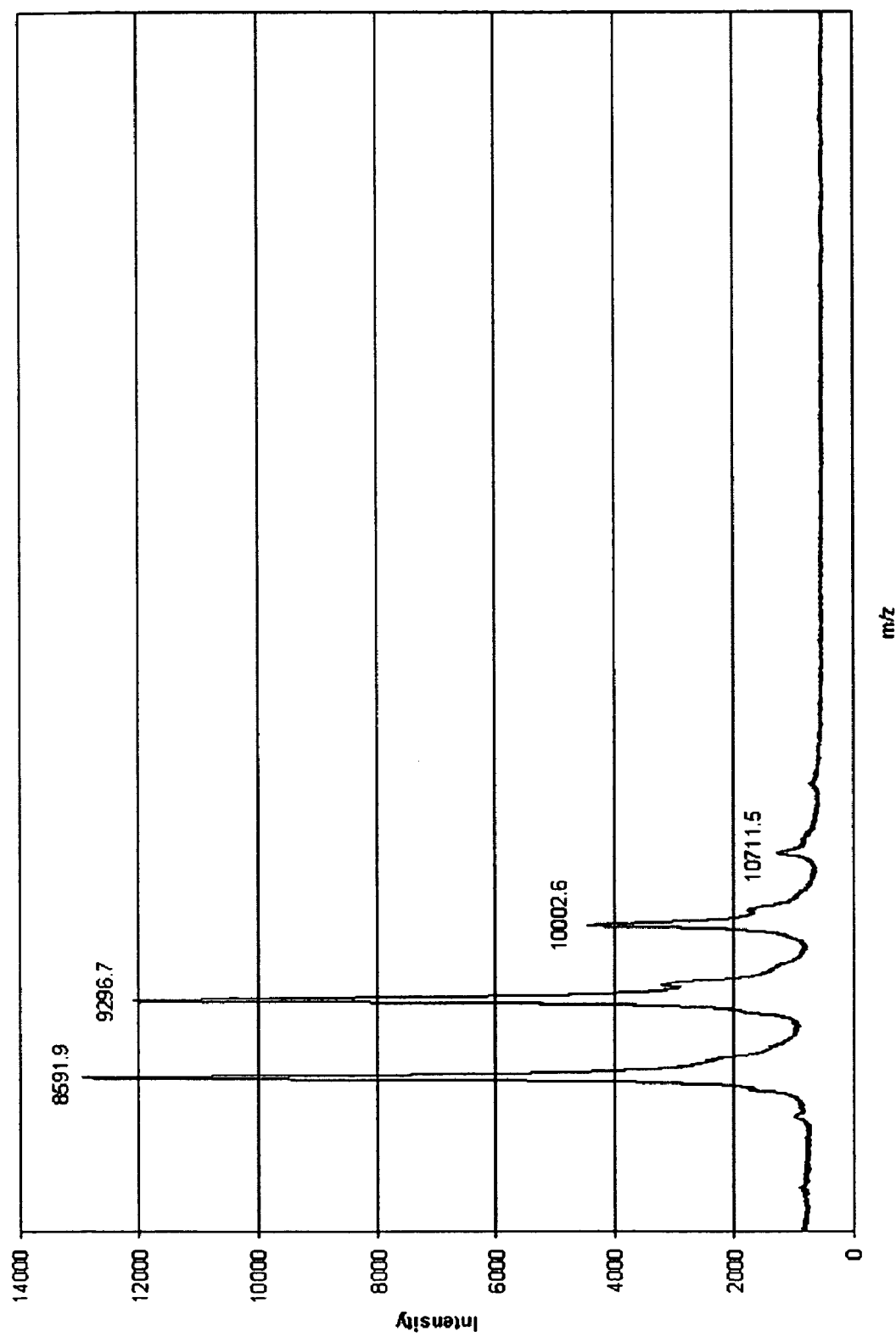
FIG. 22. Mass Spectrum from the same ubiquitin sample shown in FIG. 21. The ubiquitin sample, however, was photo-concentrated onto a 250,000 MW cut-off PVDF-dialysis membrane and the CHCA MALDI matrix solution was added directly to the PVDF membrane, evaporated to dryness and affixed to the stainless steel MALDI sample plate by double-coated adhesive tape (3M).

For comparison, in FIG. 22 is shown the MALDI mass spectrum from the same ubiquitin sample after the sample was photo-concentrated onto a 250,000 MW cut-off PVDF-dialysis membrane (backed by the CEA 500 MW cut-off dialysis membrane). After completion of the photo-electroblotting, the PVDF dialysis membrane is washed with water, dried and the CHCA MALDI matrix solution is added directly to the sample concentration sites. The matrix solution then is evaporated to dryness and the PVDF dialysis membrane is affixed directly to the stainless steel MALDI sample plate by double-coated adhesive tape (3M) and then analyzed using MALDI-TOF. Comparison of FIGS. 21 and 22 show two main differences. First, the intensity of the ion current for the largest intensity peaks is greatest when the PVDF membrane is used. Thus it appears as if the efficiency of capture is greatest when the procedure with the PVDF membrane is used. Second, upon capture by the two different membranes, distinctly different ratios of ubiquitin labeled with 0, 1, 2, 3, or 4 molecules of Texas-Red are observed. Capture by the CEA membrane appeared to result in fewer molecules with 0 or 1 Texas Red label per molecule of ubiquitin. Thus, it appears as if the CEA dialysis membrane preferentially binds the ubiquitin molecules that are more highly labeled with Texas Red-labeled (and thus more negatively-charged). In contrast the PVDF membrane appears to more uniformly capture all of the labeled ubiquitin molecules as shown by comparison of analyses performed by directly dispensing the labeled ubiquitin sample onto a stainless steel MALDI target (data not shown).

EXAMPLE 2

Separation of Negatively-Charged Serum Peptides from Whole Human Serum onto a MALDI-Compatible Membrane A major problem with analyzing low abundance peptides in blood, plasma, or serum is that the high abundance proteins mask the appearance of low abundance peptides. Removal of the highly abundant albumin from blood, plasma or serum samples has been reported to also remove a significant number of low abundance peptides. Thus finding a way to dissociate the low abundance peptides from albumin is an important task. In the present studies we treated serum samples with detergents in order to promote dissociation.

Human Serum Samples:

Detergent-treated serum samples were made by adding 5 mg/mL octyl-β-D-glucopyranoside (OG) to ten (10) µL of human serum (obtained from Sigma Chemical Co.) in an Eppendorf microtube (500 µL volume). The detergent-treated serum was then stored at 4 degrees C. overnight and after 14 hours brought to room temperature. Samples were then made from a three (3) µL aliquot of the detergent-treated serum, 1 µL of 250 mM histidine buffer, 1 µL of Texas Red labeled-Leu enkephalen (as a tracer in 250 mM histidine buffer) and electrode were placed the utilized membrane combinations while the membranes are in a "wet/buffered" state. On top of the membrane layers is placed a plastic cylinder (2 cm diameter and 2 cm in height). The hot agarose solution is then added so that the liquid attains a height of 3-5 mm. Once the agarose solidifies, another 3-5 mm of aqueous buffer (250 mM histidine with 0.01% SDS) is added. The counter electrode (e.g. Pt, Pd, or carbon) at the top of the electrolytic cell is now immersed so that it remained close to the agarose. The sample (TR-Ub or MB-BSA) in 25% glycerol and 75% histidine buffer is added, so that it makes electrical contact with the circular counter electrode at the top of the electrolytic cell. The remaining portion of the separation and concentration procedure is carried out in a darkened chamber. A bias voltage is applied between the photo-responsive electrode and the counter electrode and an illumination source (e.g. a 4 milliwatt diode laser irradiating at 600-700 nm wavelength) is focused to about a 50 micron diameter spot on the back (lower) side of the wafer, so that it is centered vertically with respect to the center of the counter electrode at the top of the electrolytic cell. Typically the bias voltage applied to the a germanium electrode (vs. a platinum counter electrode) is about +4 volts, which results in about 500 µA of total current (~40% of which is photocurrent, i.e. the current in the dark is about 300 µA). Typically, the electrophoretic separation and capture run is allowed to proceed for about 9-20 minutes.

After the separation and concentration, the counter electrode and top buffer in the sample well is removed. Then the acrylamide separation layer is removed and the capture membrane is submersed either in deionized water (or preferably in 0.1% TFA) for 2-5 minutes to remove salts. The capture membrane (e.g. PVDF thin film) then is adhered to a stainless steel MALDI sample plate with 3M double-coated adhesive tape. Matrix solution is then added to the membrane and allowed to dry. The sample plate is placed into the mass spectrometer for analysis.

For the MALDI-MS analysis directly on stainless steel, from 0.5 to 2.0 μl of matrix solution containing the analyte of interest was spotted directly on a 0.5 μL of glycerol. The resulting sample mixtures were centrifuged at about 1000 g for about 1 minute in order to bring together the 1 and 3 μL droplets.

Sample Wells and Separation Layer:

Samples were then placed into the sample reservoir of a Serum Profiler analytical cell for separation and concentration onto a MALDI-compatible membrane for mass spectrometry analysis. The reservoir of the concentrator is made of a sample ring made of an electrically nonconductive material such as polystyrene, polyethylene, polypropylene, polycarbonate, polymethylamethacrylate, polymethylpentene, Teflon™, or the like, which forms the side-walls of the sample reservoir.

The bottom surface of the sample reservoir serves to bring the sample into ionic electrical contact with separation structure formed by one, or more layers of separation medium. In the instant example the separation medium was formed by a single layer formed from a 2-3 mm thick slab of gel made from a precast 10% polacrylamide gel (obtained from Bio-Rad, CA). The polyacrylamide serves as a molecular wt. sieve to retard the electrophoretic mobility of large proteins but to allow the more rapid electrophoretic mobility of smaller proteins and peptides. The polyacrylamide may be less highly crosslinked to allow faster mobility of larger proteins, or may be more highly crosslinked to better retard the mobility of proteins and peptides as is well known to those skilled in the art of electrophoretic separation of proteins in gel matrices. Optionally the edges of the gel are sealed into place with 1% agarose gel. Both the agarose and polyacrylamide were equilibrated with 250 mM histidine buffer, pH 7.8 prior to use. (Alternatively the acrylamide gel may be polymerized in place and no sealing material is needed.)

Capture, Barrier and Buffering Layers:

Under the polyacrylamide separation layer, and in ionic electrical contact therewith, is a capture layer that serves to capture polypeptide analytes including peptides, oligopeptides and proteins. Capture proceeds by hydrophobic interaction of the polypeptides with a polymeric capture membrane. Particularly useful for capture of polypeptides by hydrophobic interaction are membranes made of materials such as porous Teflon or PVDF. In this example the capture membrane is comprised of a PVDF-dialysis membrane (250,000 molecular weight cutoff) that is received and stored in aqueous buffer (250 mM L-histidine) at 4 degrees C. prior to use.

In ionic electrical contact and under the capture layer is placed an optional barrier membrane layer that prevents the escape of relatively nonhydrophobic proteins and peptides. A CEA dialysis membrane (cellulose ester asymmetric, 500 MW cutoff) is used as the barrier layer and is stored dry prior to use. Both the capture and barrier membranes are cut into squares (approximately 1.5 cm×1.5 cm) and then rinsed with methanol just prior to use in order to insure cleanliness. Both membranes are obtained from Spectrum Laboratories, Rancho Dominguez, Calif. No solvent elution steps were performed after analytes are captured in the capture layer until addition of a small volume, e.g. 0.3-2 microliters, of MALDI matrix solution. Thus hydrophobic proteins and peptides are captured by the PVDF dialysis membrane irrespective of the molecular size cutoff of the capture membrane.

Buffering Region:

Below the capture and barrier membrane combination, and in ionic electrical contact therewith, is located a buffering region to buffer (or capture products that are formed at the surfaces of electrodes that are used to produce an electrical field which causes electrophoretic movement, separation, and concentration of analyte molecules in the capture membrane. In the present case the buffering region is comprised of a single layer of Immobilon-P membrane (obtained from Millipore Inc.) and saturated with 250 mM L-histidine buffer, pH 7.8.

Photoresponsive Electrode:

Just below and in ionic electrical contact with the buffering layer is a photoresponsive anode made from an n-type germanium wafer. The germanium wafer (14 mil thickness and 5 cm in diameter) was purchased from Polishing Corporation of America. Resistivity was less than 0.4 ohm-cm. The germanium wafer, mounted on a glass plate with 5-minute epoxy, was used as both the working electrode and photoanode. Ohmic contact to a copper lead was made on the upper surface of the wafer by using a gallium/indium eutectic and a copper wire. The ohmic contact was mechanically reinforced with an over layer of the 5-minute epoxy.

Method for Analysis of Human Serum Samples:

In order to perform separation and binding of sample components, an aliquot (0.5-8 μL) of the detergent-treated sample mixtures was added to the sample reservoir on top of the acrylamide/agarose layer. Next a circular counter electrode (cathode) made of platinum and loosely in contact with the inner side walls of the reservoir, was placed directly into the sample. The platinum cathode and photoresponsive anode were connected to a potentiostat (Princeton Applied Research, model 273), the room darkened and a bias voltage of +4V was applied to the photoresponsive anode with respect to the platinum cathode. The 633 nm line of a helium/neon at 1 milliwatt output was used for photo excitation of the back surface of the photoresponsive anode (i.e. the light was shined on the wafer on the side opposite to the electrolyte). A laser focusing system was constructed so that laser impinged on the bottom of the glass reinforcement in a focused beam of between 100 microns and 1 mm in diameter. The 4.0 volt electrical bias and simultaneous illumination resulted in ~700 mA of total current (~30% photocurrent). Separation was allowed to proceed for about 20 minutes before the bias voltage was set to zero and the leads to the top and bottom electrode disconnected.

Next, the accumulation chamber was dismantled and the gels and membranes checked for fluorescence. If the capture process was complete, all fluorescence should be contained on the capture membrane. The fluorescence spot was cut out and soaked in deionized water for a few minutes. The PVDF membrane was allowed to dry out and prepared for MALDI analysis as described in Example 1. The captured proteins were then analyzed directly in a Voyager DE workstation from the PVDF membrane by using the procedures described in Example 1 above.

Figures 23, 23A:
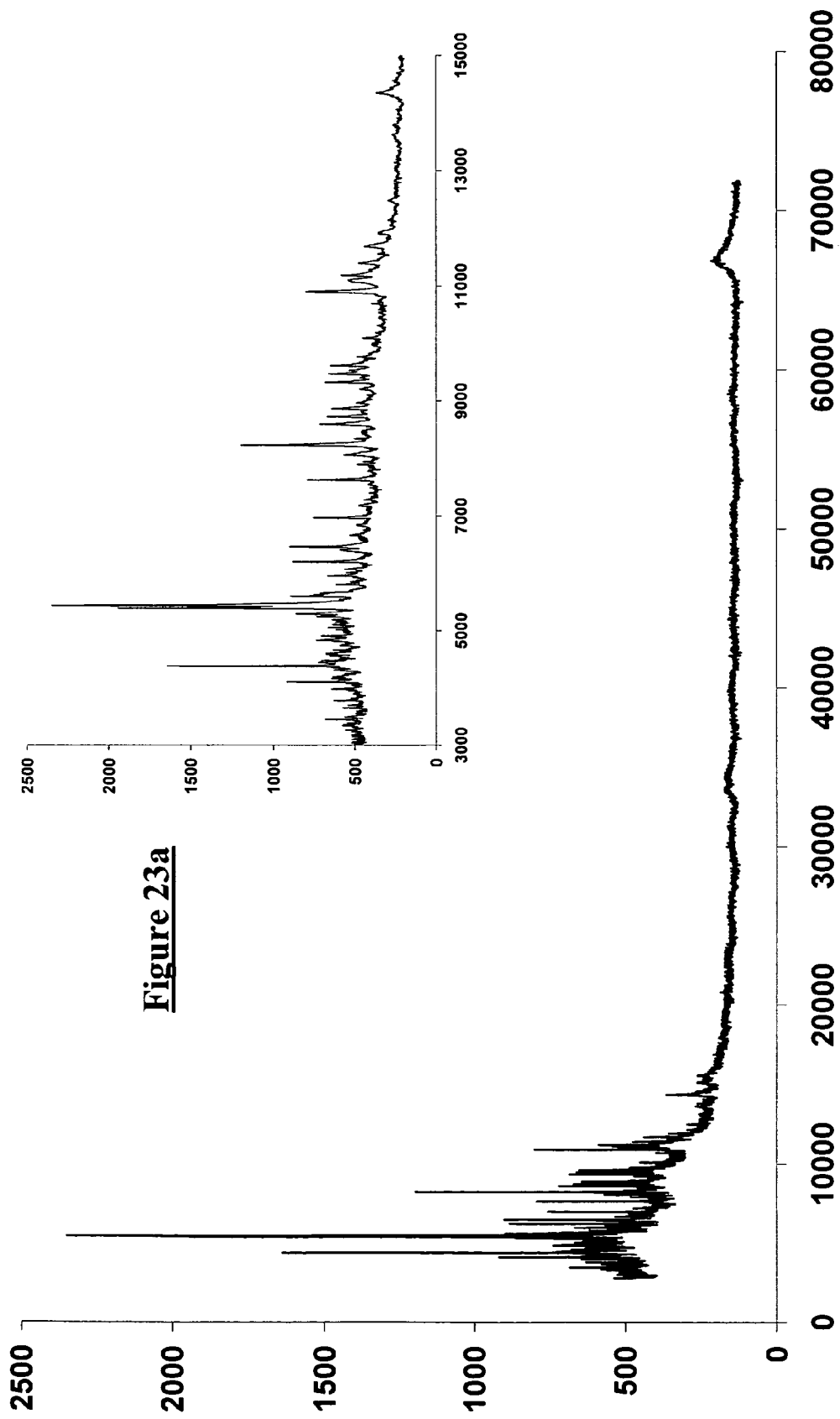
FIGS. 23 & 23A are Mass Spectra of Negatively Charged Serum Proteins Electro-Concentrated on PVDF Capture Membrane (with Sinapinic Acid as a MALDI matrix).
Figure 24:
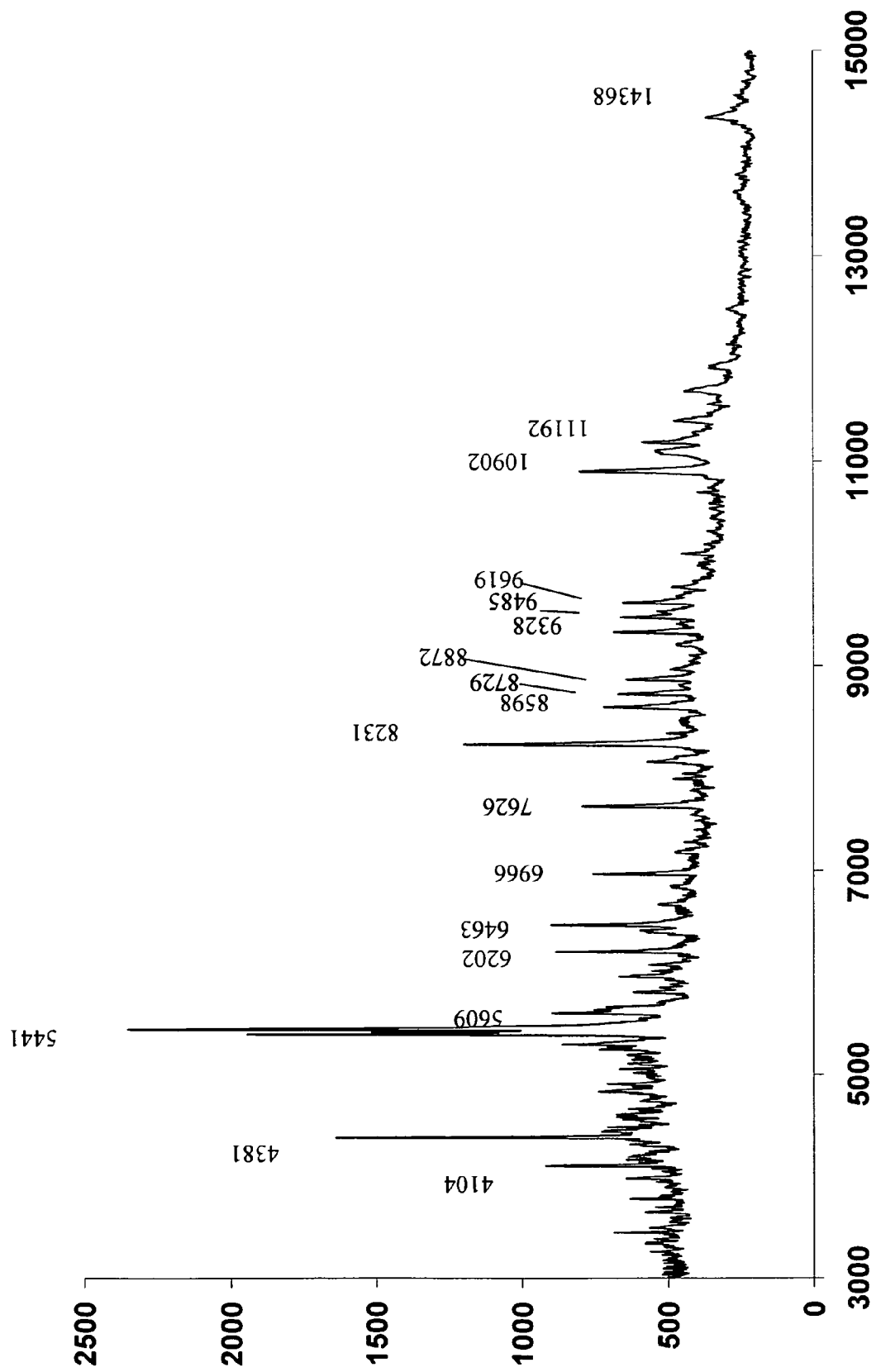
FIG. 24. Mass Spectra of Negatively Charged Serum Proteins Electro-Concentrated on PVDF Capture Membrane (with CHCA as a MALDI matrix).

Shown in FIGS. 23, 23*a* and 24 are typical results for negatively-charged proteins and peptides when analyzed with either CHCA or sinapinic acid included in the MALDI matrix solution. Mass analysis with CHCA in the MALDI matrix solution gave the best results for low molecular weight peptides and polypeptides 1000 to 15,000 daltons. In contrast sinnapinic acid in the matrix solution gave improved signals at higher molecular weights (i.e. >15,000 daltons). Thus two separate MALDI analyses with each of these matrix materials gives optimal results for both the lower and the higher molecular weight ranges.

EXAMPLE 3

Electrophoretic Separation of Positively-Charged Serum Peptides from Whole Human Serum for MALDI-TOF Analysis on a PVDF Thin Film Membrane Similar to Example 1 and Example 2 above, in this example peptides and small serum proteins from a human serum sample are electrophoretically concentrated onto a capture membrane after having passed through a gel to separate the larger proteins from the smaller proteins and polypeptides of interest. As in the previous examples, the charged peptide and protein molecules drift in an electric field applied by an external anode and cathode. In this example, positively-charged analyte molecules drift toward a negatively-charged cathode and are concentrated and become bound within capture region 68 of a capture layer 60. The captured positively-charged proteins are then analyzed directly from the capture membrane as described in the previous examples, The MALDI analyses are carried out in a Voyager DE mass spectrometer, as described in Example 2.

A major difference between previous Examples 1 & 2 and the present Example 3 is that no photoresponsive electrode is essential in Example 3. Instead non-photoresponseive electrode materials, similar to those described previously for fabrication of top electrode 140, may be used for either the bottom electrode 100 which can be either a cathode or an anode. Although a photoresponsive electrode is not required in this alternative embodiment, instead at least one constriction layer 510 with at least one aperture 518 is required to provide for focusing of analytes into the capture region 68 of capture layer 60. As shown in FIG. 13, a second constriction layer 520 may be employed advantageously. The constriction layers are impermeable to ionic current except through an aperture 518 that serves to focus analytes of interest into the capture region 68 of capture layer 60. Thus the current-directing action of a photoresponsive electrode is not required.

Materials:
Bottom electrode (100): Palladium (Pd) foil may be covered with Kapton (polyimide) adhesive tape so as to selectively pattern conductive regions on the bottom electrode, as may be desirable. For example, a 2 mm diameter hole in the Kapton tape serves to expose this area of Pd that is used as the bottom electrode surface.
Top electrode (140): The top electrode was made of Platinum (Pt) wire shaped into a ~3 mm diameter loop. For operation with 3-electrode potentiostat or galvanostat, the top electrode is attached both to the controlling electrode and the reference electrode leads from the potentiostat or galvanostat.
Bottom electrode (100) is prepared by boring a 2.4 mm hole into a 1"×3" piece of Kapton tape. The adhesive tape is placed over a small piece of palladium (Pd) foil, and both are secured to a glass microscope slide. The working electrode lead from the potentiostat is connected directly to the foil with a clip.
Buffering layer (80): The buffering layer is comprised of an Immobilon-P membrane obtained from Millipore, Inc. The Immobilon-P membrane is saturated with 250 mM aqueous L-histidine solution, pH 7.8.
Barrier layer (70): 500 molecular weight cut-off, CEA dialysis membrane, obtained from Spectrum Laboratories, Inc.
Capture layer (60): 500 molecular weight cut-off, polyvinylidine difluoride dialysis membrane (PVDF-DM), obtained from Spectrum Laboratories, Inc.
Separation layer (40): 10% polyacrylamide, obtained from Bio-Rad Laboratories, Inc.
A gel comprised of 1% low EEO agarose (obtained from Sigma Chem. Co.) in saturated aqueous DL-glutamic acid and DL-aspartic acid is used to seal the separation layer (40) to the side walls (12) of the sample wells (6).
Sample Buffer Aqueous buffer is used to dilute the sample and to make electrical contact between the top and bottom electrode. The aqueous buffer is saturated DL-glutamic acid and DL-aspartic acid (obtained from Sigma Chem. Co.) The pH of the buffer is =3.0.
Sample Wells (6): A single polycarbonate cylinder with an open top and bottom is used to construct a separation and concentration device having a single well. The single well is 19.15 mm O.D.×16.95 mm I.D.×17.32 mm high.
Sample: 1 μL glycerol+1 uL of ubiquitin (obtained from Sigma Chem. Co.) and labeled with Texas Red (Molecular Probes, Inc.) according to the manufacturer' recommendation+8 μL human serum (obtained from Sigma Chem. Co.)+≈1 μg octyl-β-D-glucopyranoside (obtained from Sigma Chem. Co.)+3 μL of sample buffer. Once all components of the sample are added together, they are centrifuged and vortexed (to mix). A 5 μL aliquot of the sample then is pipetted into the sample wells.
MALDI Matrix Solutions: A first MALDI matrix solution is a-cyano-4-hydroxycinnamic acid (CHCA), saturated in 50% acetonitrile and 0.1% trifluoroacetic acid. A second MALDI matrix solution is sinapinic acid (SA) dissolved at 10 mg/mL in 50% acetonitrile, 50% 0.1% trifluoroacetic acid. All materials for the MALDI matrix solutions were obtained from Sigma Chem. Co.

Instrumentation:
Electrode bias voltage or current control: A model 273 potentiostat/galvanostat from EG&G Princeton Applied Research was used either in the potentiostat or galvanostat mode.
Data acquisition: Powerlab/4SP, AD Instruments, and a desktop PC from Dell.
MALDI Mass Spectrometry: Voyager DE Biospectrometry Workstation, (Applied Boosters, Inc.).

Membrane Preparation:
Prior to sample separation, concentration and binding to the PVDF layer capture (60), the PVDF membranes are soaked in methanol for ~1 minute. Since the PVDF membranes are hydrophobic, the methanol serves to initial "wet" the membrane and also serves to clean the membrane. The wetted PVDF membrane then is placed in deionized water for storage. The separation layer (40) is prepared from precast 10% polyacrylamide, obtained from Bio-Rad Laboratories. The polyacrylamide is removed from its cassette, cut into disks with the polycarbonate cylinder used for the sidewalls (12) of the sample wells. The cut disks are soaked overnight in deionized water together with the CEA membrane that is used as the barrier layer (70). The high salt concentration in the pre-cast polyacrylamide gels necessitates the overnight soaking in water in order to reduce the conductivity to an acceptable range. Although the device may be operated over a wide range of conductivity of the separation layers and sample buffers, for example from 1 micro-siemen to 100 milli-siemens. Optimal operation of the device is in a narrower range of from 10 micro-siemens to 10 milli-siemens.

Device Construction:

The separation and concentration device (2) is constructed by placing the porous layers over the bottom electrode in the following order: buffering layer, capture (layer), constriction layer, separation layer, heated agarose gel to seal side walls to the separation layer, aqueous buffer and top electrode. The heated agarose is pipetted into and around the side walls of the sample well to a depth of 1-2 mm. Once the agarose gels, the Pt loop used as the top electrode is carefully lowered into the cell until it contacts the agarose. Sufficient aqueous buffer is then added to cover the Pt loop top electrode.

Operation of the Device:

A sample containing human serum is prepared by adding 1 µL glycerol+1 uL Texas Red-labeled ubiquitin+8 µL human serum+<1 µg octyl-β-D-glucopyranoside+3 µL of aqueous buffer. The solution is centrifuged briefly, vortexed, and a 5 µL sample is then dispensed into the cell through the center of the Pt loop. The bottom electrode is biased at −5V with respect to the bottom electrode. The current is monitored continuously. After an initial transient, the current settled down to about 200 µA for the remainder of the 45-minute separation and concentration steps. The Texas Red-labeled-ubiquitin is used as an indicator analyte to track visually the progress of separation and capture of analytes. The time and current needed for separation are adjusted retrospectively in order to optimize separation and capture.

At the conclusion of the separation and concentration steps, the bias voltage is set to zero and the device disassembled. The 366 nm emission setting of a Mineralight, Entela UVGL-58 fluorescent lamp is used to visualize the fluorescently-labeled tracking proteins, such as Texas-Red ubiquitin on the capture membrane. The fluorescent spot on the PVDF-DM capture membrane is cut out, submerged in deionized water for 2 minutes, and dried under a stream of nitrogen. For attachment to a MALDI sample plate the membrane is divided into two, or more, pieces each about 2 sq. mm in area. While the pieces are on a stainless steel MALDI sample plate, 1 µL of CHCA matrix is added to at least one piece and 1 µL of SA matrix is added to the remaining pieces. Once the matrix solvent dries completely, the membrane is placed with a clean forceps onto 2 mm sq. pieces of 3M double-sided tape previously adhered to another predetermined area of the stainless steel MALDI target plate.

MALDI-Mass Spectrometry Analysis:

The parameters for the Voyager DE mass spectrometer were as follows: 20,000V accelerating voltage, 94.1% grid voltage, 0.05% guide wire voltage, 110 ns delay, laser set to 2800, 64 scans averaged, and the negative ion mode was off.

Figures 25, 25A:
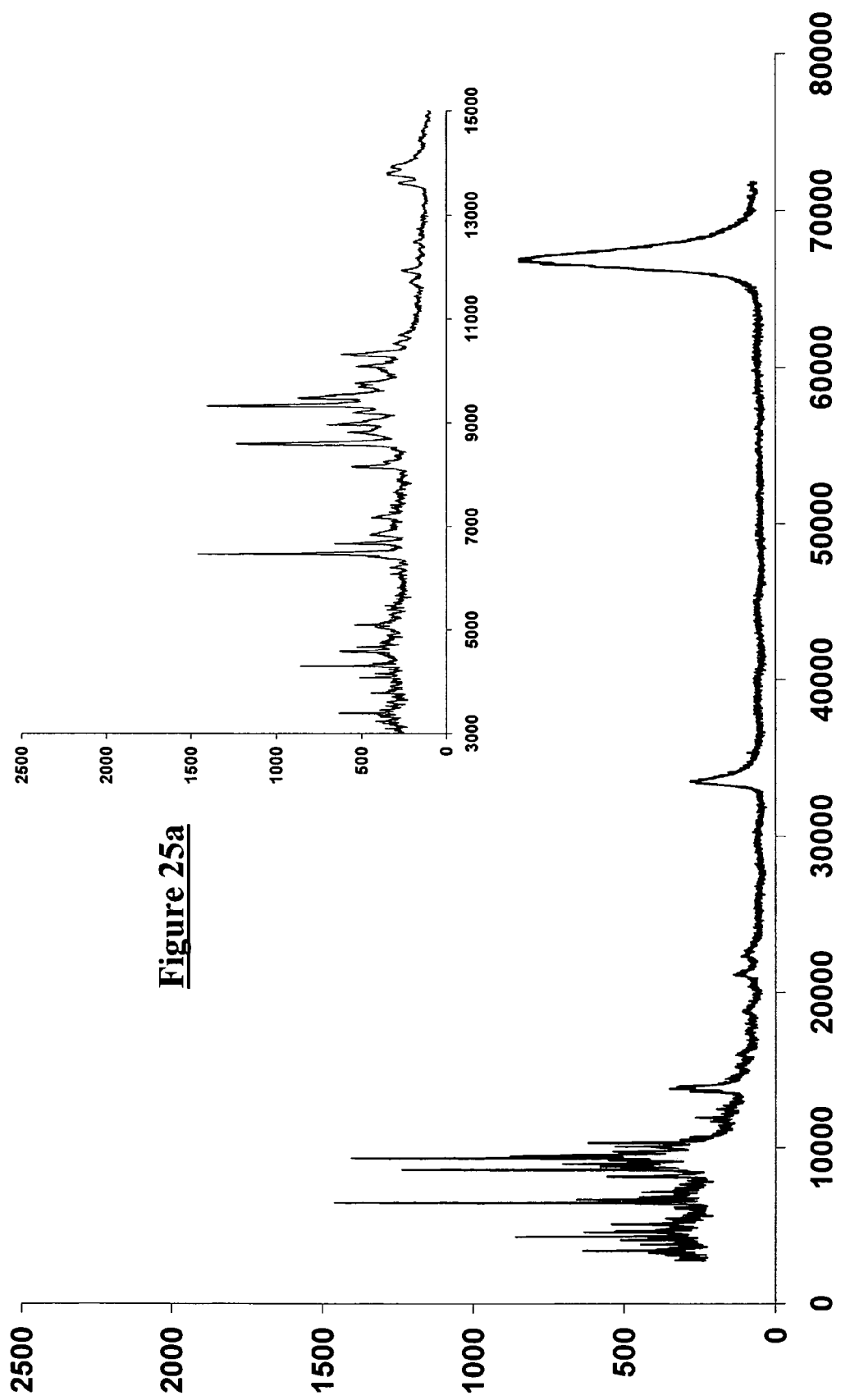
FIGS. 25 & 25A are Mass Spectra of Positively Charged Serum Proteins Electro-Concentrated on PVDF Membrane (with Sinapinic Acid as a MALDI matrix).
Figure 26:
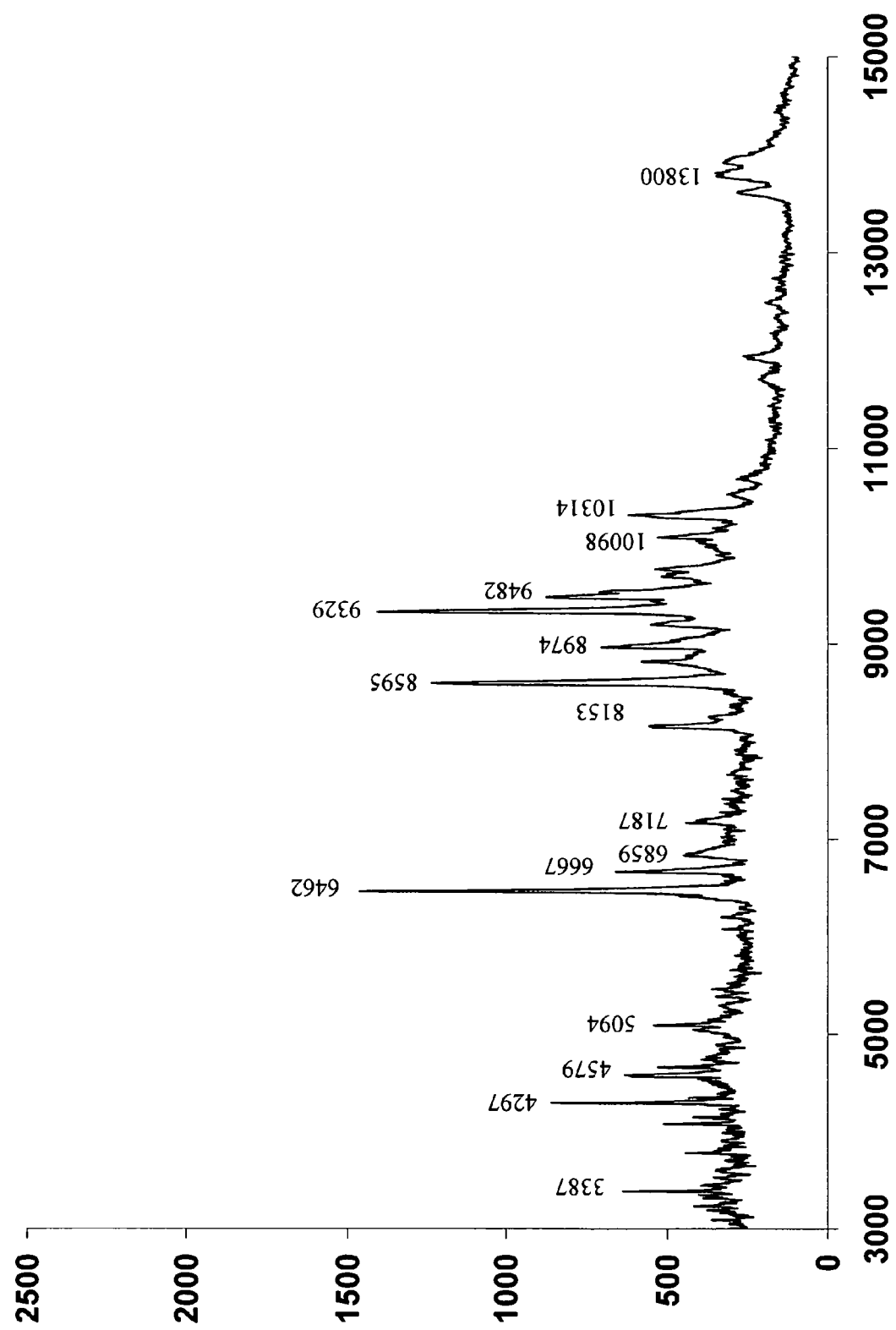
FIG. 26. Mass Spectra of Positively Charged Serum Proteins Electro-Concentrated on PVDF Membrane (with CHCA as a MALDI matrix).

Results:

Shown in FIGS. 25, 25a and 26 are typical MALDI mass spectrometry results for positively-charged peptides and proteins. As can be seen from the Figures, numerous low molecular weight protein mass peaks are detected including mass signals from the labeled ubiquitin tracking protein (as seen at about 8600, 9330 and 10,100 mass units). FIG. 25, depicting the results with sinapinic acid as the MALDI matrix (which tends more optimally ionize moderate sized proteins above 20,000 molecular wt.) shows that only a modest amount of albumin (at about 68,00 mass units) appears. Also, a small peak at about 34,000 units is seen. Other that these two peaks, few mass peaks are seen above 11,000 Daltons, undoubtedly due to the substantial separation of the larger proteins from the smaller polypeptides in the polyacrylamide gel separation layer.

EXAMPLE 4

Capture of Analytes by Porous Capture Media attached to an Array of Electro-Focusing Apertures In this embodiment of the invention, a two-dimensional array of apertures in a solid material is used to electrophoretically concentrate charged analytes into the apertures. Porous media for capture of the analytes is attached at, (i.e. within, or at the entrance or exit ports of) the apertures to capture the concentrated analytes. Each aperture has an associated non-porous perimeter circumscribing a predetermined area of the capture media. The nonporous perimeter serves to retain a liquid solution placed within the predetermined area from occupying a larger area. A device having one, or more, of apertures will be used in a procedure having the following steps:

1.) a deposition step, where an electrically-charged analyte is deposited as a liquid in a sample-retaining volume that is placed in an electrolyte in electrical contact with both an anode, on one side of the aperture, and a cathode on the other side of the aperture;

2.) a focusing and capturing step, where the analyte is electrophretically driven to and focused within the aperture. Also during this step the analyte, still charged, is captured onto a predetermined area of a porous capture media predisposed at the aperture (i.e., within the aperture, or at the entrance or exit port of the aperture), thereby concentrating the charged analyte within the predetermined area;

3.) an analysis step, where the captured charged analyte, advantageously having been concentrated in the predetermined area in the preceding step, is analyzed.

The analysis step additionally will comprise the sub-steps of:
 a) Adding a liquid analytical matrix solution comprising a liquid solvent and a dissolved matrix material, to the porous capture media to release the analyte into the liquid solvent and to a top surface of the porous media,
 b) Retaining the liquid solvent by the nonporous perimeter within the predetermined area of the porous capture media,
 c) Evaporating the solvent to leave the dissolved matrix material and captured analytes within the predetermined area at the top surface of the porous media, and
 d) analyzing the properties of analytes present at the top surface of the predetermined area.

Usually the analysis step will further comprise placing the aperture and attached porous capture media into a mass spectrometer for mass analysis of the analytes. Furthermore, the mass spectrometer usually will be a MALDI mass spectrometer having a laser for performing laser-assisted co-desorption of the matrix solid together with the analytes. Furthermore, the analytes usually will be proteins, polypeptides or and peptides.

Still furthermore, the aperture will usually be present as an array of, substantially identical, such apertures.

Described below are electrophoretic apparatus that may be used in combination with the array of apertures to perform the steps carried out by the invention. Further described are examples of materials and processes that may be used to provide for construction and use of the array of apertures.

In the Example given below the porous capture is porous polyvinylidene difluoride (PVDF) layer (available from Millipore Corporation. Billricia, Mass.) as Immobilon-PSQ membranes and the array of apertures is made in a sheet of solid PVDF (available from McMaster Carr Corporation, Atlanta, Ga.). The nonporous perimeter is made by thermally welding the porous membrane to the solid sheet, around the apertures, as described.

Welding Immobilon-PSQ membranes to Polyvinylidene Difluoride (PVDF) Sheets:

In this example, various means for permanently affixing a porous PVDF capture membrane to a solid film of PVDF, such as Immobilon-PSQ, are described. The methods include thermally welding the porous membrane to a solid material such as a polymer sheet made from 0.010"-thick solid PVDF. In the method the porous membrane is placed over an array of small apertures in the solid polymer sheet. The apertures function to permit elution of adsorbed species, such as peptides and proteins, by solvent flow through the aperture to a top surface of the porous capture membrane.

Figure 27:
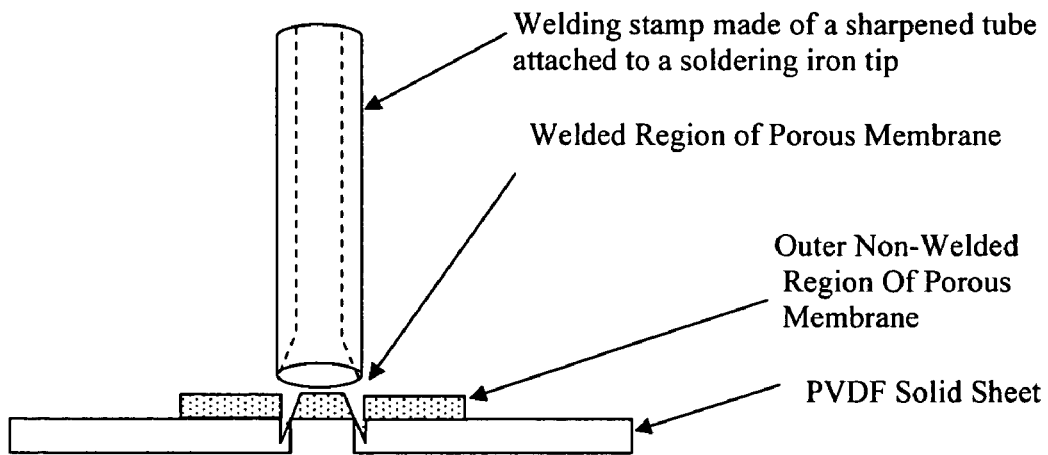
FIG. 27. Welding tool, porous membrane and PVDF sheet
Figure 28:
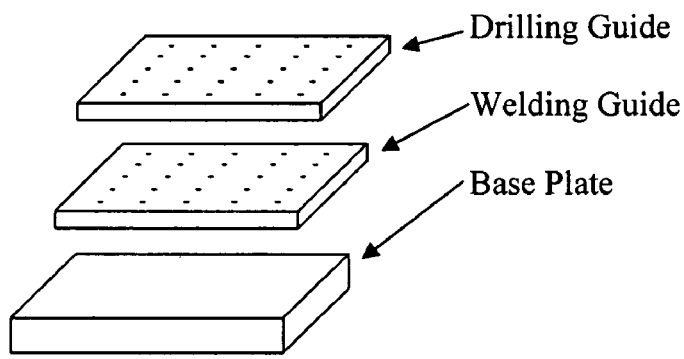
FIG. 28. Drilling Guide, Welding Guide and Base Plate

Welding may be done simply with a heated stamp device such as that shown in FIG. 27. The stamp device, however, optimally will have a temperature-controller device to allow its temperature to be controlled within a specified range of temperatures that are above the melting point of at least one of the membranes to be welded but below the auto-ignition temperature of both. Additionally the welding stamp will have a generally flat bottom region to apply even pressure against at least one of the membrane surfaces, but also will have a hole, generally in the center of the stamp, to create a welded perimeter around a non-welded portion of the membrane. The stamp may be made with a common soldering iron, as described below. To prepare the welding stamp the end of a conical soldering tip is removed; a hole subsequently is drilled into the tip, and a 5 mm long 18 G hypodermic needle is press fit into the hole. The soldering tip is then chucked into a drill press, and the interior of the hypodermic needle is sharpened with a 62° high speed steel countersink bit. A critical consideration when making the welds is alignment of the welding tool over the apertures in the PVDF sheet. A jig may be constructed to align a drill bit over an array of 25 holes, and the welding iron over the same holes for thermally welding the membrane in place as shown in FIG. 28. The jig consists of three components: a polycarbonate base plate, an aluminum drill guide (array of 25 holes, 0.024" in diameter), and an aluminum welding iron guide (array of 25 holes, 0.052" in diameter).

Procedure for Welding PVDF Porous Membrane to PVDF Solid Membrane:

- A 45 mm×45 mm piece of 0.01" thick solid sheet of PVDF is attached to the center of the polycarbonate base plate by means of an adhesive layer of 3M, double-sided tape.
- An aluminum drilling guide is screwed to the base plate over the PVDF sheet.
- An array of 25 holes is drilled through the solid PVDF sheet by using a 0.024" inch diameter drill bits and a pin vice designed to be used in a drill press;
- The drilling guide was removed; strips of Immobilon-PSQ membrane were placed over the holes, and the welding iron guide was screwed onto the base. The holes in the welding iron guide were aligned exactly over the holes in the PVDF sheet.
- The soldering iron was set to about 850° F., and allowed to warm for several minutes.
- The tip of the iron was pushed into the guide holes in the aluminum plate until it contacted the membrane. The iron was held against the membrane for 1-10 seconds until an acceptable weld was created.
- After welding the membrane over all 25 holes, the guide was removed, and the membranes were inspected under a microscope.
- Using forceps, the membrane surrounding the welds was removed.
- The welded arrays were then soaked in methanol and sonicated for 10 minutes.
- The sheets containing the welded membranes were dried and placed into plastic bags until ready for use.

Figure 29:
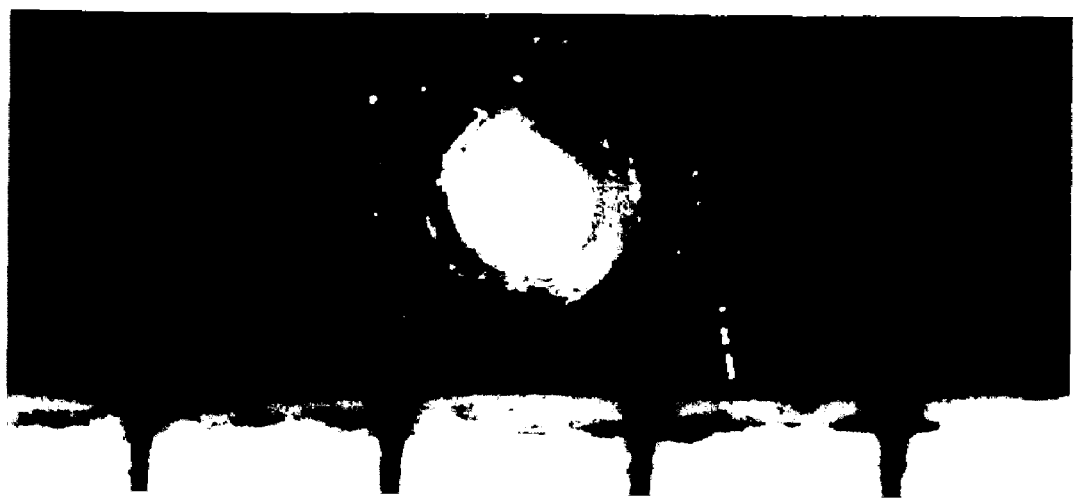
FIG. 29. Porous region of a welded capture membrane. The perimeter of the weld was between 0.5 and 1 mm in diameter FIG. 30. Welded membrane coated with 0.5 uL of MALDI matrix FIG. 31 Mass Spectrum of 5 femtomoles of ACTH (fragment 18-39) on a Porous Capture Membrane Welded to a Solid PVDF Membrane.
Figure 30:
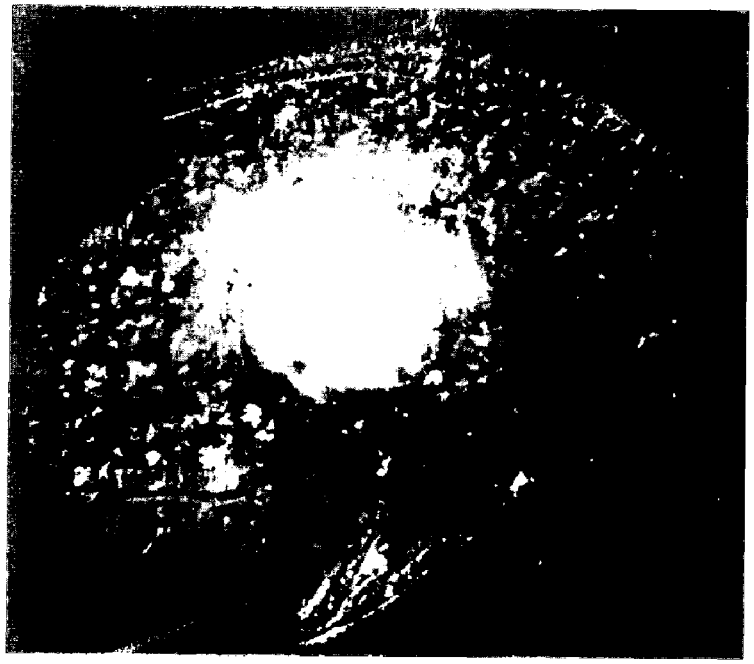

Results of membrane welding and application of a solution containing a MALDI matrix material are shown if FIGS. 29 and 30.

Figure 31:
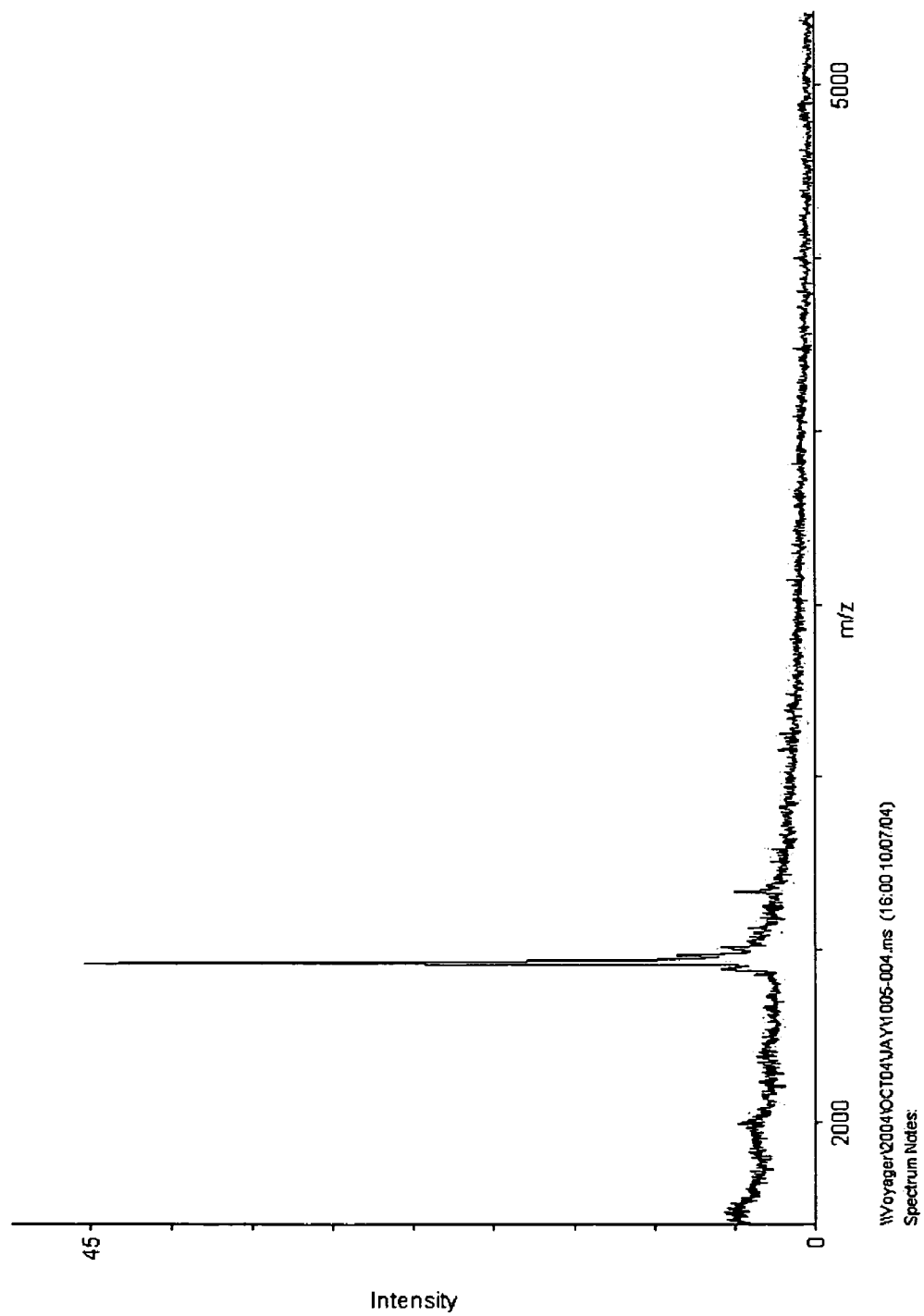

Mass spectral analysis of an extracted sample: A PDVF-PSQ membrane was welded to over an aperture in a solid PVDF sheet, as described above. Next, the porous membrane was wetted with 1 microliter of methanol and an analyte, comprising a peptide fragment of ACTH, was applied to the front side of the porous membrane (side opposite to the solid PVDF) in approximately 0.5 microliter of aqueous PBS buffering solution. The analyte was eluted to the opposite surface with 2×0.3 microliters of a MALDI matrix solution composed of 80:20 ACN/water mixture containing sinapinic acid (SA) matrix (dissolved at 10 mg/mL in 80% acetonitrile, 20% 0.1% trifluoroacetic acid). All materials for the MALDI matrix solution was obtained from Sigma Chem. Co. The backside of the membrane was analyzed by MALDI-TOF. The results are shown as a mass spectrum in FIG. 31.

EXAMPLE 5

Figure 32:
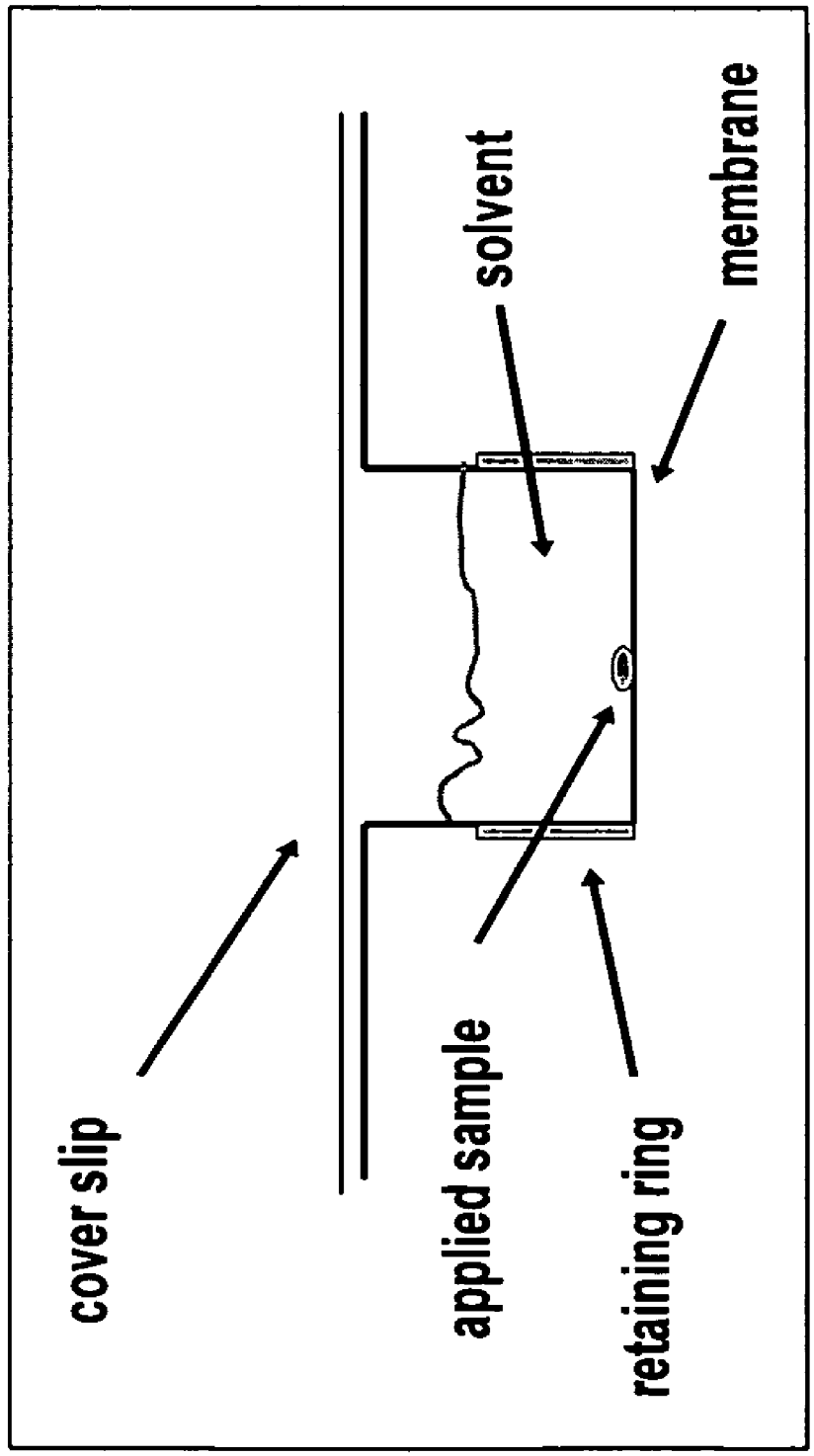
FIG. 32. Schematic Diagram of a Basic Embodiment of an Aperture with Attached Porous Membrane.
Figure 33B:
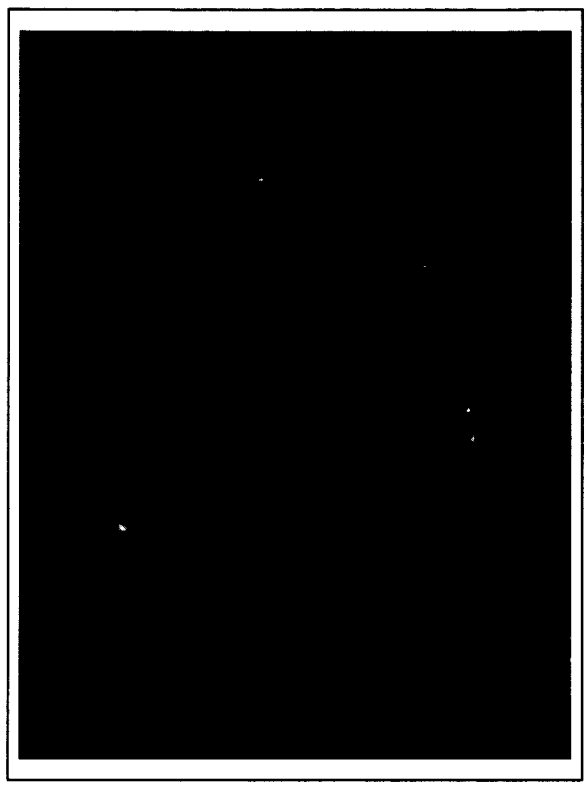
FIGS. 33A & 33B are fluorescence image of a fluorescent analyte (Tr-Ubiquitin) bound to capture membrane before extraction of sample with solvent. Shown on the left (33A) is the image of the top (sample application side) of membrane. On the right (33B) is shown the image of the bottom (on the side opposite to sample application) side of the capture membrane.
Figure 33A:
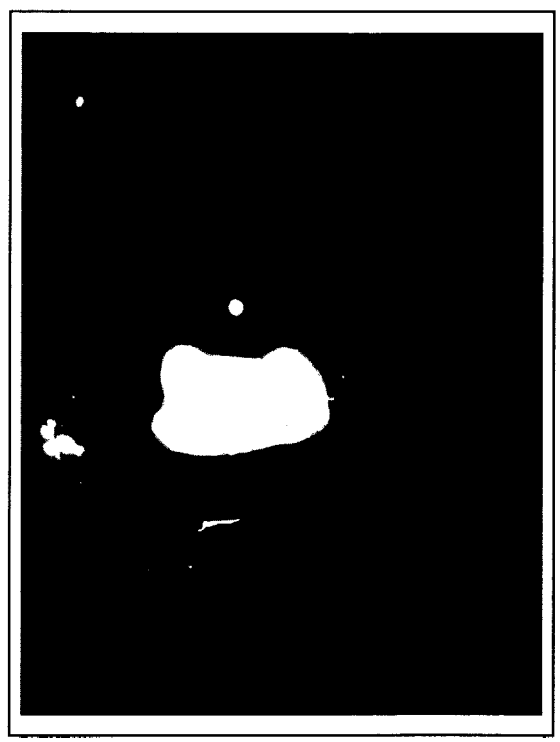
Figure 34B:
FIGS. 34A & 34B are fluorescence images of a fluorescent analyte (Tr-Ubiquitin) bound to porous PVDF capture membrane after release a suitable releasing solvent Acetonitrile/water—50:50. Shown on the left (34A) is the image of the top (sample application side) of membrane. On the right (34B) is shown the image of the bottom (on the side opposite to sample application) side of the capture membrane.
Figure 34A:
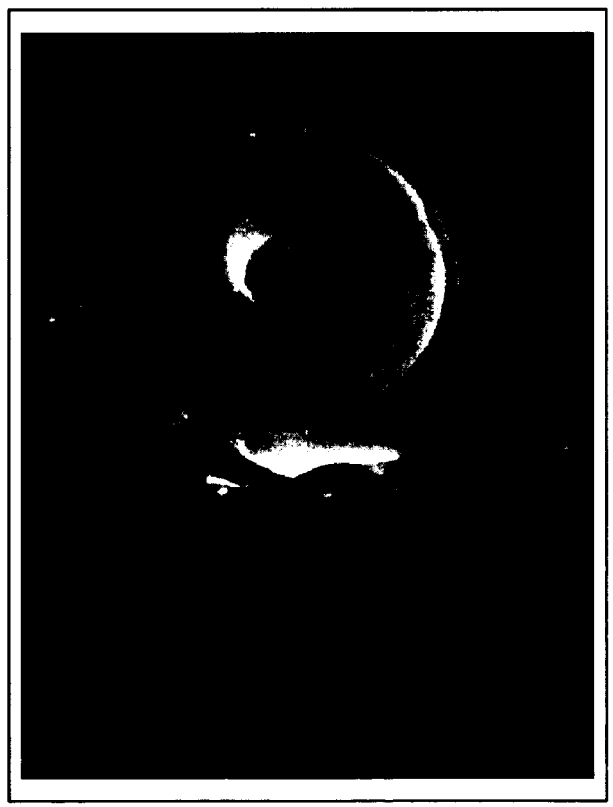

Concentration and Capture of Protein Analytes into a Porous Monolith Cast into Apertures in a Solid Polymeric Film and Subsequent Extraction for MALDI-TOF Analysis Shown in FIG. 32 is a schematic diagram of a basic structure for the capture and subsequent extraction of protein and polypeptide analytes for analysis by MALDI-mass spectrometry. The construct is composed of a plastic frame that contains apertures as one or more micro-apertures. The apertures, or perforations, advantageously are of small diameter, ordinarily between 1 micron and 2 millimeters in diameter. More usually the perforations are between 100 microns and 1 millimeter in diameter. The lower section of the chamber is covered with a porous protein capture membrane such as PVDF-PSQ (Immobilon membrane available from Millipore Corp., Billericia, Mass.). The capture membrane is sealed onto the plastic frame by using one or more sealing means. The simplest sealing means consists of a retaining ring, such as a nylon washer made to fit over plastic retaining ring. A glass cover slip covers the chamber after sample and solvent have been applied.

Procedure: A small quantity (~10 picomole) of Texas-Red-Ubiquitin (in water) was placed onto the upper section of the dry PVDF-PSQ membrane. Sample was dried under vacuum. To the sample 40 microliters of a Acetonitrile/water solution was added and the cover slip placed onto of the plastic frame. The solution was allowed to elute from below and evaporate. This procedure was repeated twice more, so a total amount of solution had been used per sample. For our investigations, the following solutions were investigate for the most efficient extraction of Tr-Ubiquitin. Ratios of acetonitrile to water (ACN/water) used were: 100:0; 95:5; 90:10; 80:20; 70:30; 50:50.

Results: Fluorescence images were taken of the top portion of membrane (spotted sample) and the lower portion of the membrane (extracted sample). Some of the results are shown below in FIGS. 33A & 33B and 34A & 34B. The solvent or the most efficient extraction was found to be 80:20.

EXAMPLE 6

Capture of Analytes in Monolithic Porous Capture Material Formed in an Array of Electro-Focusing Apertures In this embodiment of the invention, a monolithic porous capture material is formed in a two-dimensional array of apertures in a solid material. In this embodiment, charged analytes are electrophoretically concentrated into the monolithic porous capture material formed in an array of electro-focusing apertures. Porous media for capture of the analytes was cast into a series of 200 μm diameter holes previously drilled in a polyvinylidene fluoride (PVDF) support layer. The inside walls of the hole was functionalized to better hold the polymer material once its porous polymerization was complete. The porous material was fabricated in situ using methyl methacrylate as the polymer material. Generally, the support layer was placed on top of a UV transparent Tefon-coated quartz slide and the polymer material was pipetted into the hole. Next, the top of the hole was covered by another UV transparent Tefon-coated quartz slide such that no air bubbles were present. Finally, the material was subjected to UV light for an appropriate period of time to form a porous "filling." The individual spots were investigated and found to be uniform in porosity and both the top and bottom were flush with the top and bottom surfaces of the support layer.

Figure 35:
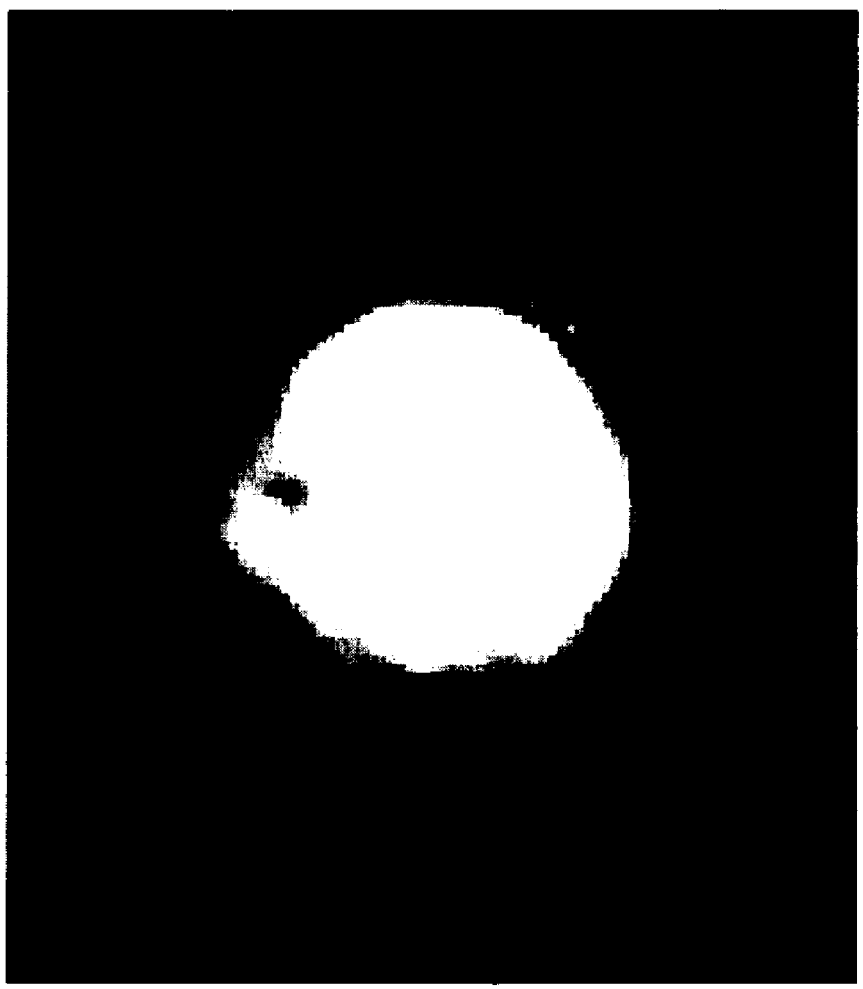
FIG. 35. A 200 μm diameter monolithic porous capture site formed in a through hole drilled in a polymer support layer FIGS. 36A, 36B, 36C and 36D—MALDI mass spectra are shown as taken directly from four separate monolithic porous capture sites formed in place in a support layer. The ACTH fragment is detected at each of the four sites.
Figure 36A:
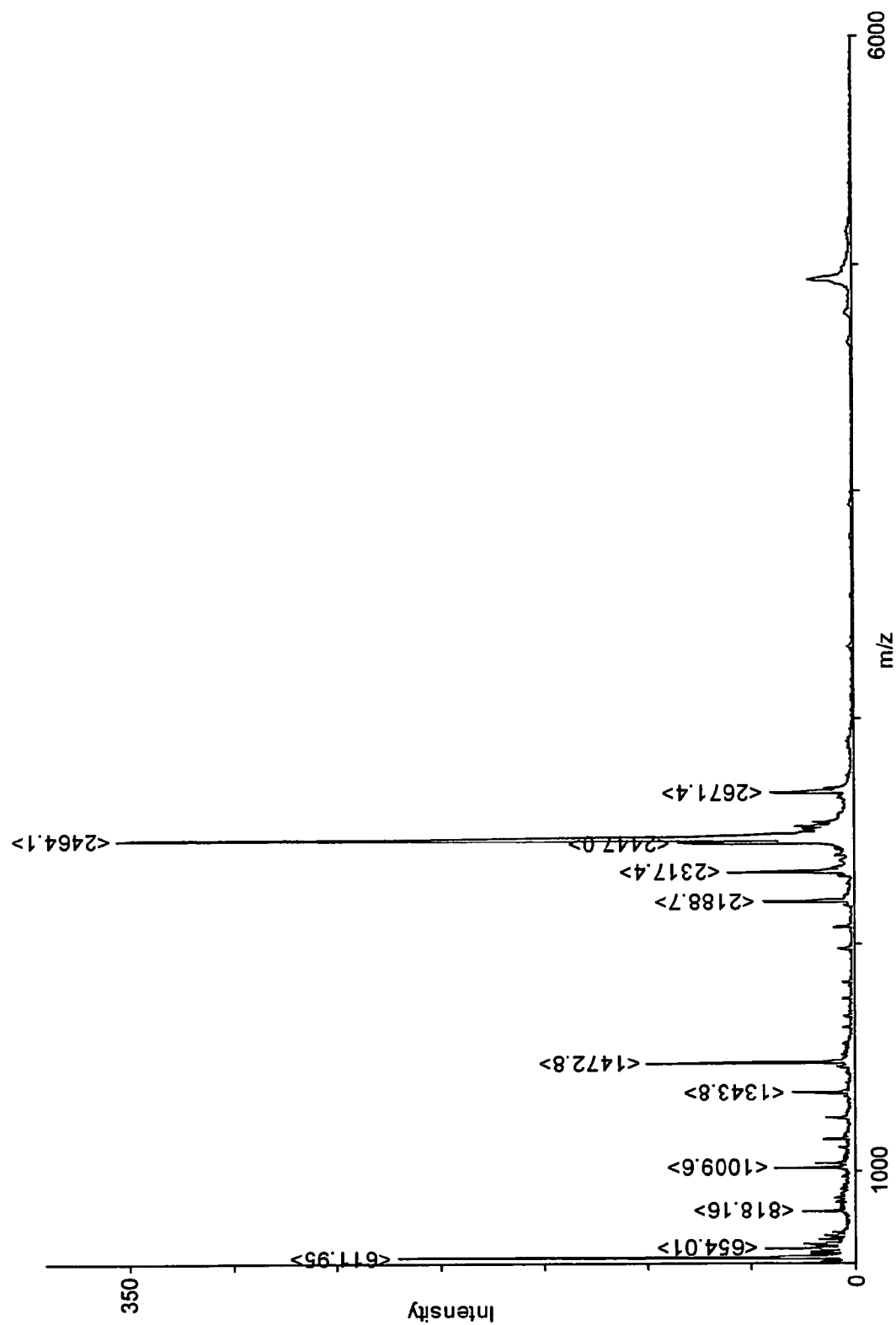
Figure 36B:
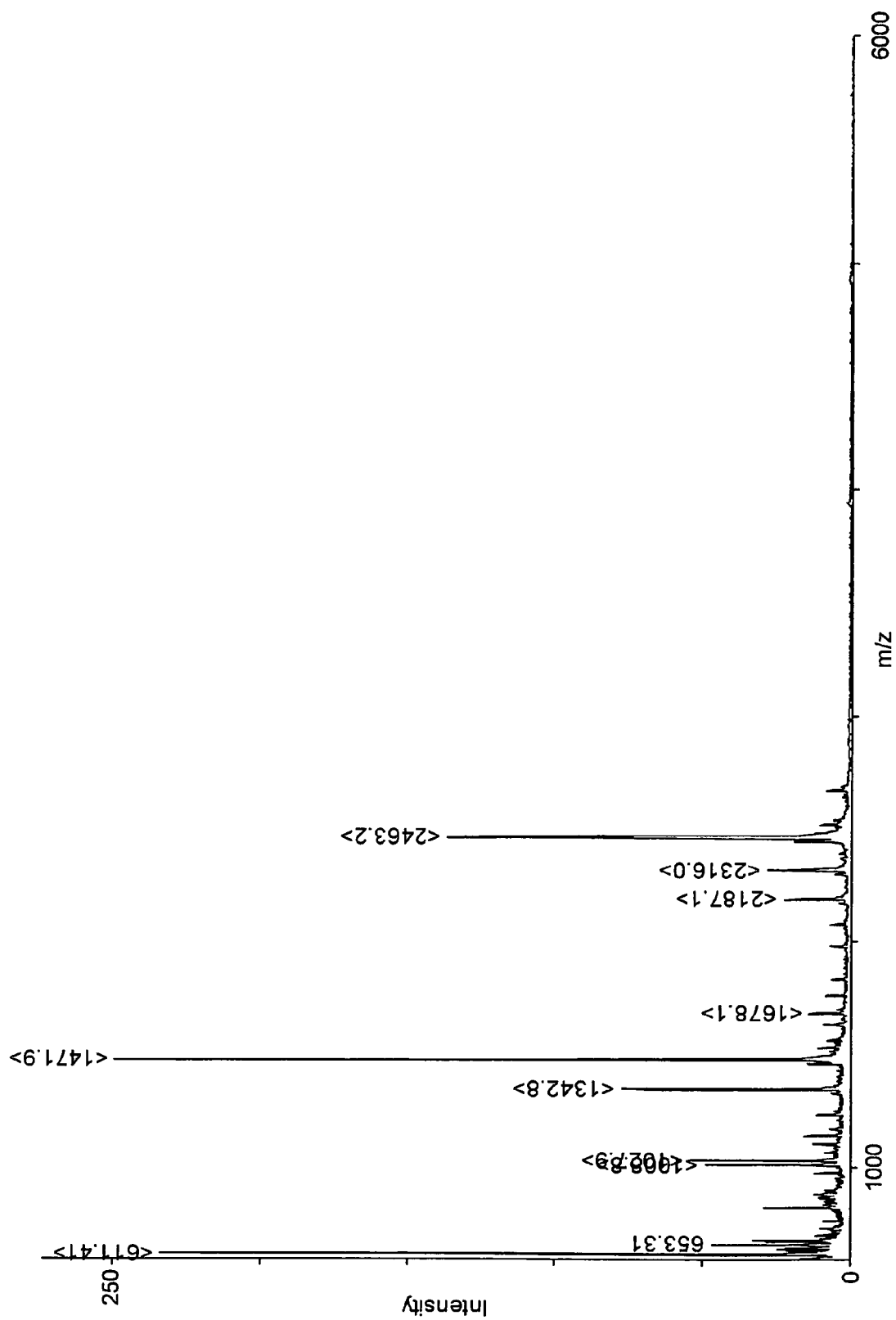
Figure 36C:
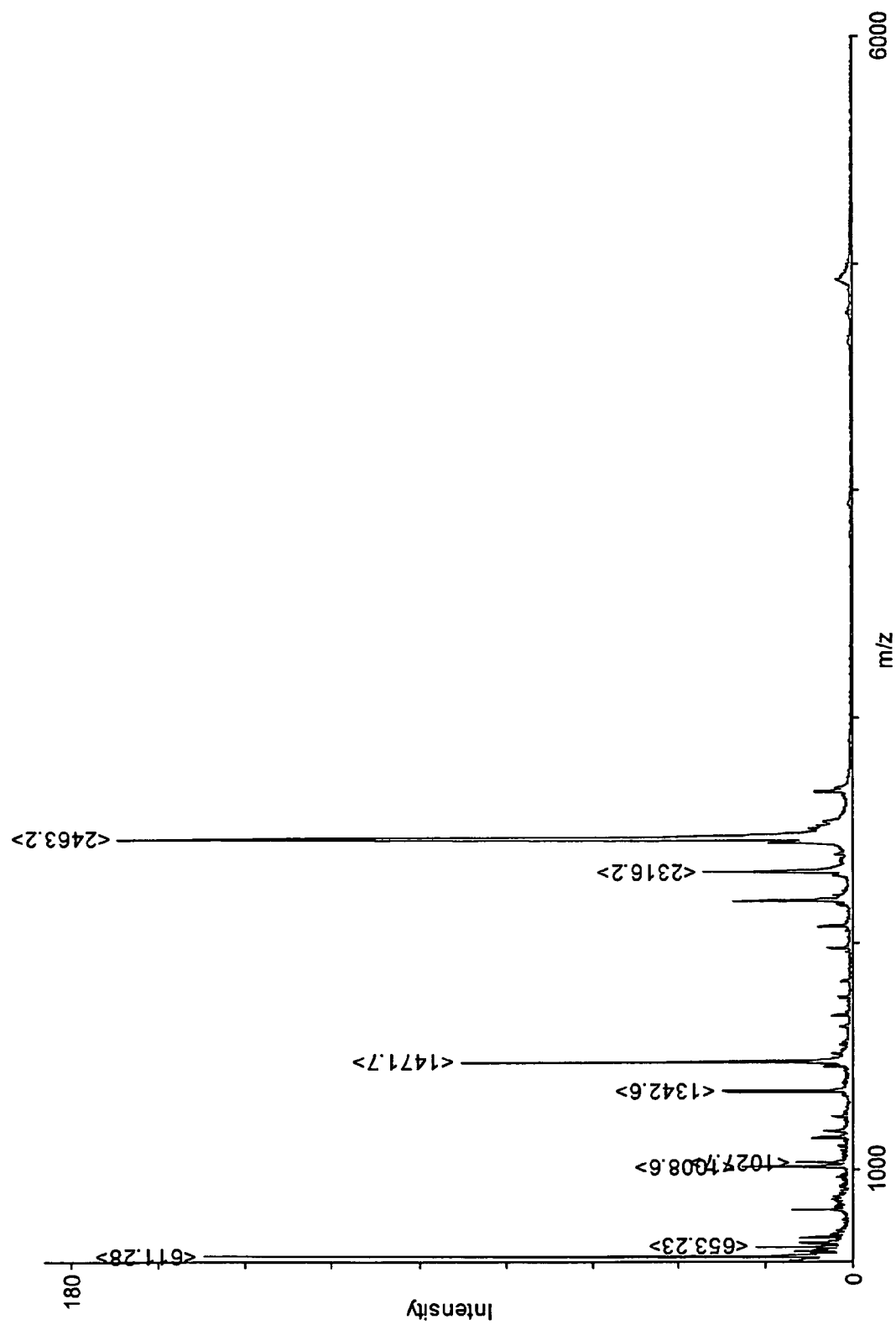
Figure 36D:
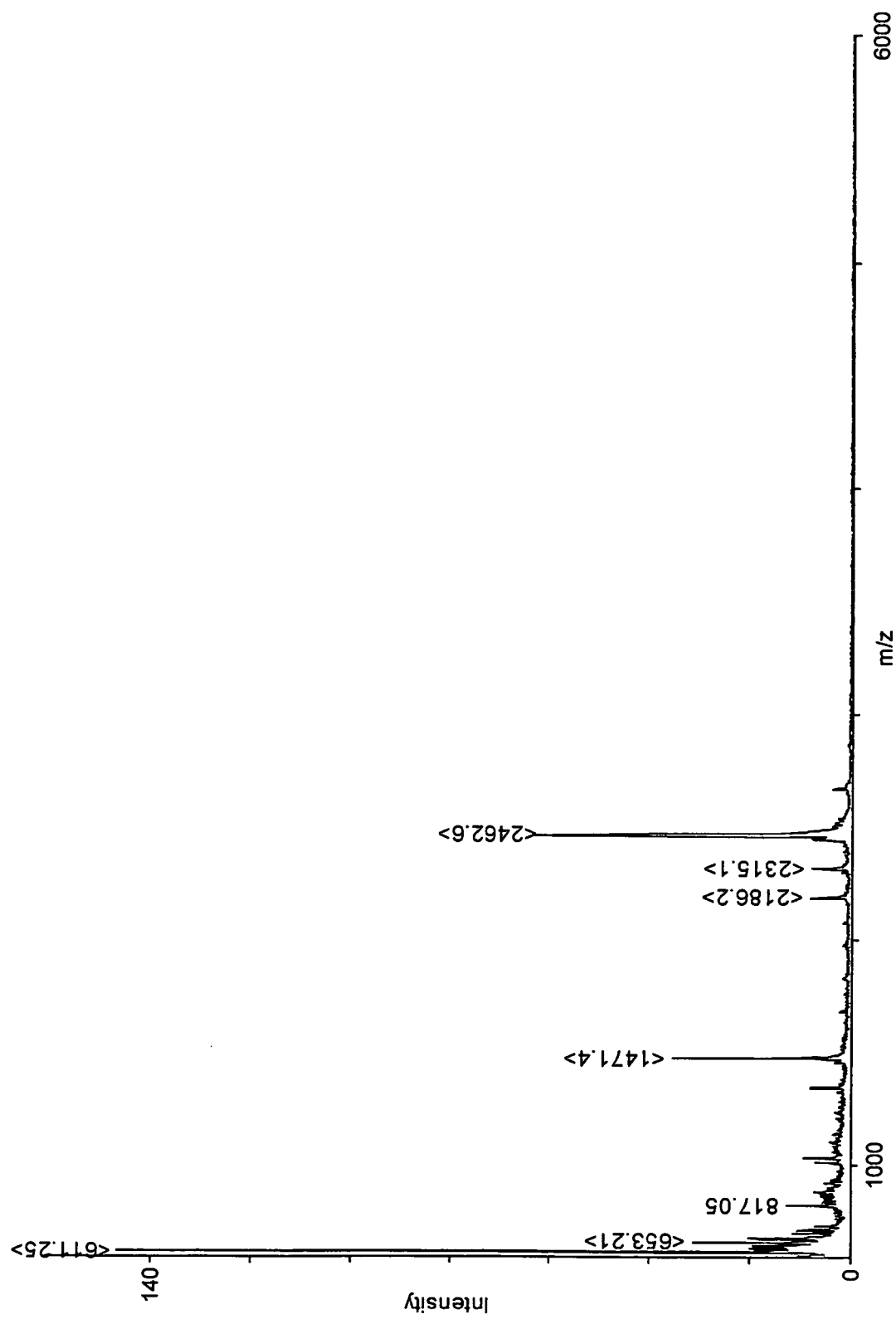

In our experiments, each of monolithic porous capture sites were washed thoroughly with deionized water and sonicated to remove any residual polymer or any other potential contaminant. Following washing with water, each of the sites was washed thoroughly with methanol, then rinsed with 0.1% TFA. Next, 500 fmol of ACTH fragment 18-39 in 500 fmol of BSA was pipetted onto each of the monoliths in a 0.5 μL droplet. Once the samples had dried on the monoliths, each site was rinsed with water and 1 μL of saturated sinapinic acid in 80:20 acetonitrile/0.1% TFA was added to the backside (i.e. the side opposite sample introduction) of the monolith. Finally, the support layer encompassing the array of monolithic porous capture sites was allowed to sufficiently dry and was placed into the MALDI mass spectrometer and analyzed. FIG. 35 shows a single porous capture site cast in place via the in situ porous polymerization process. FIGS. 36 (A-D) show several MALDI mass spectra resulting from four different monolithic porous capture sites in the array. In all cases, the ACTH fragment of interest was detected.

What is claimed is:
1. An assembly for performing a multiplicity of electrophoretic separations on samples containing two or more analytes comprising:
a top layer including a plurality of sample wells, each sample well having a bottom and side walls forming an opening for accepting a liquid sample including a liquid and one or more analytes;
a capture layer for retaining at least one analyte; and
a separation layer located between the top layer and the capture layer wherein the bottom of each well is sealed by the separation layer and wherein the separation layer is differentially porous only to the at least one analyte in the liquid sample
wherein when a current is applied across the capture layer and the separation layer, the separation layer prevents a second analyte from reaching the capture layer by electrophoresis and wherein the separation layer and the capture layer do not include channels or chambers.
2. The assembly of claim 1 wherein the capture layer is a hydrophobic membrane.
3. The assembly of claim 1 wherein the capture layer is a dialysis membrane made of a protein binding material.
4. The assembly of claim 1 including a porous layer located between the top surface and the separation layer.
5. The assembly of claim 1 including a porous layer located between the capture layer and the separation layer.
6. The assembly of claim 1 including a barrier layer located adjacent to the capture layer.
7. The assembly of claim 6 including a buffer layer wherein the barrier layer is located between the capture layer and the buffer layer.
8. The assembly of claim 1 including a porous layer located between the top surface and the separation layer.
9. The assembly of claim 1 including a constriction layer located between the separation layer and the capture layer wherein the constriction layer includes a impermeable region and at least one aperture wherein the at least one constriction layer aperture is concentric to and in liquid communication through a porous materials with a well aperture.
10. The assembly of claim 9 wherein a porous, bibulous hydrophilic material is located in at least one constriction layer aperture.
11. The assembly of claim 9 wherein the constriction layer impermeable region is adhered to the capture layer.
12. The assembly of claim 11 wherein the constriction layer impermeable region is adhered to the capture layer by heat welding to form an annular weld around the periphery of at least one constriction layer aperture.
13. The assembly of claim 1 including a first constriction layer including a first constriction layer aperture and a second constriction layer including a second constriction layer aperture, wherein the capture layer is located between the first constriction layer and the second constriction layer and wherein the well aperture, first constriction layer aperture and second constriction layer aperture are all concentric to one another.
14. The assembly of claim 13 wherein both the first constriction layer and the second constriction layer each have at least one aperture that is in liquid communication through porous materials with a well aperture.
15. The assembly of claim 1 wherein the capture layer includes at least one marker that is readable by a mass spectrometer.
16. The assembly of claim 1 wherein the capture layer has a marker location that is readable by a mass spectrometer and where a capture region is located at a known distance from the marker location.
17. The assembly of claim 1 including a constriction layer located between the separation layer and the porous capture layer wherein the constriction layer includes an impermeable region and at least one aperture concentric to at least one top surface aperture; and an annular weld in the constriction layer wherein the annular weld surrounds the periphery of the at least one constriction layer aperture.
18. The assembly of claim 1 including a conductive slide wherein the porous capture layer is attached to the conductive slide and wherein the conductive slide is insertable into a mass spectrometer.
19. The assembly of claim 1 wherein the separation layer is a polyacrylamide separation layer.

20. The assembly of claim 1 wherein each well includes a concentric capture layer and separation layer.

21. A method for performing a multiplicity of electrophoretic separations on samples containing a liquid and two or more analytes by the steps comprising:
    forming an assembly comprising a top layer including a multiplicity of sample wells each sample well having side walls forming an opening and a bottom, a capture layer located between an anode and a cathode, and a separation layer located between the top layer and the capture layer wherein the bottom of each sample well is sealed by the separation layer and wherein the separation layer is differentially porous only to at least one analyte in each of the liquid samples and wherein the separation layer and the capture layer do not include channels or chambers;
    locating a liquid sample in two or more of the multiplicity of sample wells;
    electrophoretically transporting analytes from the of liquid samples located in two or more sample wells by applying a current to the liquid samples using the anode and the cathode;
    electrophoretically separating two or more analytes in two or more of the liquid samples by applying a current polarity that causes a first analyte to move towards the cathode and a second analyte to move towards the anode;
    capturing the first analyte from the liquid samples in two or more of the sample wells onto different locations on the capture layer; and
    removing the capture layer including the electrophoretically separated first analytes on different locations on the capture layer from the assembly.

22. A method for performing a multiplicity of electrophoretic separations on liquid samples including a liquid and two or more analytes by the steps comprising:
    forming an assembly comprising a top layer including a multiplicity of sample wells each sample well having side walls forming an opening and a bottom, a capture layer located between an anode and a cathode, and a separation layer located between the top layer and the capture layer wherein the bottom of each sample well is sealed by the separation layer and wherein the separation layer is differentially porous only to one or more analytes in the liquid samples and wherein the separation layer and the capture layer do not include channels or chambers;
    locating liquid sample each sample including a liquid and two or more analytes in two or more of the multiplicity of sample wells;
    separating two or more analytes in liquid samples located in two or more sample wells by electrophoresing two or more analytes from the liquid samples through a porous separation layer to cause a first analyte to move more quickly through the separation layer than a second analyte;
    stopping the electrophoresis when the first analytes have moved through the separation layer and have been captured on the capture layer; and
    removing the capture layer including the first analytes from the assembly.

23. A method for performing a multiplicity of concentrations on samples containing one or more analytes by the steps comprising:
    forming an assembly comprising a top layer including a multiplicity of sample wells each sample well having side walls forming an opening and a bottom, a capture layer located between an anode and a cathode, and a separation layer located between the top layer and the capture layer wherein the bottom of each sample well is sealed by the separation layer, wherein the separation layer is differentially porous only to the at least one of the one or more analytes in the liquid sample and wherein the separation layer and the capture layer do not include channels or chambers;
    locating liquid samples each including a liquid and at least one analyte in each of at least two or more of the multiplicity of sample wells;
    electrophoretically transporting the at least one analyte from the liquid samples through the separation layer;
    capturing the at least one analyte on the capture layer; and
    removing the capture layer from the assembly.

24. The assembly of claim 1 wherein the porous capture layer is concentric to the top layer.

25. The assembly of claim 24 wherein the porous capture layer is separated from the top layer by no more than 3 intermediate layers including the porous separation layer.

26. The method of claims 21 or including the further steps of:
    applying a MALDI matrix to the capture layer;
    attaching the capture layer to a MALDI mass spectrometer analysis plate; and
    analyzing at least one analyte in the capture layer by mass spectrometry.

27. The method of claim 26 wherein the capture layer includes a marker location that is readable by the mass spectrometer and where the capture region is a known distance from the marker location.

28. The method of claim 23 wherein the assembly includes an electrode layer with photoreduction regions wherein the at least one analyte is concentrated in the capture layer by placing a counter electrode in electrical communication with the liquid sample; applying an electric current between the electrode layer and the counter electrode; and illuminating the capture region with a focused light source by directing the light source through the photoreductive regions.

29. The method of claim 26 wherein the capture layer includes a magnetic portion, and the MALDI mass spectrometer analysis plate includes a magnetic portion and wherein the capture layer is magnetically attached to the plate.

30. The method of claim 26 wherein the MALDI matrix is applied only to a capture region of the capture layer.

* * * * *